(12) United States Patent
Lyman et al.

(10) Patent No.: US 11,829,914 B2
(45) Date of Patent: *Nov. 28, 2023

(54) MEDICAL SCAN HEADER STANDARDIZATION SYSTEM AND METHODS FOR USE THEREWITH

(71) Applicant: Enlitic, Inc., San Francisco, CA (US)

(72) Inventors: Kevin Lyman, Fords, NJ (US); Anthony Upton, Malvern (AU); Li Yao, San Francisco, CA (US); Jordan Prosky, San Francisco, CA (US); Eric C. Poblenz, Palo Alto, CA (US); Chris Croswhite, San Jose, CA (US); Ben Covington, Berkeley, CA (US)

(73) Assignee: Enlitic, Inc., Fort Collins, CO (US)

( * ) Notice: Subject to any disclaimer, the term of this patent is extended or adjusted under 35 U.S.C. 154(b) by 150 days.

This patent is subject to a terminal disclaimer.

(21) Appl. No.: 17/680,493

(22) Filed: Feb. 25, 2022

(65) Prior Publication Data

US 2022/0180986 A1    Jun. 9, 2022

Related U.S. Application Data

(63) Continuation of application No. 16/363,289, filed on Mar. 25, 2019, now Pat. No. 11,295,840.

(Continued)

(51) Int. Cl.
*G16H 30/20* (2018.01)
*G06Q 10/0631* (2023.01)
(Continued)

(52) U.S. Cl.
CPC ..... *G06Q 10/06315* (2013.01); *A61B 5/7264* (2013.01); *G06F 3/0482* (2013.01);
(Continued)

(58) Field of Classification Search
CPC ... G06Q 50/22–24; G16H 10/60; G16H 30/20
See application file for complete search history.

(56) References Cited

U.S. PATENT DOCUMENTS

| 6,524,246 B1 | 2/2003 | Kelly |
| 6,937,776 B2 | 8/2005 | Li |

(Continued)

FOREIGN PATENT DOCUMENTS

| CN | 106551704 A | 4/2017 | |
| EP | 2457512 A1 | 5/2012 | |
| EP | 2457512 A1 * | 5/2012 | ........... A61B 6/5294 |

OTHER PUBLICATIONS

"Quality of DICOM header information for image categorization"; Gueld et al.; Proceedings of SPIE; May 16, 2002. (Year: 2002).*

(Continued)

*Primary Examiner* — John A Pauls
(74) *Attorney, Agent, or Firm* — Cochran Freund & Young LLC

(57) ABSTRACT

A medical scan header standardization system is operable to determine a plurality of counts for a plurality of entries of at least one of a standard set of fields for headers of a plurality of medical images. A standard set of header entries is determined for at least one of the standard set of fields based on including ones of the entries for the each of the standard set of fields with counts of the plurality of counts that compare favorably to a threshold. One of the standard set of header entries is selected to replace an entry of a field of a header of a medical image. A computer vision model is trained utilizing a training set of images that includes the medical image and the selected one of the standard set of header entries. Inference data for at least one new medical scan is generated based on utilizing the computer vision model.

20 Claims, 37 Drawing Sheets

Related U.S. Application Data

(60) Provisional application No. 62/770,334, filed on Nov. 21, 2018.

(51) Int. Cl.

| | | |
|---|---|---|
| *G16H 10/60* | (2018.01) | |
| *G16H 30/40* | (2018.01) | |
| *G16H 15/00* | (2018.01) | |
| *G06T 5/00* | (2006.01) | |
| *G06T 5/50* | (2006.01) | |
| *G06T 7/00* | (2017.01) | |
| *G06T 11/00* | (2006.01) | |
| *G06N 5/04* | (2023.01) | |
| *G06N 20/00* | (2019.01) | |
| *G06F 9/54* | (2006.01) | |
| *G06T 7/187* | (2017.01) | |
| *G06T 7/11* | (2017.01) | |
| *G06F 3/0482* | (2013.01) | |
| *G06T 3/40* | (2006.01) | |
| *A61B 5/00* | (2006.01) | |
| *G16H 50/20* | (2018.01) | |
| *G06F 21/62* | (2013.01) | |
| *G06Q 20/14* | (2012.01) | |
| *G16H 40/20* | (2018.01) | |
| *G06F 3/0484* | (2022.01) | |
| *G16H 10/20* | (2018.01) | |
| *G06N 5/045* | (2023.01) | |
| *G06T 7/10* | (2017.01) | |
| *G06T 11/20* | (2006.01) | |
| *G06F 16/245* | (2019.01) | |
| *G06T 7/44* | (2017.01) | |
| *G06N 20/20* | (2019.01) | |
| *H04L 67/12* | (2022.01) | |
| *H04L 67/01* | (2022.01) | |
| *G06V 10/82* | (2022.01) | |
| *G06F 18/40* | (2023.01) | |
| *G06F 18/214* | (2023.01) | |
| *G06F 18/21* | (2023.01) | |
| *G06F 18/2115* | (2023.01) | |
| *G06F 18/2415* | (2023.01) | |
| *G06V 10/25* | (2022.01) | |
| *G06V 30/19* | (2022.01) | |
| *G06V 10/764* | (2022.01) | |
| *G06V 40/16* | (2022.01) | |
| *G06V 10/22* | (2022.01) | |
| *G16H 50/70* | (2018.01) | |
| *G06T 7/70* | (2017.01) | |
| *G16H 50/30* | (2018.01) | |
| *A61B 5/055* | (2006.01) | |
| *A61B 6/03* | (2006.01) | |
| *A61B 8/00* | (2006.01) | |
| *A61B 6/00* | (2006.01) | |
| *G06Q 50/22* | (2018.01) | |
| *G06F 40/295* | (2020.01) | |
| *G06F 18/24* | (2023.01) | |
| *G06F 18/2111* | (2023.01) | |
| *G06V 30/194* | (2022.01) | |

(52) U.S. Cl.
CPC .......... *G06F 3/0484* (2013.01); *G06F 9/542* (2013.01); *G06F 16/245* (2019.01); *G06F 18/214* (2023.01); *G06F 18/217* (2023.01); *G06F 18/2115* (2023.01); *G06F 18/2415* (2023.01); *G06F 18/41* (2023.01); *G06F 21/6254* (2013.01); *G06N 5/04* (2013.01); *G06N 5/045* (2013.01); *G06N 20/00* (2019.01); *G06N 20/20* (2019.01); *G06Q 20/14* (2013.01); *G06T 3/40* (2013.01); *G06T 5/002* (2013.01); *G06T 5/008* (2013.01); *G06T 5/50* (2013.01); *G06T 7/0012* (2013.01); *G06T 7/0014* (2013.01); *G06T 7/10* (2017.01); *G06T 7/11* (2017.01); *G06T 7/187* (2017.01); *G06T 7/44* (2017.01); *G06T 7/97* (2017.01); *G06T 11/001* (2013.01); *G06T 11/006* (2013.01); *G06T 11/206* (2013.01); *G06V 10/225* (2022.01); *G06V 10/25* (2022.01); *G06V 10/764* (2022.01); *G06V 10/82* (2022.01); *G06V 30/19173* (2022.01); *G06V 40/171* (2022.01); *G16H 10/20* (2018.01); *G16H 10/60* (2018.01); *G16H 15/00* (2018.01); *G16H 30/20* (2018.01); *G16H 30/40* (2018.01); *G16H 40/20* (2018.01); *G16H 50/20* (2018.01); *H04L 67/01* (2022.05); *H04L 67/12* (2013.01); *A61B 5/055* (2013.01); *A61B 6/032* (2013.01); *A61B 6/5217* (2013.01); *A61B 8/4416* (2013.01); *G06F 18/2111* (2023.01); *G06F 18/24* (2023.01); *G06F 40/295* (2020.01); *G06Q 50/22* (2013.01); *G06T 7/70* (2017.01); *G06T 2200/24* (2013.01); *G06T 2207/10048* (2013.01); *G06T 2207/10081* (2013.01); *G06T 2207/10088* (2013.01); *G06T 2207/10116* (2013.01); *G06T 2207/10132* (2013.01); *G06T 2207/20076* (2013.01); *G06T 2207/20081* (2013.01); *G06T 2207/20084* (2013.01); *G06T 2207/30004* (2013.01); *G06T 2207/30008* (2013.01); *G06T 2207/30016* (2013.01); *G06T 2207/30061* (2013.01); *G06V 30/194* (2022.01); *G06V 2201/03* (2022.01); *G16H 50/30* (2018.01); *G16H 50/70* (2018.01)

(56) References Cited

U.S. PATENT DOCUMENTS

| | | |
|---|---|---|
| 7,123,762 B2 | 10/2006 | Giger |
| 7,418,123 B2 | 8/2008 | Giger |
| 7,813,822 B1 | 10/2010 | Hoffberg |
| 8,121,362 B2 | 2/2012 | Zhan |
| 8,303,505 B2 | 11/2012 | Webler |
| 9,165,360 B1 | 10/2015 | Bates |
| 9,569,736 B1 | 2/2017 | Ghesu |
| 9,579,518 B2 | 2/2017 | Gertner |
| 9,760,978 B1 | 9/2017 | Lu |
| 2002/0186818 A1 | 12/2002 | Arnaud |
| 2004/0147840 A1 | 7/2004 | Duggirala |
| 2004/0252870 A1 | 12/2004 | Reeves |
| 2005/0283450 A1 | 12/2005 | Matsugu |
| 2008/0015418 A1 | 1/2008 | Jarrell |
| 2008/0021834 A1 | 1/2008 | Holla |
| 2008/0205717 A1 | 8/2008 | Reeves |
| 2008/0267483 A1 | 10/2008 | Zhan |
| 2009/0177495 A1 | 7/2009 | Abousy |
| 2009/0222388 A1 | 9/2009 | Hua |
| 2011/0188718 A1* | 8/2011 | Hill .............. G16H 30/40 382/128 |
| 2013/0173308 A1* | 7/2013 | Hough ............ G16H 40/67 705/3 |
| 2014/0341471 A1 | 11/2014 | Ono et al. |
| 2015/0031979 A1 | 1/2015 | Rappaport et al. |
| 2015/0063667 A1 | 3/2015 | Sprencz |
| 2015/0305706 A1 | 10/2015 | Kanik |
| 2016/0019695 A1 | 1/2016 | Chukka |
| 2016/0027175 A1 | 1/2016 | Kim et al. |
| 2016/0104281 A1 | 4/2016 | Grady |
| 2016/0203281 A1 | 7/2016 | Zalis |
| 2016/0314588 A1 | 10/2016 | Harper |

(56) References Cited

U.S. PATENT DOCUMENTS

| | | |
|---|---|---|
| 2016/0343127 A1 | 11/2016 | Miller |
| 2017/0116497 A1 | 4/2017 | Georgescu |
| 2018/0025255 A1 | 1/2018 | Poole |
| 2018/0033144 A1 | 2/2018 | Risman |
| 2018/0060535 A1 | 3/2018 | Reicher |
| 2018/0060691 A1 | 3/2018 | Bernal |
| 2018/0114595 A1 | 4/2018 | Stern |
| 2018/0204111 A1 | 7/2018 | Zadeh |

OTHER PUBLICATIONS

Andersch, Michael; Inference: The Next Step in GPU-Accelerated Deep Learning; https://devblogs.nvidia.com/parallelforall/inference-next-step-gpu-accelerated-deep-learning/; Nov. 11, 2015; 7 pages.

International Searching Authority; International Search Report and Written Opinion; International Application No. PCT/US2018/032927; dated Sep. 14, 2018; 9 pgs.

Minnaar, Alex; Deep Learning Basics: Neural Networks, Backpropagation and Stochastic Gradient Descent; http://alexminnaar.com/deep-learning-basics-neural networks-backpropagation-and-stochastic-gradient-descent.html; Feb. 14, 2015; 11 pages.

Olah, Christopher; Calculus on Computational Graphs: Backpropagation; http://colah.github.io/posts/2015-08-Backprop/; Aug. 31, 2015; 7 pages.

Pre Conference Proceedings of the 7th MICCAI BraTS Challenge (2018); BraTS Multimodal Brain Tumor Segmentation Challenge; Granada, Spain; Sep. 16, 2018; 578 pages.

Reid, Stuart; 10 misconceptions about Neural Networks; http://www.turingfinance.com/misconceptions-about-neural-networks/; May 8, 2014; 24 pages.

Wikipedia: Backpropagation; https://en.wikipedia.org/wiki/Backpropagation#Assumptions_about_the_loss_function; downloaded from the internet on 18/15/18; 12 pages.

Wikipedia; Convolutional neural network; https://en.wikipedia.org/wiki/Convolutional_neural_network#Pooling_layer; downloaded from the internet on Jan. 15, 2018; 21 pages.

\* cited by examiner

MEDICAL SCAN HEADER STANDARDIZATION SYSTEM AND METHODS FOR USE THEREWITH

CROSS REFERENCE TO RELATED APPLICATIONS

The present U.S. Utility patent application claims priority pursuant to 35 U.S.C. § 120 as a continuation of U.S. Utility application Ser. No. 16/363,289, entitled "MEDICAL SCAN HEADER STANDARDIZATION SYSTEM", filed Mar. 25, 2019, which claims priority pursuant to 35 U.S.C. § 119(e) to U.S. Provisional Application No. 62/770,334, entitled "LESION TRACKING SYSTEM", filed Nov. 21, 2018, both of which are hereby incorporated herein by reference in their entirety and made part of the present U.S. Utility patent application for all purposes.

STATEMENT REGARDING FEDERALLY SPONSORED RESEARCH OR DEVELOPMENT

Not applicable.

INCORPORATION-BY-REFERENCE OF MATERIAL SUBMITTED ON A COMPACT DISC

Not applicable.

BACKGROUND

Technical Field

This invention relates generally to medical imaging devices and knowledge-based systems used in conjunction with client/server network architectures.

DESCRIPTION OF RELATED ART

Brief Description of the Several Views of the Drawing(s)

Figure 11:
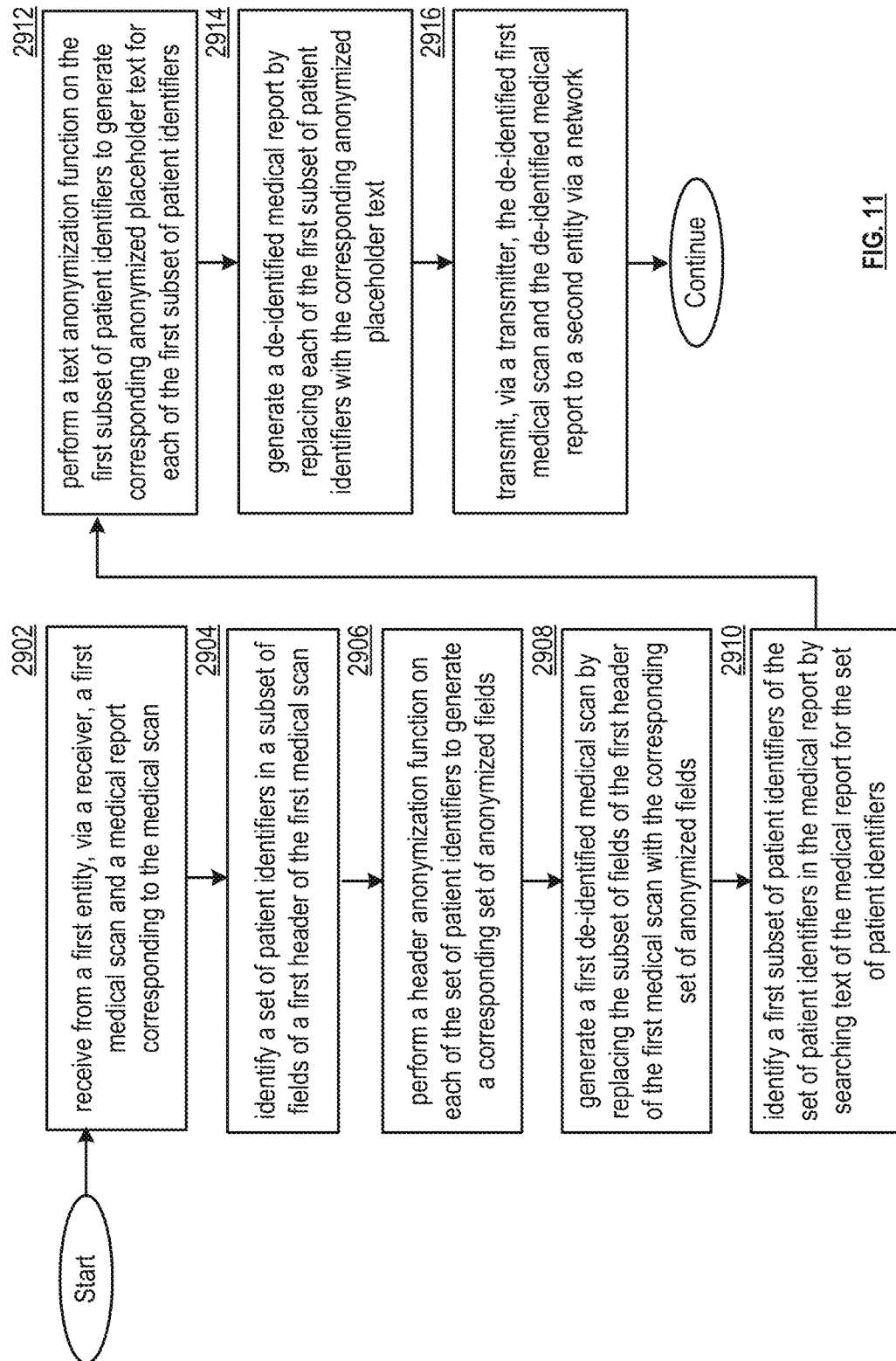
Figure 13A:
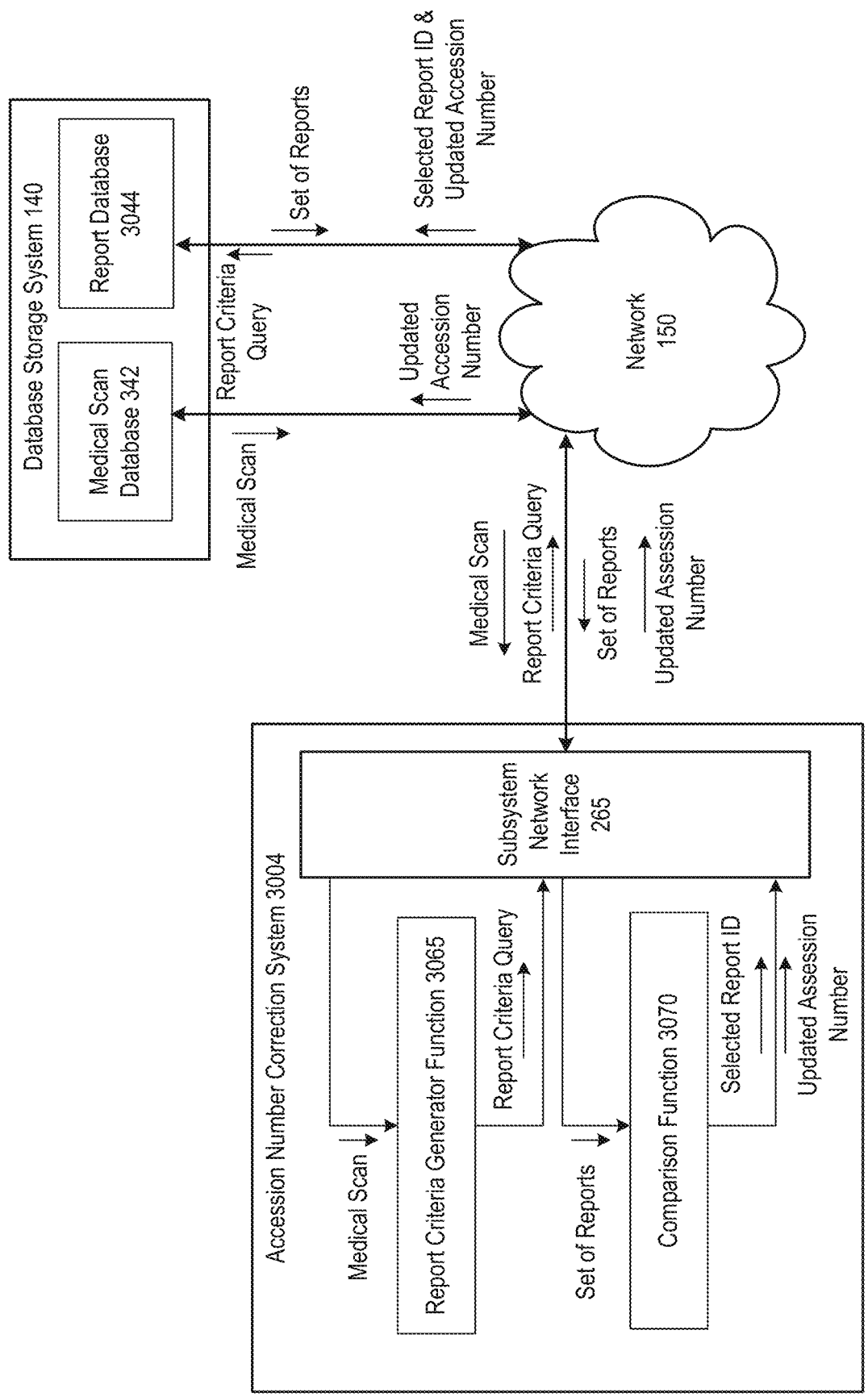
Figure 13B:
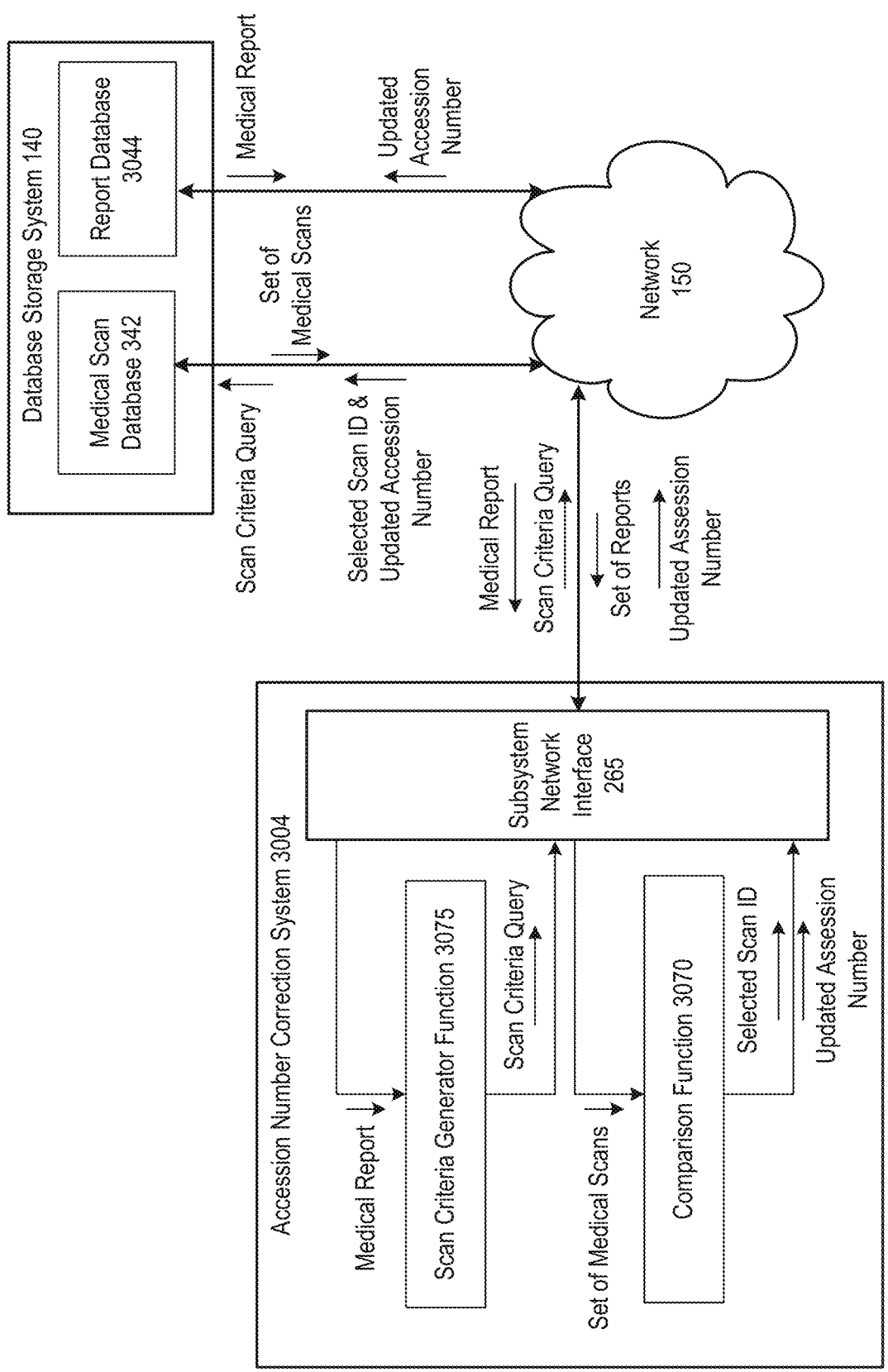
Figure 14A:
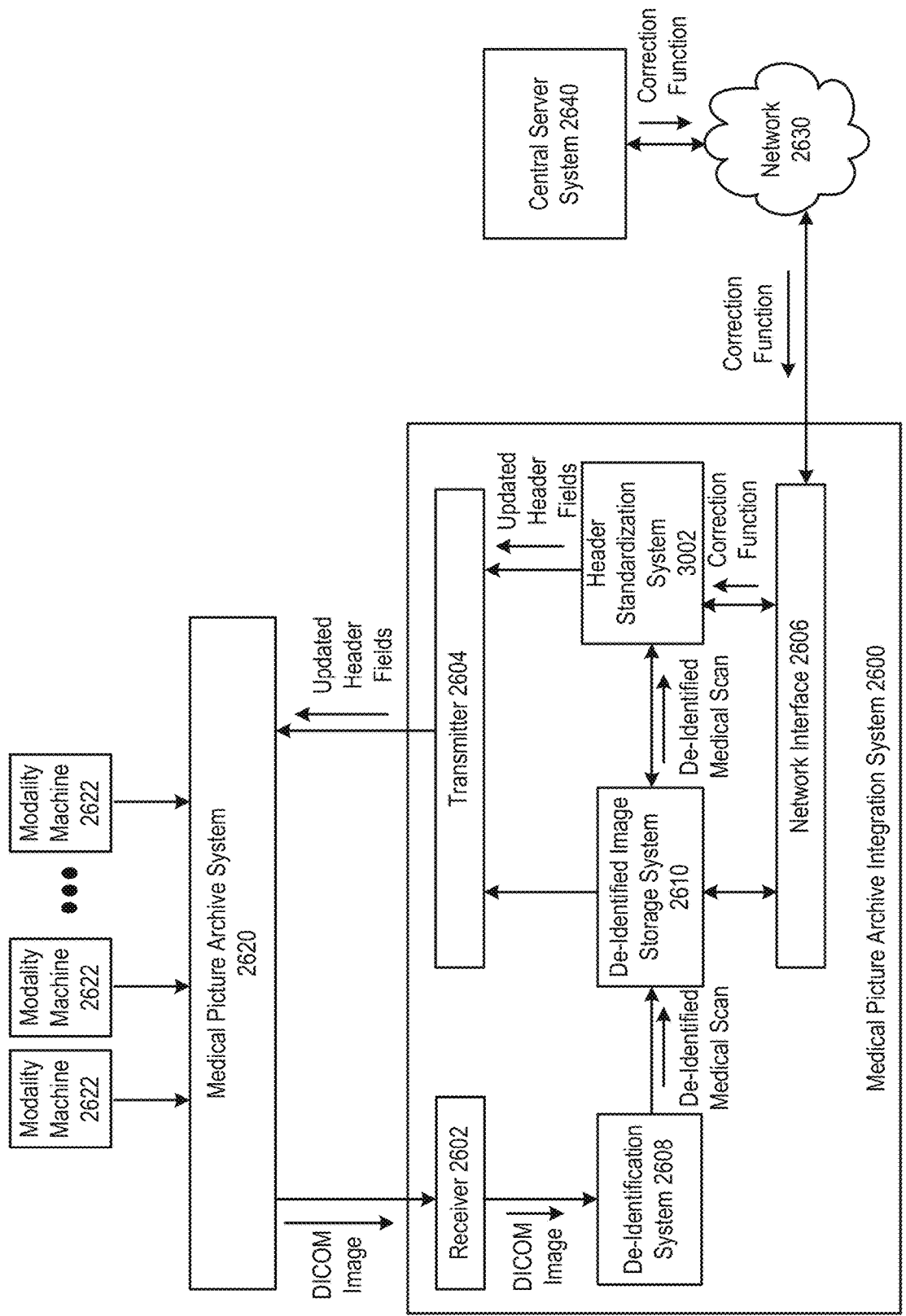
Figure 14B:
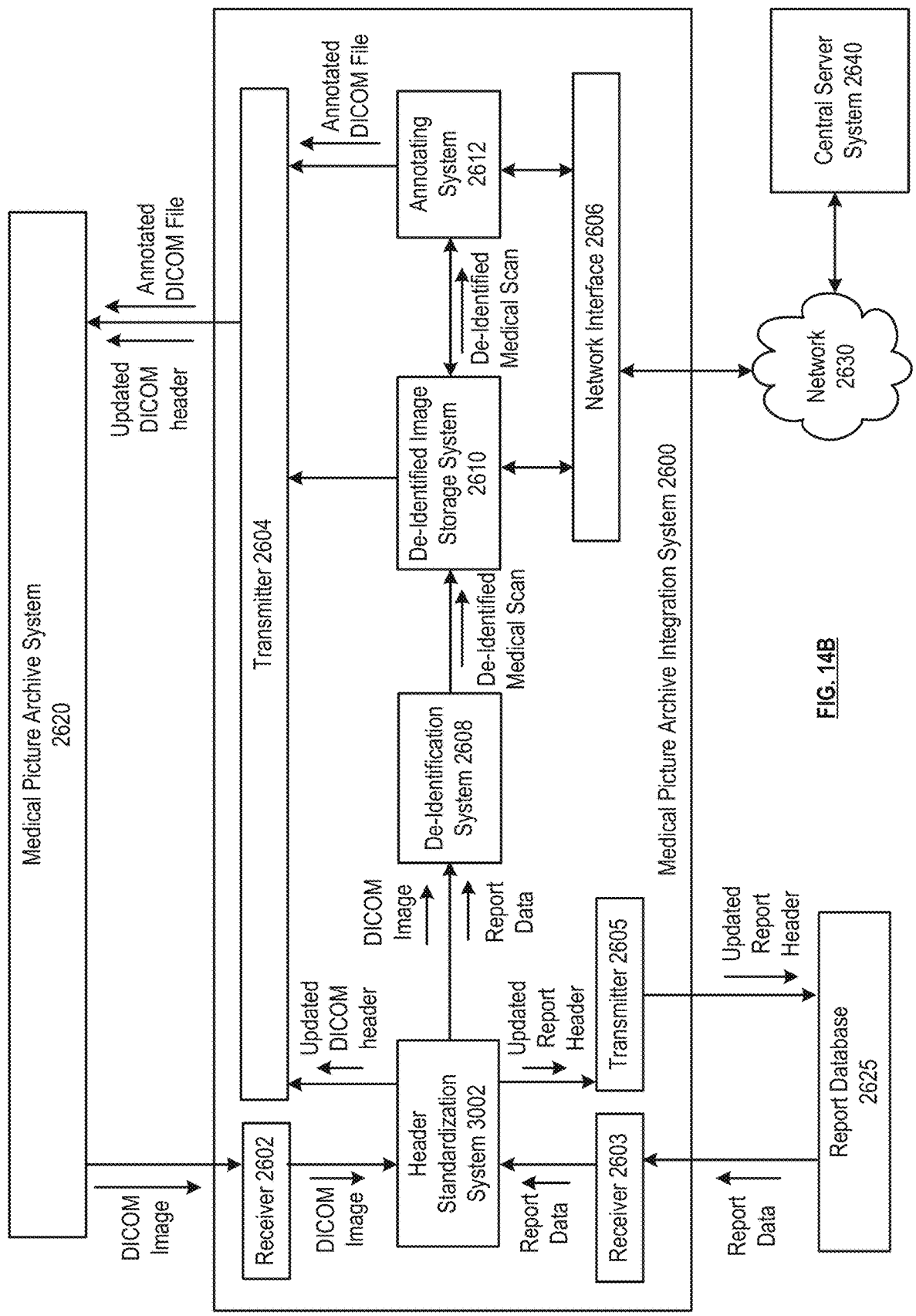
Figure 15A:
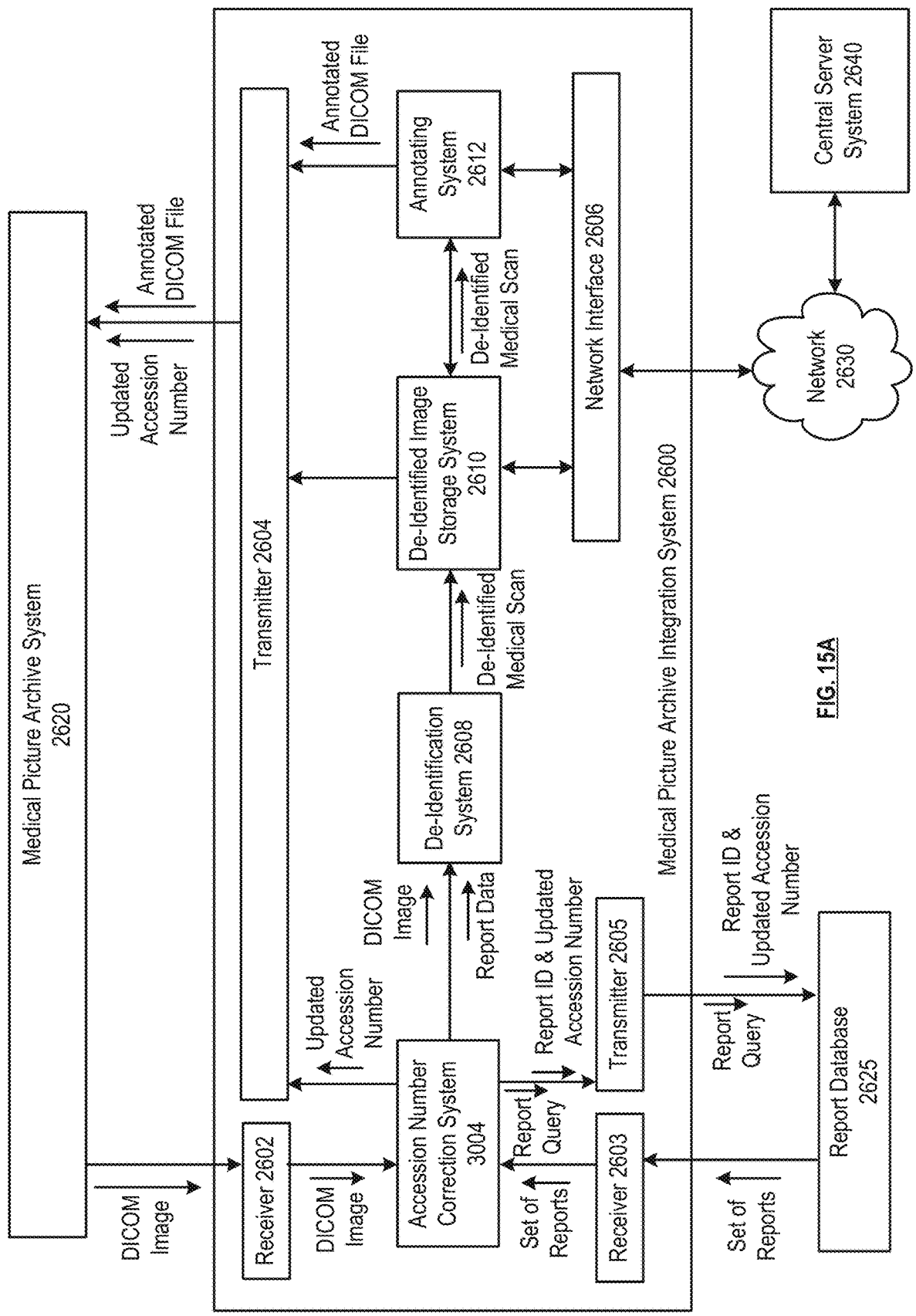
Figure 15B:
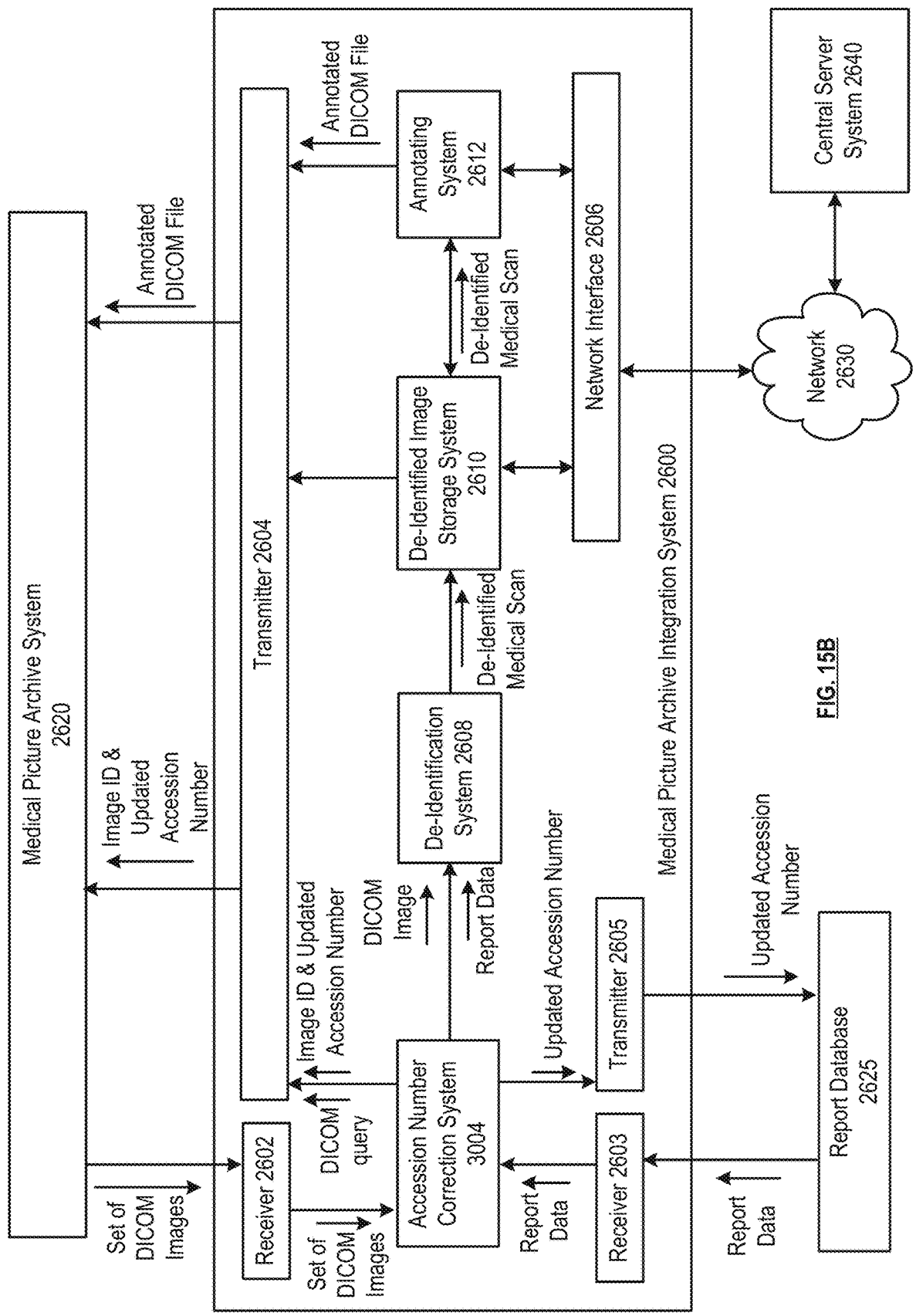
Figure 16:
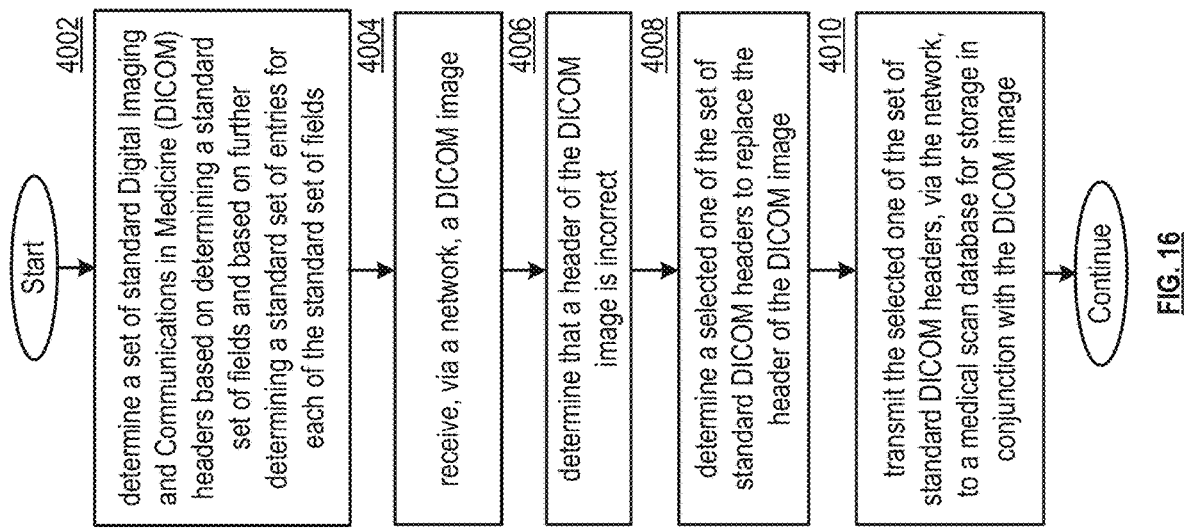
Figure 17A:
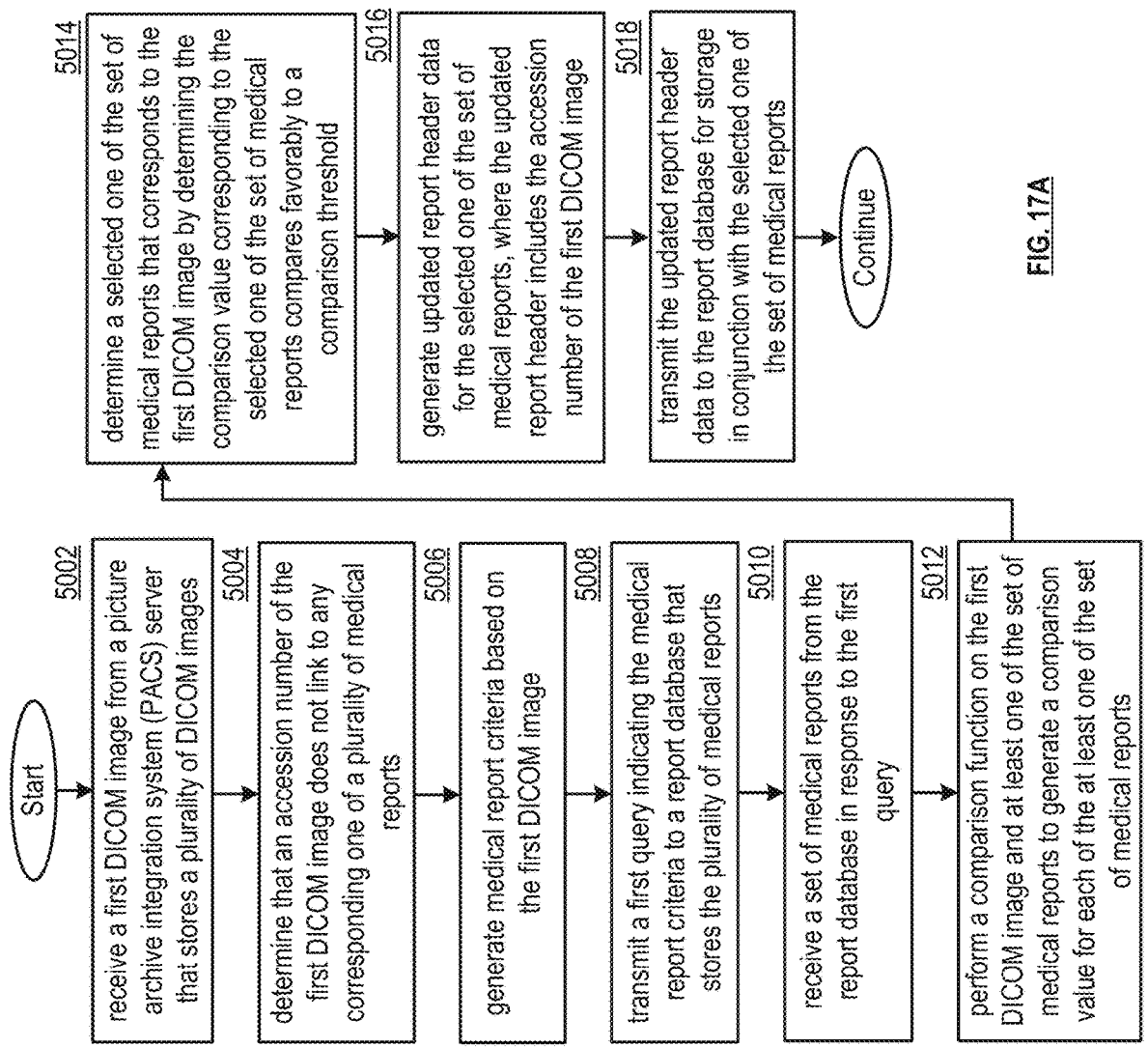
Figure 17B:
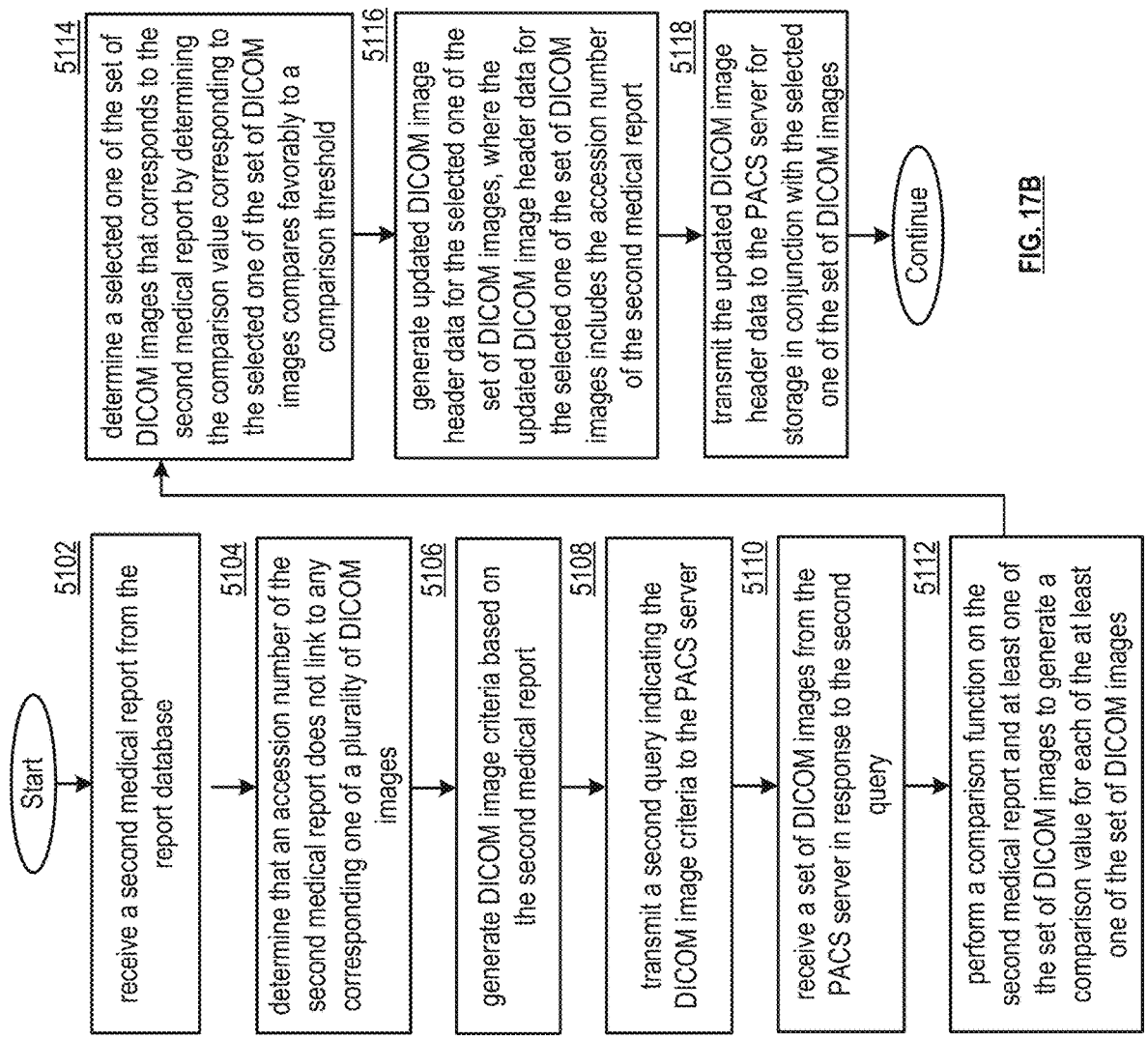
Figure 17C:
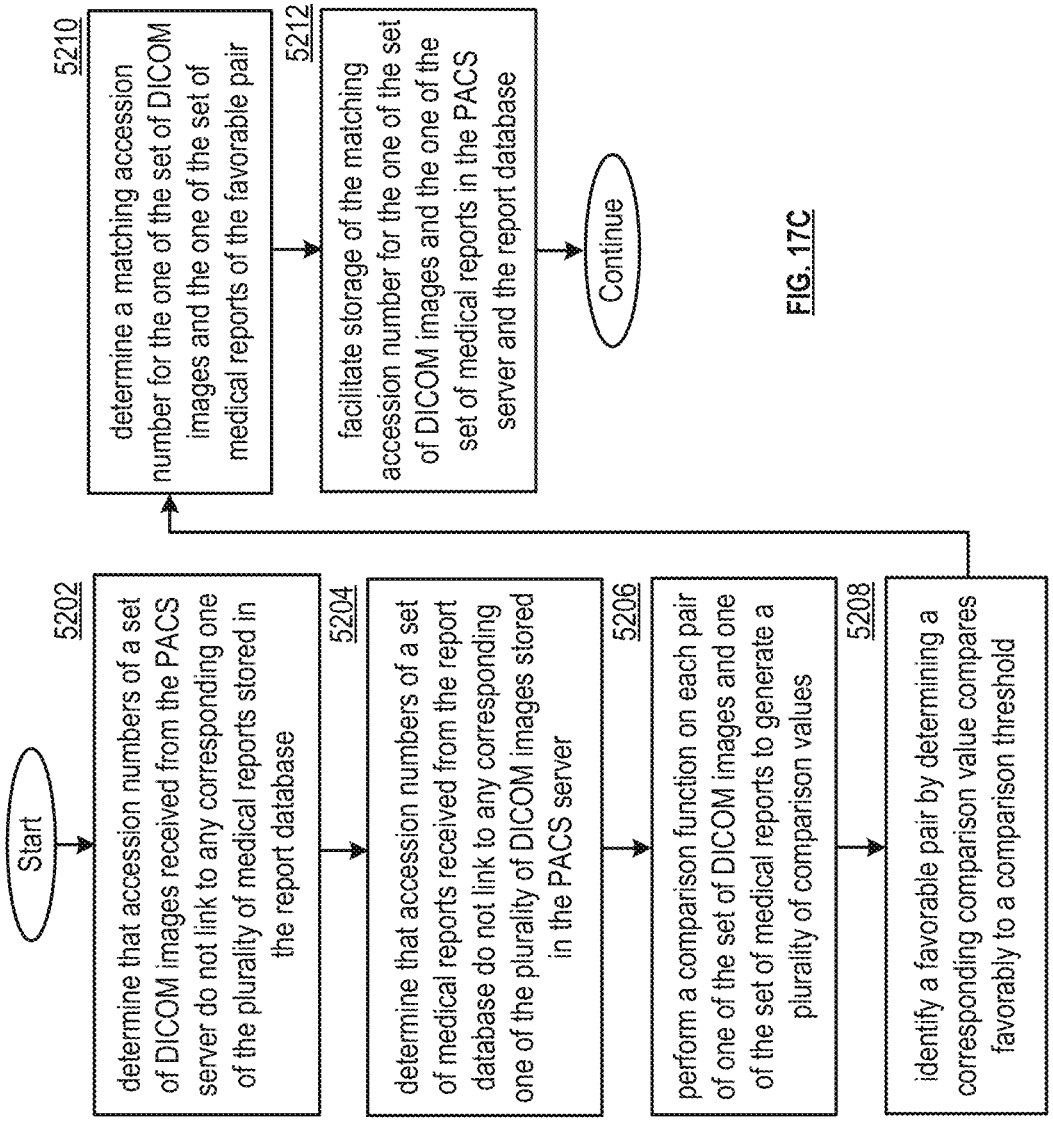

FIG. 11 presents a flowchart illustrating a method for execution by a de-identification system in accordance with various embodiments;

FIGS. 12A-12E are schematic block diagrams of a medical scan header standardization system in accordance with various embodiments;

FIGS. 13A-13B are schematic block diagrams of a accession number correction system in accordance with various embodiments;

FIGS. 14A-14B are schematic block diagrams of a medical picture archive integration system that include a medical scan header standardization system in accordance with various embodiments;

FIGS. 15A-15B are schematic block diagrams of a medical picture archive integration system that include a accession number correction system in accordance with various embodiments;

FIG. 16 presents a flowchart illustrating a method for execution by a medical scan header standardization system in accordance with various embodiments; and FIGS. 17A-17C each present a flowchart illustrating a method for execution by an accession number correction system in accordance with various embodiments.

DETAILED DESCRIPTION

The present U.S. Utility patent application is related to U.S. Utility application Ser. No. 15/627,644, entitled "MEDICAL SCAN ASSISTED REVIEW SYSTEM", filed 20 Jun. 2017, which claims priority pursuant to 35 U.S.C. § 119(e) to U.S. Provisional Application No. 62/511,150, entitled "MEDICAL SCAN ASSISTED REVIEW SYSTEM AND METHODS", filed 25 May 2017, both of which are hereby incorporated herein by reference in their entirety and made part of the present U.S. Utility patent application for all purposes.

Figure 1:
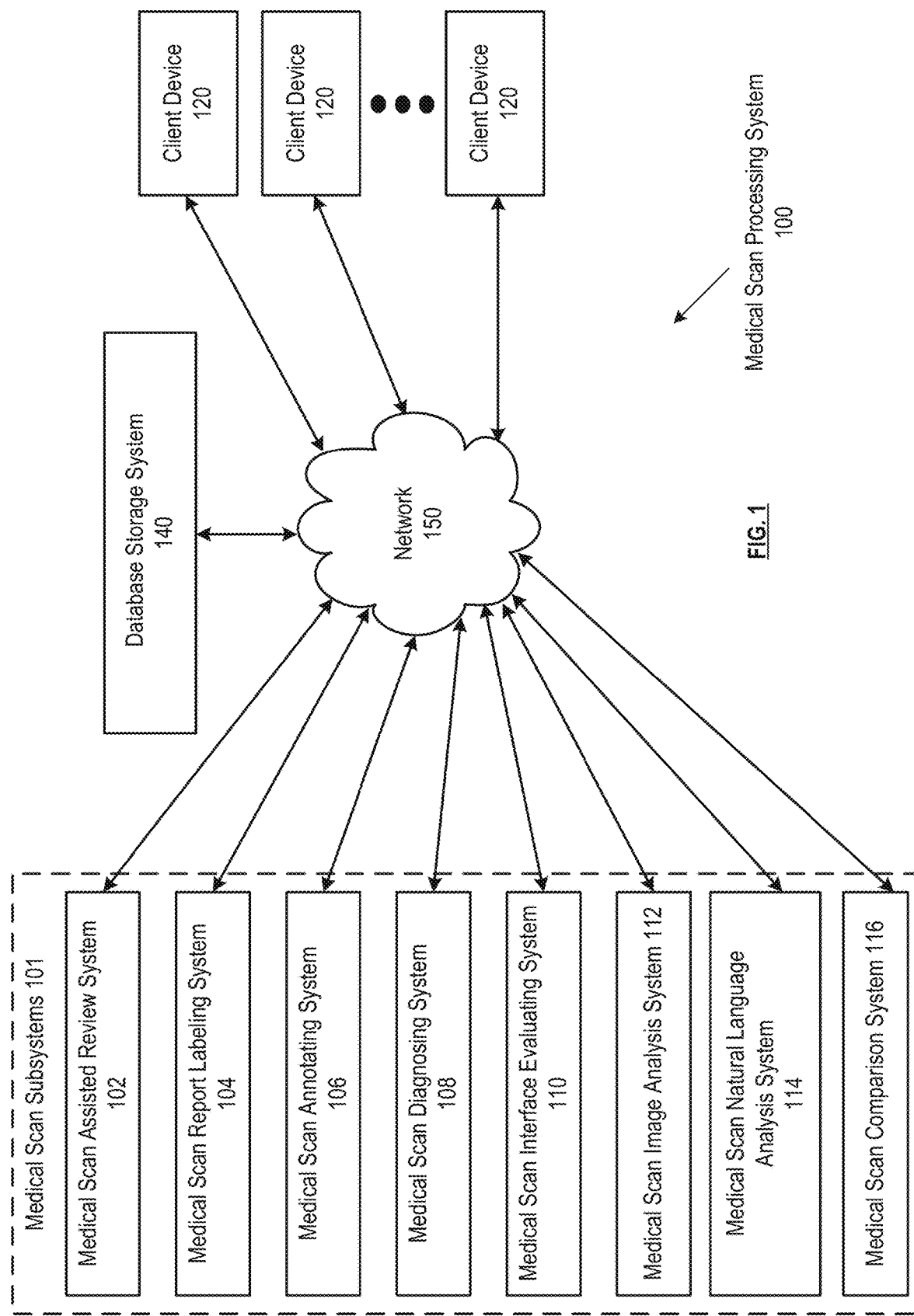
FIG. 1 is a schematic block diagram of an embodiment of a medical scan processing system.

FIG. 1 presents a medical scan processing system 100, which can include one or more medical scan subsystems 101 that communicate bidirectionally with one or more client devices 120 via a wired and/or wireless network 150. The medical scan subsystems 101 can include a medical scan assisted review system 102, medical scan report labeling system 104, a medical scan annotator system 106, a medical scan diagnosing system 108, a medical scan interface feature evaluator system 110, a medical scan image analysis system 112, a medical scan natural language analysis system 114, and/or a medical scan comparison system 116. Some or all of the subsystems 101 can utilize the same processing devices, memory devices, and/or network interfaces, for example, running on a same set of shared servers connected to network 150. Alternatively or in addition, some or all of the subsystems 101 be assigned their own processing devices, memory devices, and/or network interfaces, for example, running separately on different sets of servers connected to network 150. Some or all of the subsystems 101 can interact directly with each other, for example, where one subsystem's output is transmitted directly as input to another subsystem via network 150. Network 150 can include one or more wireless and/or wired communication systems; one or more non-public intranet systems and/or public internet systems; and/or one or more local area networks (LAN) and/or wide area networks (WAN).

The medical scan processing system 100 can further include a database storage system 140, which can include one or more servers, one or more memory devices of one or more subsystems 101, and/or one or more other memory devices connected to network 150. The database storage system 140 can store one or more shared databases and/or one or more files stored on one or more memory devices that include database entries as described herein. The shared databases and/or files can each be utilized by some or all of the subsystems of the medical scan processing system, allowing some or all of the subsystems and/or client devices to retrieve, edit, add, or delete entries to the one or more databases and/or files.

The one or more client devices 120 can each be associated with one or more users of one or more subsystems of the medical scan processing system. Some or all of the client devices can be associated with hospitals or other medical institutions and/or associated with medical professionals, employees, or other individual users for example, located at one or more of the medical institutions. Some of the client devices 120 can correspond to one or more administrators of one or more subsystems of the medical scan processing system, allowing administrators to manage, supervise, or override functions of one or more subsystems for which they are responsible.

Some or all of the subsystems 101 of the medical scan processing system 100 can include a server that presents a website for operation via a browser of client devices 120. Alternatively or in addition, each client device can store application data corresponding to some or all subsystems, for example, a subset of the subsystems that are relevant to the user in a memory of the client device, and a processor of the client device can display the interactive interface based on instructions in the interface data stored in memory. For example, the website presented by a subsystem can operate via the application. Some or all of the websites presented can correspond to multiple subsystems, for example, where the multiple subsystems share the server presenting the website. Furthermore, the network 150 can be configured for secure and/or authenticated communications between the medical scan subsystems 101, the client devices 120 and the database storage system 140 to protect the data stored in the database storage system and the data communicated between the medical scan subsystems 101, the client devices 120 and the database storage system 140 from unauthorized access.

The medical scan assisted review system 102 can be used to aid medical professionals or other users in diagnosing, triaging, classifying, ranking, and/or otherwise reviewing medical scans by presenting a medical scan for review by a user by transmitting medical scan data of a selected medical scan and/or interface feature data of selected interface features of to a client device 120 corresponding to a user of the medical scan assisted review system for display via a display device of the client device. The medical scan assisted review system 102 can generate scan review data for a medical scan based on user input to the interactive interface displayed by the display device in response to prompts to provide the scan review data, for example, where the prompts correspond to one or more interface features.

The medical scan assisted review system 102 can be operable to receive, via a network, a medical scan for review. Abnormality annotation data can be generated by identifying one or more of abnormalities in the medical scan by utilizing a computer vision model that is trained on a plurality of training medical scans. The abnormality annotation data can include location data and classification data for each of the plurality of abnormalities and/or data that facilitates the visualization of the abnormalities in the scan image data. Report data including text describing each of the plurality of abnormalities is generated based on the abnormality data. The visualization and the report data, which can collectively be displayed annotation data, can be transmitted to a client device. A display device associated with the client device can display the visualization in conjunction with the medical scan via an interactive interface, and the display device can further display the report data via the interactive interface.

In various embodiments, longitudinal data, such as one or more additional scans of longitudinal data 433 of the medical scan or of similar scans, can be displayed in conjunction with the medical scan automatically, or in response to the user electing to view longitudinal data via user input. For example, the medical scan assisted review system can retrieve a previous scan or a future scan for the patient from a patient database or from the medical scan database automatically or in response to the user electing to view past patient data. One or more previous scans can be displayed in one or more corresponding windows adjacent to the current medical scan. For example, the user can select a past scan from the longitudinal data for display. Alternatively or in addition, the user can elect longitudinal parameters such as amount of time elapsed, scan type, electing to select the most recent and/or least recent scan, electing to select a future scan, electing to select a scan at a date closest to the scan, or other criteria, and the medical scan assisted review system can automatically select a previous scan that compares most favorably to the longitudinal parameters. The selected additional scan can be displayed in an adjacent window alongside the current medical scan. In some embodiments, multiple additional scans will be selected and can be displayed in multiple adjacent windows.

In various embodiments, a first window displaying an image slice 412 of the medical scan and an adjacent second window displaying an image slice of a selected additional scan will display image slices 412 determined to correspond with the currently displayed slice 412 of the medical scan. As described with respect to selecting a slice of a selected similar medical scan for display, this can be achieved based on selecting the image slice with a matching slice number, based on automatically determining the image slice that most closely matches the anatomical region corresponding to the currently displayed slice of the current scan, and/or based on determining the slice in the previous scan with the most similar view of the abnormality as the currently displayed slice. The user can use a single scroll bar or other single user input indication to jump to a different image slice, and the multiple windows can simultaneously display the same numbered image slice, or can scroll or jump by the same number of slices if different slice numbers are initially displayed. In some embodiments, three or more adjacent windows corresponding to the medical scan and two or more additional scans are displayed, and can all be controlled with the single scroll bar in a similar fashion.

The medical scan assisted review system 102 can automatically detect previous states of the identified abnormalities based on the abnormality data, such as the abnormality location data. The detected previous states of the identified abnormality can be circled, highlighted, or otherwise indicated in their corresponding window. The medical scan assisted review system 102 can retrieve classification data for the previous state of the abnormality by retrieving abnormality annotation data 442 of the similar abnormality mapped to the previous scan from the medical scan database 342. This data may not be assigned to the previous scan, and the medical scan assisted review system can automatically determine classification or other diagnosis data for the previous medical scan by utilizing the medical scan image analysis system as discussed. Alternatively or in addition, some or all of the abnormality classification data 445 or other diagnosis data 440 for the previous scan can be assigned values determined based on the abnormality classification data or other diagnosis data determined for the current scan. Such abnormality classification data 445 or other diagnosis data 440 determined for the previous scan can be mapped to the previous scan, and or mapped to the longitudinal data 433, in the database and/or transmitted to a responsible entity via the network.

The medical assisted review system can automatically generate state change data such as a change in size, volume, malignancy, or other changes to various classifiers of the abnormality. This can be achieved by automatically comparing image data of one or more previous scans and the current scan and/or by comparing abnormality data of the previous scan to abnormality data of the current scan. In some embodiments, such metrics can be calculated by utilizing the medical scan similarity analysis function, for example, where the output of the medical scan similarity analysis function such as the similarity score indicates distance, error, or other measured discrepancy in one or more abnormality classifier categories 444 and/or abnormality pattern categories 446. This calculated distance, error, or other measured discrepancy in each category can be used to quantify state change data, indicate a new classifier in one or more categories, to determine if a certain category has become more or less severe, or otherwise determine how the abnormality has changed over time. In various embodiments, this data can be displayed in one window, for example, where an increase in abnormality size is indicated by overlaying or highlighting an outline of the current abnormality over the corresponding image slice of the previous abnormality, or vice versa. In various embodiments where several past scans are available, such state change data can be determined over time, and statistical data showing growth rate changes over time or malignancy changes over time can be generated, for example, indicating if a growth rate is lessening or worsening over time. Image slices corresponding to multiple past scans can be displayed in sequence, for example, where a first scroll bar allows a user to scroll between image slice numbers, and a second scroll bar allows a user to scroll between the same image slice over time. In various embodiments the abnormality data, heat map data, or other interface features will be displayed in conjunction with the image slices of the past image data.

The medical scan report labeling system 104 can be used to automatically assign medical codes to medical scans based on user identified keywords, phrases, or other relevant medical condition terms of natural text data in a medical scan report of the medical scan, identified by users of the medical scan report labeling system 104. The medical scan report labeling system 104 can be operable to transmit a medical report that includes natural language text to a first client device for display. Identified medical condition term data can be received from the first client device in response. An alias mapping pair in a medical label alias database can be identified by determining that a medical condition term of the alias mapping pair compares favorably to the identified medical condition term data. A medical code that corresponds to the alias mapping pair and a medical scan that corresponds to the medical report can be transmitted to a second client device of an expert user for display, and accuracy data can be received from the second client device in response. The medical code is mapped to the first medical scan in a medical scan database when the accuracy data indicates that the medical code compares favorably to the medical scan.

The medical scan annotator system 106 can be used to gather annotations of medical scans based on review of the medical scan image data by users of the system such as radiologists or other medical professionals. Medical scans that require annotation, for example, that have been triaged from a hospital or other triaging entity, can be sent to multiple users selected by the medical scan annotator system 106, and the annotations received from the multiple medical professionals can be processed automatically by a processing system of the medical scan annotator system, allowing the medical scan annotator system to automatically determine a consensus annotation of each medical scan. Furthermore, the users can be automatically scored by the medical scan annotator system based on how closely their annotation matches to the consensus annotation or some other truth annotation, for example, corresponding to annotations of the medical scan assigned a truth flag. Users can be assigned automatically to annotate subsequent incoming medical scans based on their overall scores and/or based on categorized scores that correspond to an identified category of the incoming medical scan.

The medical scan annotator system 106 can be operable to select a medical scan for transmission via a network to a first client device and a second client device for display via an interactive interface, and annotation data can be received from the first client device and the second client device in response. Annotation similarity data can be generated by comparing the first annotation data to the second annotation data, and consensus annotation data can be generated based on the first annotation data and the second annotation data in response to the annotation similarity data indicating that the difference between the first annotation data and the second annotation data compares favorably to an annotation discrepancy threshold. The consensus annotation data can be mapped to the medical scan in a medical scan database.

A medical scan diagnosing system 108 can be used by hospitals, medical professionals, or other medical entities to automatically produce inference data for given medical scans by utilizing computer vision techniques and/or natural language processing techniques. This automatically generated inference data can be used to generate and/or update diagnosis data or other corresponding data of corresponding medical scan entries in a medical scan database. The medical scan diagnosing system can utilize a medical scan database, user database, and/or a medical scan analysis function database by communicating with the database storage system 140 via the network 150, and/or can utilize another medical scan database, user database, and/or function database stored in local memory.

The medical scan diagnosing system 108 can be operable to receive a medical scan. Diagnosis data of the medical scan can be generated by performing a medical scan inference function on the medical scan. The first medical scan can be transmitted to a first client device associated with a user of the medical scan diagnosing system in response to the diagnosis data indicating that the medical scan corresponds to a non-normal diagnosis. The medical scan can be displayed to the user via an interactive interface displayed by a display device corresponding to the first client device. Review data can be received from the first client device, where the review data is generated by the first client device in response to a prompt via the interactive interface. Updated diagnosis data can be generated based on the review data. The updated diagnosis data can be transmitted to a second client device associated with a requesting entity.

A medical scan interface feature evaluating system 110 can be used evaluate proposed interface features or currently used interface features of an interactive interface to present medical scans for review by medical professionals or other users of one or more subsystems 101. The medical scan interface feature evaluator system 110 can be operable to generate an ordered image-to-prompt mapping by selecting a set of user interface features to be displayed with each of an ordered set of medical scans. The set of medical scans and the ordered image-to-prompt mapping can be transmitted to a set of client devices. A set of responses can be generated by each client device in response to sequentially displaying each of the set of medical scans in conjunction with a mapped user interface feature indicated in the ordered image-to-prompt mapping via a user interface. Response score data can be generated by comparing each response to truth annotation data of the corresponding medical scan. Interface feature score data corresponding to each user interface feature can be generated based on aggregating the response score data, and is used to generate a ranking of the set of user interface features.

A medical scan image analysis system 112 can be used to generate and/or perform one or more medical scan image analysis functions by utilizing a computer vision-based learning algorithm 1350 on a training set of medical scans with known annotation data, diagnosis data, labeling and/or medical code data, report data, patient history data, patient risk factor data, and/or other metadata associated with medical scans. These medical scan image analysis functions can be used to generate inference data for new medical scans that are triaged or otherwise require inferred annotation data, diagnosis data, labeling and/or medical code data, and/or report data. For example, some medical scan image analysis functions can correspond to medical scan inference functions of the medical scan diagnosing system or other medical scan analysis functions of a medical scan analysis function database. The medical scan image analysis functions can be used to determine whether or not a medical scan is normal, to detect the location of an abnormality in one or more slices of a medical scan, and/or to characterize a detected abnormality. The medical scan image analysis system can be used to generate and/or perform computer vision based medical scan image analysis functions utilized by other subsystems of the medical scan processing system as described herein, aiding medical professionals to diagnose patients and/or to generate further data and models to characterize medical scans. The medical scan image analysis system can include a processing system that includes a processor and a memory that stores executable instructions that, when executed by the processing system, facilitate performance of operations.

The medical scan image analysis system 112 can be operable to receive a plurality of medical scans that represent a three-dimensional anatomical region and include a plurality of cross-sectional image slices. A plurality of three-dimensional subregions corresponding to each of the plurality of medical scans can be generated by selecting a proper subset of the plurality of cross-sectional image slices from each medical scan, and by further selecting a two-dimensional subregion from each proper subset of cross-sectional image slices. A learning algorithm can be performed on the plurality of three-dimensional subregions to generate a neural network. Inference data corresponding to a new medical scan received via the network can be generated by performing an inference algorithm on the new medical scan by utilizing the neural network. An inferred abnormality can be identified in the new medical scan based on the inference data.

The medical scan natural language analysis system 114 can determine a training set of medical scans with medical codes determined to be truth data. Corresponding medical reports and/or other natural language text data associated with a medical scan can be utilized to train a medical scan natural language analysis function by generating a medical report natural language model. The medical scan natural language analysis function can be utilized to generate inference data for incoming medical reports for other medical scans to automatically determine corresponding medical codes, which can be mapped to corresponding medical scans. Medical codes assigned to medical scans by utilizing the medical report natural language model can be utilized by other subsystems, for example, to train other medical scan analysis functions, to be used as truth data to verify annotations provided via other subsystems, to aid in diagnosis, or otherwise be used by other subsystems as described herein.

A medical scan comparison system 116 can be utilized by one or more subsystems to identify and/or display similar medical scans, for example, to perform or determine function parameters for a medical scan similarity analysis function, to generate or retrieve similar scan data, or otherwise compare medical scan data. The medical scan comparison system 116 can also utilize some or all features of other subsystems as described herein. The medical scan comparison system 116 can be operable to receive a medical scan via a network and can generate similar scan data. The similar scan data can include a subset of medical scans from a medical scan database and can be generated by performing an abnormality similarity function, such as medical scan similarity analysis function, to determine that a set of abnormalities included in the subset of medical scans compare favorably to an abnormality identified in the medical scan. At least one cross-sectional image can be selected from each medical scan of the subset of medical scans for display on a display device associated with a user of the medical scan comparison system in conjunction with the medical scan.

Figure 2A:
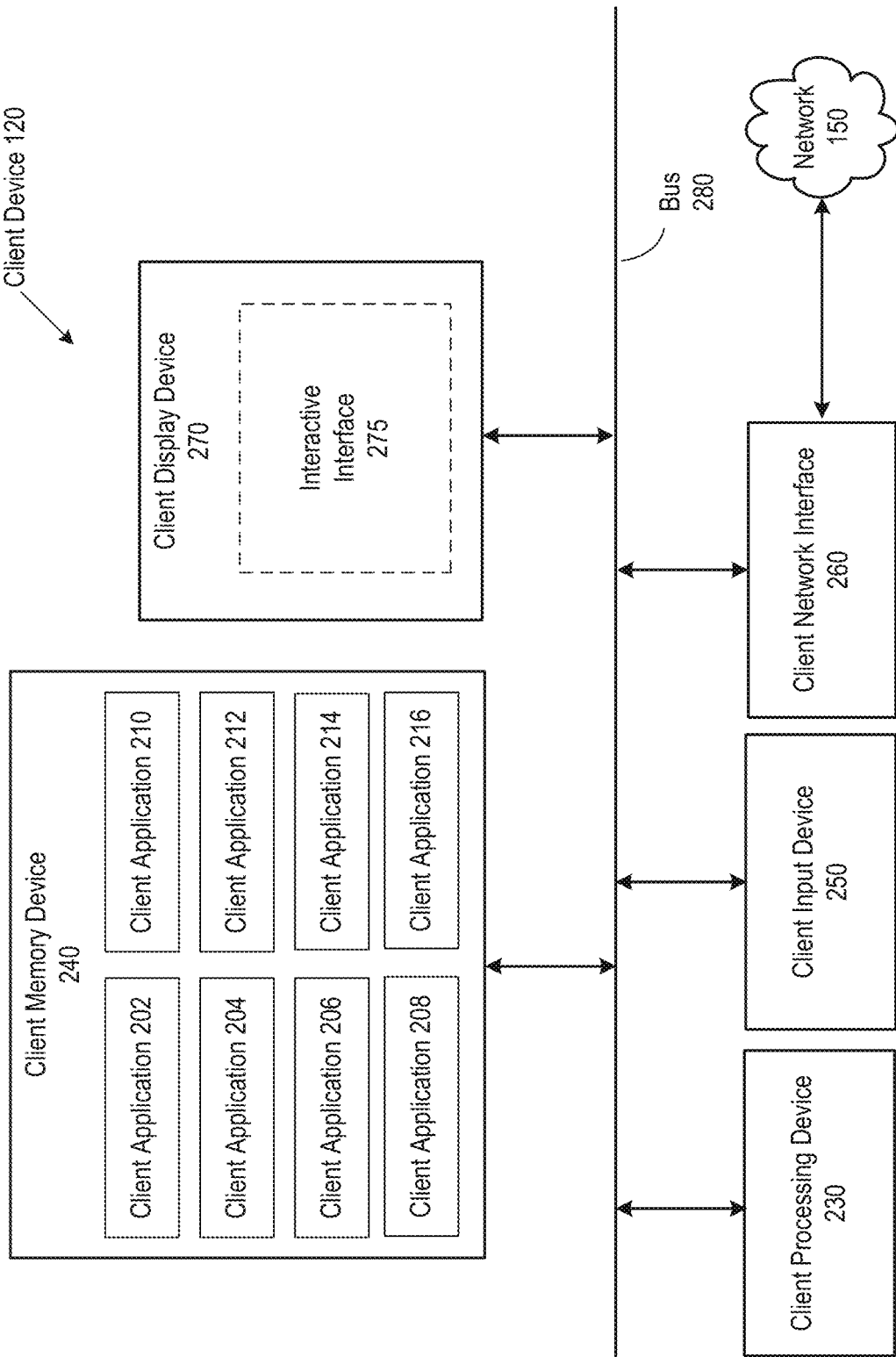
FIG. 2A is a schematic block diagram of a client device in accordance with various embodiments.

FIG. 2A presents an embodiment of client device 120. Each client device 120 can include one or more client processing devices 230, one or more client memory devices 240, one or more client input devices 250, one or more client network interfaces 260 operable to more support one or more communication links via the network 150 indirectly and/or directly, and/or one or more client display devices 270, connected via bus 280. Client applications 202, 204, 206, 208, 210, 212, 214, and/or 216 correspond to subsystems 102, 104, 106, 108, 110, 112, 114, and/or 116 of the medical scan processing system respectfully. Each client device 120 can receive the application data from the corresponding subsystem via network 150 by utilizing network interface 260, for storage in the one or more memory devices 240. In various embodiments, some or all client devices 120 can include a computing device associated with a radiologist, medical entity, or other user of one or more subsystems as described herein.

The one or more processing devices 230 can display interactive interface 275 on the one or more client display devices 270 in accordance with one or more of the client applications 202, 204, 206, 208, 210, 212, 214, and/or 216, for example, where a different interactive interface 275 is displayed for some or all of the client applications in accordance with the website presented by the corresponding subsystem 102, 104, 106, 108, 110, 112, 114 and/or 116. The user can provide input in response to menu data or other prompts presented by the interactive interface via the one or more client input devices 250, which can include a microphone, mouse, keyboard, touchscreen of display device 270 itself or other touchscreen, and/or other device allowing the user to interact with the interactive interface. The one or more processing devices 230 can process the input data and/or send raw or processed input data to the corresponding subsystem, and/or can receive and/or generate new data in response for presentation via the interactive interface 275 accordingly, by utilizing network interface 260 to communicate bidirectionally with one or more subsystems and/or databases of the medical scan processing system via network 150.

Figure 2B:
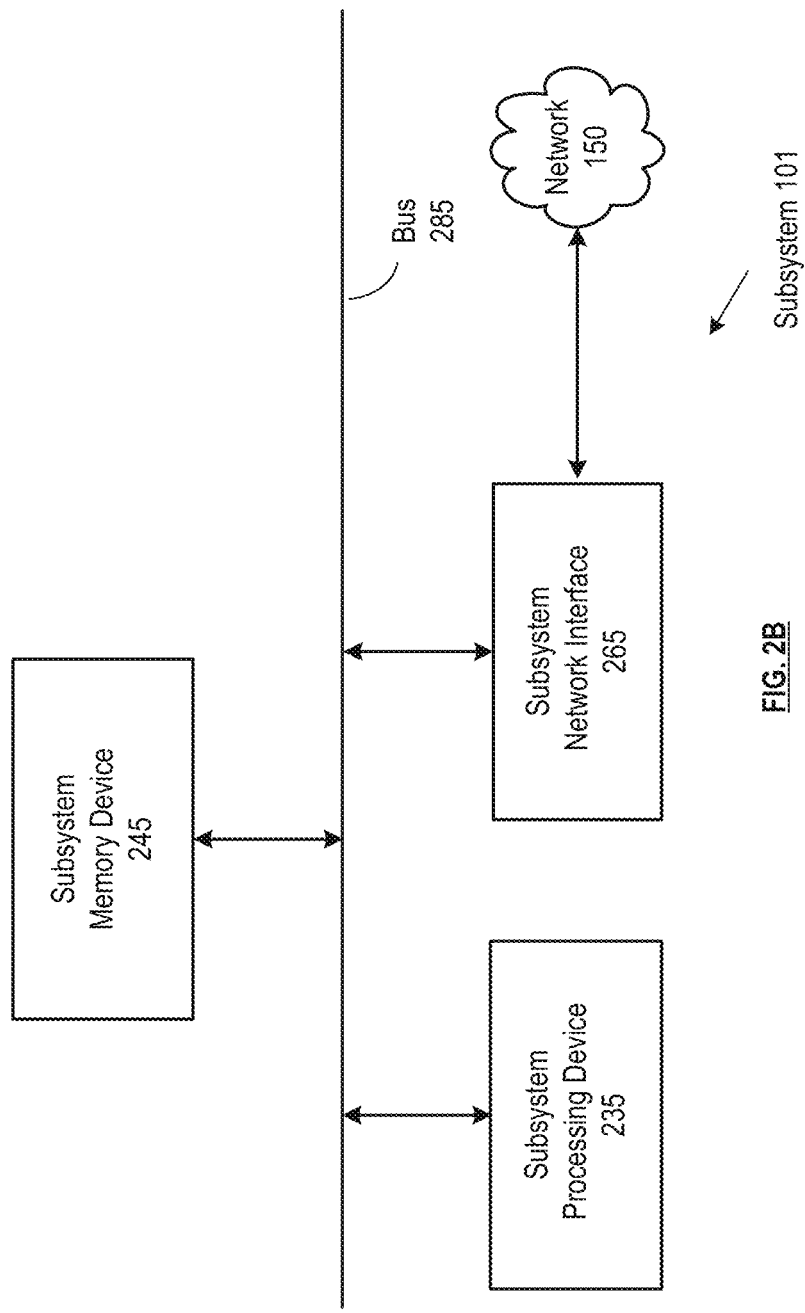
FIG. 2B is a schematic block diagram of one or more subsystems in accordance with various embodiments.

FIG. 2B presents an embodiment of a subsystem 101, which can be utilized in conjunction with subsystem 102, 104, 106, 108, 110, 112, 114 and/or 116. Each subsystem 101 can include one or more subsystem processing devices 235, one or more subsystem memory devices 245, and/or one or more subsystem network interfaces 265, connected via bus 285. The subsystem memory devices 245 can store executable instructions that, when executed by the one or more subsystem processing devices 235, facilitate performance of operations by the subsystem 101, as described for each subsystem herein.

Figure 3:
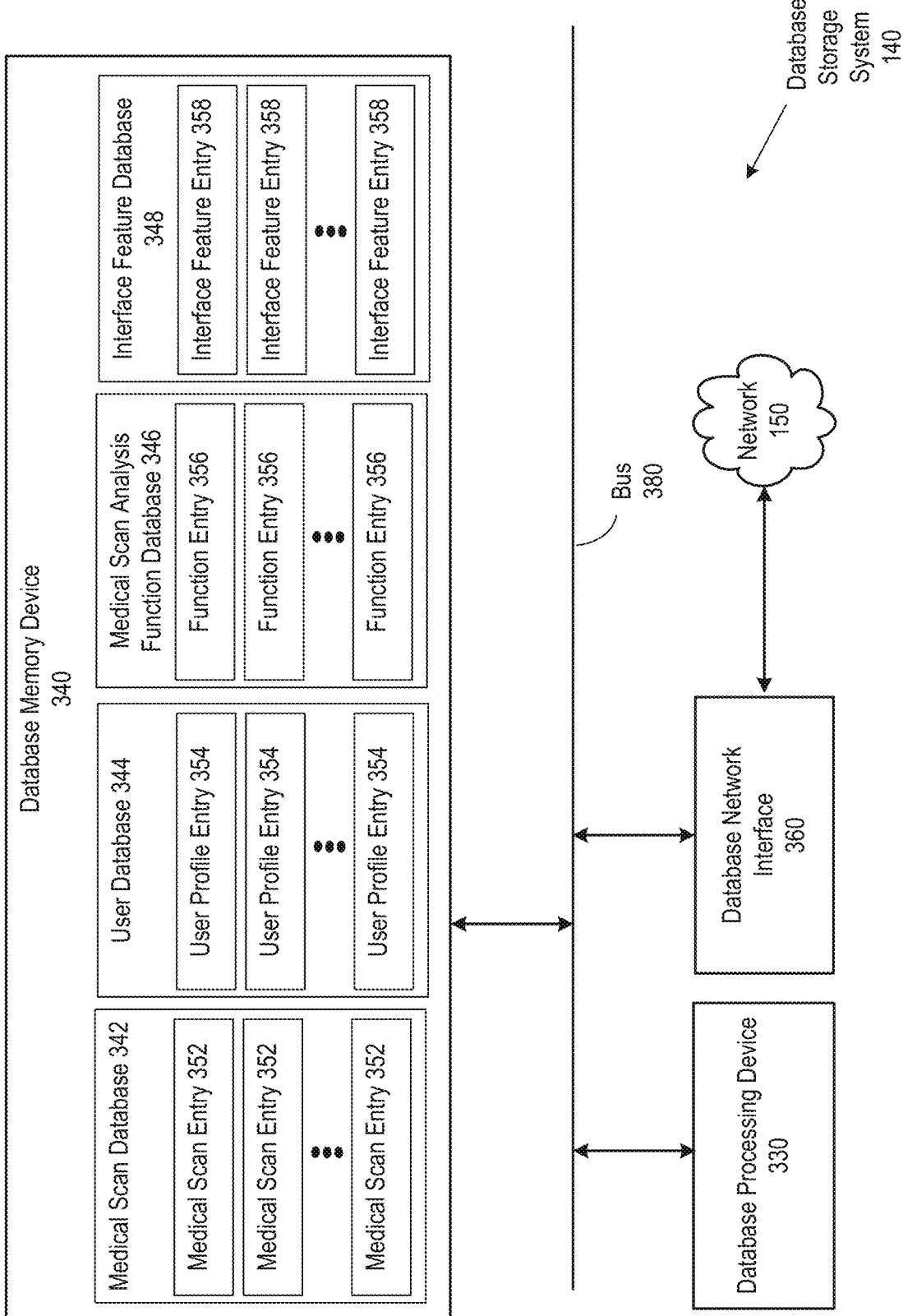
FIG. 3 is a schematic block diagram of a database storage system in accordance with various embodiments.

FIG. 3 presents an embodiment of the database storage system 140. Database storage system 140 can include at least one database processing device 330, at least one database memory device 340, and at least one database network interface 360, operable to more support one or more communication links via the network 150 indirectly and/or directly, all connected via bus 380. The database storage system 140 can store one or more databases the at least one memory 340, which can include a medical scan database 342 that includes a plurality medical scan entries 352, a user database 344 that includes a plurality of user profile entries 354, a medical scan analysis function database 346 that includes a plurality of medical scan analysis function entries 356, an interface feature database 348 can include a plurality of interface feature entries 358, and/or other databases that store data generated and/or utilized by the subsystems 101. Some or all of the databases 342, 344, 346 and/or 348 can consist of multiple databases, can be stored relationally or non-relationally, and can include different types of entries and different mappings than those described herein. A database entry can include an entry in a relational table or entry in a non-relational structure. Some or all of the data attributes of an entry 352, 354, 356, and/or 358 can refer to data included in the entry itself or that is otherwise mapped to an identifier included in the entry and can be retrieved from, added to, modified, or deleted from the database storage system 140 based on a given identifier of the entry. Some or all of the databases 342, 344, 346, and/or 348 can instead be stored locally by a corresponding subsystem, for example, if they are utilized by only one subsystem.

The processing device 330 can facilitate read/write requests received from subsystems and/or client devices via the network 150 based on read/write permissions for each database stored in the at least one memory device 340. Different subsystems can be assigned different read/write permissions for each database based on the functions of the subsystem, and different client devices 120 can be assigned different read/write permissions for each database. One or more client devices 120 can correspond to one or more administrators of one or more of the databases stored by the database storage system, and database administrator devices can manage one or more assigned databases, supervise assess and/or efficiency, edit permissions, or otherwise oversee database processes based on input to the client device via interactive interface 275.

Figure 4A:
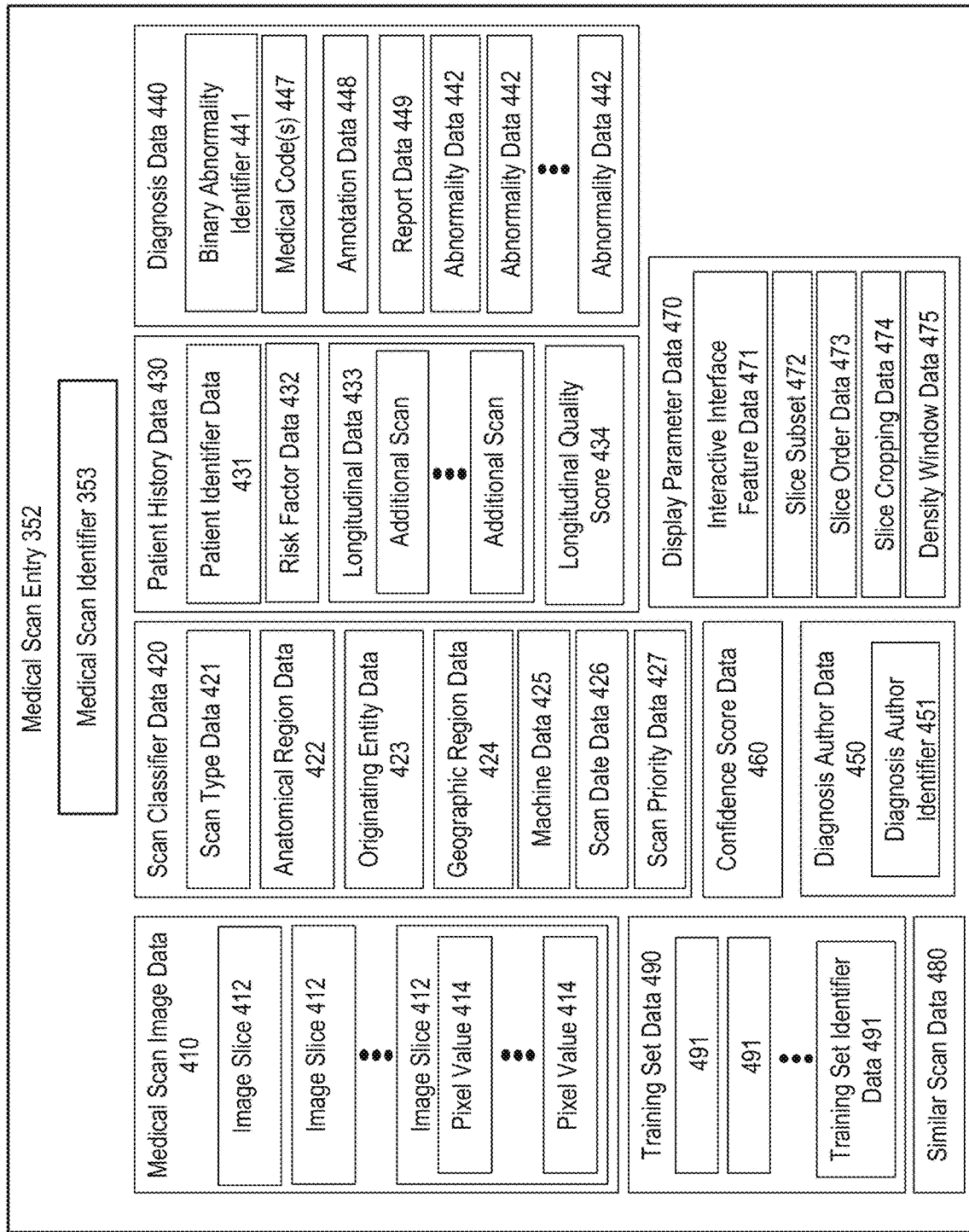
FIG. 4A is schematic block diagram of a medical scan entry in accordance with various embodiments.

FIG. 4A presents an embodiment of a medical scan entry 352, stored in medical scan database 342, included in metadata of a medical scan, and/or otherwise associated with a medical scan. A medical scan can include imaging data corresponding to a CT scan, x-ray, MM, PET scan, Ultrasound, EEG, mammogram, or other type of radiological scan or medical scan taken of an anatomical region of a human body, animal, organism, or object and further can include metadata corresponding to the imaging data. Some or all of the medical scan entries can be formatted in accordance with a Digital Imaging and Communications in Medicine (DICOM) format or other standardized image format, and some or more of the fields of the medical scan entry 352 can be included in a DICOM header or other standardized header of the medical scan. Medical scans can be awaiting review or can have already been reviewed by one or more users or automatic processes and can include tentative diagnosis data automatically generated by a subsystem, generated based on user input, and/or generated from another source. Some medical scans can include final, known diagnosis data generated by a subsystem and/or generated based on user input, and/or generated from another source, and can included in training sets used to train processes used by one or more subsystems such as the medical scan image analysis system 112 and/or the medical scan natural language analysis system 114.

Some medical scans can include one or more abnormalities, which can be identified by a user or can be identified automatically. Abnormalities can include nodules, for example malignant nodules identified in a chest CT scan. Abnormalities can also include and/or be characterized by one or more abnormality pattern categories such as such as cardiomegaly, consolidation, effusion, emphysema, and/or fracture, for example identified in a chest x-ray. Abnormalities can also include any other unknown, malignant or benign feature of a medical scan identified as not normal. Some scans can contain zero abnormalities, and can be identified as normal scans. Some scans identified as normal scans can include identified abnormalities that are classified as benign, and include zero abnormalities classified as either unknown or malignant. Scans identified as normal scans may include abnormalities that were not detected by one or more subsystems and/or by an originating entity. Thus, some scans may be improperly identified as normal. Similarly, scans identified to include at least one abnormality may include at least one abnormality that was improperly detected as an abnormality by one or more subsystems and/or by an originating entity. Thus, some scans may be improperly identified as containing abnormalities.

Each medical scan entry 352 can be identified by its own medical scan identifier 353, and can include or otherwise map to medical scan image data 410, and metadata such as scan classifier data 420, patient history data 430, diagnosis data 440, annotation author data 450, confidence score data 460, display parameter data 470, similar scan data 480, training set data 490, and/or other data relating to the medical scan. Some or all of the data included in a medical scan entry 352 can be used to aid a user in generating or editing diagnosis data 440, for example, in conjunction with the medical scan assisted review system 102, the medical scan report labeling system 104, and/or the medical scan annotator system 106. Some or all of the data included in a medical scan entry 352 can be used to allow one or more subsystems 101, such as automated portions of the medical scan report labeling system 104 and/or the medical scan diagnosing system 108, to automatically generate and/or edit diagnosis data 440 or other data the medical scan. Some or all of the data included in a medical scan entry 352 can be used to train some or all medical scan analysis functions of the medical scan analysis function database 346 such as one or more medical scan image analysis functions, one or more medical scan natural language analysis functions, one or more medical scan similarity analysis functions, one or more medical report generator functions, and/or one or more medical report analysis functions, for example, in conjunction with the medical scan image analysis system 112, the medical scan natural language analysis system 114, and/or the medical scan comparison system 116.

The medical scan entries 352 and the associated data as described herein can also refer to data associated with a medical scan that is not stored by the medical scan database, for example, that is uploaded by a client device for direct transmission to a subsystem, data generated by a subsystem and used as input to another subsystem or transmitted directly to a client device, data stored by a Picture Archive and Communication System (PACS) communicating with the medical scan processing system 100, or other data associated with a medical scan that is received and or generated without being stored in the medical scan database 342. For example, some or all of the structure and data attributes described with respect to a medical scan entry 352 can also correspond to structure and/or data attribute of data objects or other data generated by and/or transmitted between subsystems and/or client devices that correspond to a medical scan. Herein, any of the data attributes described with respect to a medical scan entry 352 can also correspond to data extracted from a data object generated by a subsystem or client device or data otherwise received from a subsystem, client device, or other source via network 150 that corresponds to a medical scan.

The medical scan image data 410 can include one or more images corresponding to a medical scan. The medical scan image data 410 can include one or more image slices 412, for example, corresponding to a single x-ray image, a plurality of cross-sectional, tomographic images of a scan such as a CT scan, or any plurality of images taken from the same or different point at the same or different angles. The medical scan image data 410 can also indicate an ordering of the one or more image slices 412. Herein, a "medical scan" can refer a full scan of any type represented by medical scan image data 410. Herein, an "image slice" can refer to one of a plurality of cross-sectional images of the medical scan image data 410, one of a plurality of images taken from different angles of the medical scan image data 410, and/or the single image of the medical scan image data 410 that includes only one image. Furthermore "plurality of image slices" can refer to all of the images of the associated medical scan, and refers to only a single image if the medical scan image data 410 includes only one image. Each image slice 412 can include a plurality of pixel values 414 mapped to each pixel of the image slice. Each pixel value can correspond to a density value, such as a Hounsfield value or other measure of density. Pixel values can also correspond to a grayscale value, a RGB (Red-Green-Blue) or other color value, or other data stored by each pixel of an image slice 412.

Scan classifier data 420 can indicate classifying data of the medical scan. Scan classifier data can include scan type data 421, for example, indicating the modality of the scan. The scan classifier data can indicate that the scan is a CT scan, x-ray, MM, PET scan, Ultrasound, EEG, mammogram, or other type of scan. Scan classifier data 420 can also include anatomical region data 422, indicating for example, the scan is a scan of the chest, head, right knee, or other anatomical region. Scan classifier data can also include originating entity data 423, indicating the hospital where the scan was taken and/or a user that uploaded the scan to the system. If the originating entity data corresponds to a user of one or more subsystems 101, the originating entity data can include a corresponding user profile identifier and/or include other data from the user profile entry 354 of the user. Scan classifier data 420 can include geographic region data 424, indicating a city, state, and/or country from which the scan originated, for example, based on the user data retrieved from the user database 344 based on the originating entity. Scan classifier data can also include machine data 425, which can include machine identifier data, machine model data, machine calibration data, and/or contrast agent data, for example based on imaging machine data retrieved from the user database 344 based on the originating entity data 423. The scan classifier data 420 can include scan date data 426 indicating when the scan was taken. The scan classifier data 420 can include scan priority data 427, which can indicate a priority score, ranking, number in a queue, or other priority data with regard to triaging and/or review. A priority score, ranking, or queue number of the scan priority data 427 can be generated by automatically by a subsystem based on the scan priority data 427, based on a severity of patient symptoms or other indicators in the risk factor data 432, based on a priority corresponding to the originating entity, based on previously generated diagnosis data 440 for the scan, and/or can be assigned by the originating entity and/or a user of the system.

The scan classifier data 420 can include other classifying data not pictured in FIG. 4A. For example, a set of scans can include medical scan image data 410 corresponding to different imaging planes. The scan classifier data can further include imaging plane data indicating one or more imaging planes corresponding to the image data. For example, the imaging plane data can indicate the scan corresponds to the axial plane, sagittal plane, or coronal plane. A single medical scan entry 352 can include medical scan image data 410 corresponding multiple planes, and each of these planes can be tagged appropriately in the image data. In other embodiments, medical scan image data 410 corresponding to each plane can be stored as separate medical scan entries 352, for example, with a common identifier indicating these entries belong to the same set of scans.

Alternatively or in addition, the scan classifier data 420 can include sequencing data. For example, a set of scans can include medical scan image data 410 corresponding to different sequences. The scan classifier data can further include sequencing data indicating one or more of a plurality of sequences of the image data corresponds to, for example, indicating whether an MRI scan corresponds to a T2 sequence, a T1 sequence, a T1 sequence with contrast, a diffusion sequence, a FLAIR sequence, or other MM sequence. A single medical scan entry 352 can include medical scan image data 410 corresponding to multiple sequences, and each of these sequences can be tagged appropriately in the entry. In other embodiments, medical scan image data 410 corresponding to each sequence can be stored as separate medical scan entries 352, for example, with a common identifier indicating these entries belong to the same set of scans.

Alternatively or in addition, the scan classifier data 420 can include an image quality score. This score can be determined automatically by one or more subsystems 101, and/or can be manually assigned the medical scan. The image quality score can be based on a resolution of the image data 410, where higher resolution image data is assigned a more favorable image quality score than lower resolution image data. The image quality score can be based on whether the image data 410 corresponds to digitized image data received directly from the corresponding imaging machine, or corresponds to a hard copy of the image data that was later scanned in. In some embodiments, the image quality score can be based on a detected corruption, and/or detected external factor that determined to negatively affect the quality of the image data during the capturing of the medical scan and/or subsequent to the capturing of the medical scan. In some embodiments, the image quality score can be based on detected noise in the image data, where a medical scan with a higher level of detected noise can receive a less favorable image quality score than a medical scan with a lower level of detected noise. Medical scans with this determined corruption or external factor can receive a less favorable image quality score than medical scans with no detected corruption or external factor.

In some embodiments, the image quality score can be based on include machine data 425. In some embodiments, one or more subsystems can utilize the image quality score to flag medical scans with image quality scores that fall below an image quality threshold. The image quality threshold can be the same or different for different subsystems, medical scan modalities, and/or anatomical regions. For example, the medical scan image analysis system can automatically filter training sets based on selecting only medical scans with image quality scores that compare favorably to the image quality threshold. As another example, one or more subsystems can flag a particular imaging machine and/or hospital or other medical entity that have produced at least a threshold number and/or percentage of medical scan with image quality scores that compare unfavorably to the image quality threshold. As another example, a de-noising algorithm can be automatically utilized to clean the image data when the image quality score compares unfavorably to the image quality threshold. As another example, the medical scan image analysis system can select a particular medical image analysis function from a set of medical image analysis functions to utilize on a medical scan to generate inference data for the medical scan. Each of this set of medical image analysis function can be trained on different levels of image quality, and the selected image analysis function can be selected based on the determined image quality score falling within a range of image quality scores the image analysis function was trained on and/or is otherwise suitable for.

The patient history data 430 can include patient identifier data 431 which can include basic patient information such as name or an identifier that may be anonymized to protect the confidentiality of the patient, age, and/or gender. The patient identifier data 431 can also map to a patient entry in a separate patient database stored by the database storage system, or stored elsewhere. The patient history data can include patient risk factor data 432 which can include previous medical history, family medical history, smoking and/or drug habits, pack years corresponding to tobacco use, environmental exposures, patient symptoms, etc. The patient history data 430 can also include longitudinal data 433, which can identify one or more additional medical scans corresponding to the patient, for example, retrieved based on patient identifier data 431 or otherwise mapped to the patient identifier data 431. Some or all additional medical scans can be included in the medical scan database, and can be identified based on their corresponding identifiers medical scan identifiers 353. Some or all additional medical scans can be received from a different source and can otherwise be identified. Alternatively or in addition, the longitudinal data can simply include some or all relevant scan entry data of a medical scan entry 352 corresponding to the one or more additional medical scans. The additional medical scans can be the same type of scan or different types of scans. Some or all of the additional scans may correspond to past medical scans, and/or some or all of the additional scans may correspond to future medical scans. The longitudinal data 433 can also include data received and/or determined at a date after the scan such as final biopsy data, or some or all of the diagnosis data 440. The patient history data can also include a longitudinal quality score 434, which can be calculated automatically by a subsystem, for example, based on the number of additional medical scans, based on how many of the additional scans in the file were taken before and/or after the scan based on the scan date data 426 of the medical scan and the additional medical scans, based on a date range corresponding to the earliest scan and corresponding to the latest scan, based on the scan types data 421 these scans, and/or based on whether or not a biopsy or other final data is included. As used herein, a "high" longitudinal quality score refers to a scan having more favorable longitudinal data than that with a "low" longitudinal quality score.

Diagnosis data 440 can include data that indicates an automated diagnosis, a tentative diagnosis, and/or data that can otherwise be used to support medical diagnosis, triage, medical evaluation and/or other review by a medical professional or other user. The diagnosis data 440 of a medical scan can include a binary abnormality identifier 441 indicating whether the scan is normal or includes at least one abnormality. In some embodiments, the binary abnormality identifier 441 can be determined by comparing some or all of confidence score data 460 to a threshold, can be determined by comparing a probability value to a threshold, and/or can be determined by comparing another continuous or discrete value indicating a calculated likelihood that the scan contains one or more abnormalities to a threshold. In some embodiments, non-binary values, such as one or more continuous or discrete values indicating a likelihood that the scan contains one or more abnormalities, can be included in diagnosis data 440 in addition to, or instead of, binary abnormality identifier 441. One or abnormalities can be identified by the diagnosis data 440, and each identified abnormality can include its own set of abnormality annotation data 442. Alternatively, some or all of the diagnosis data 440 can indicate and/or describe multiple abnormalities, and thus will not be presented for each abnormality in the abnormality annotation data 442. For example, the report data 449 of the diagnosis data 440 can describe all identified abnormalities, and thus a single report can be included in the diagnosis.

Figure 4B:
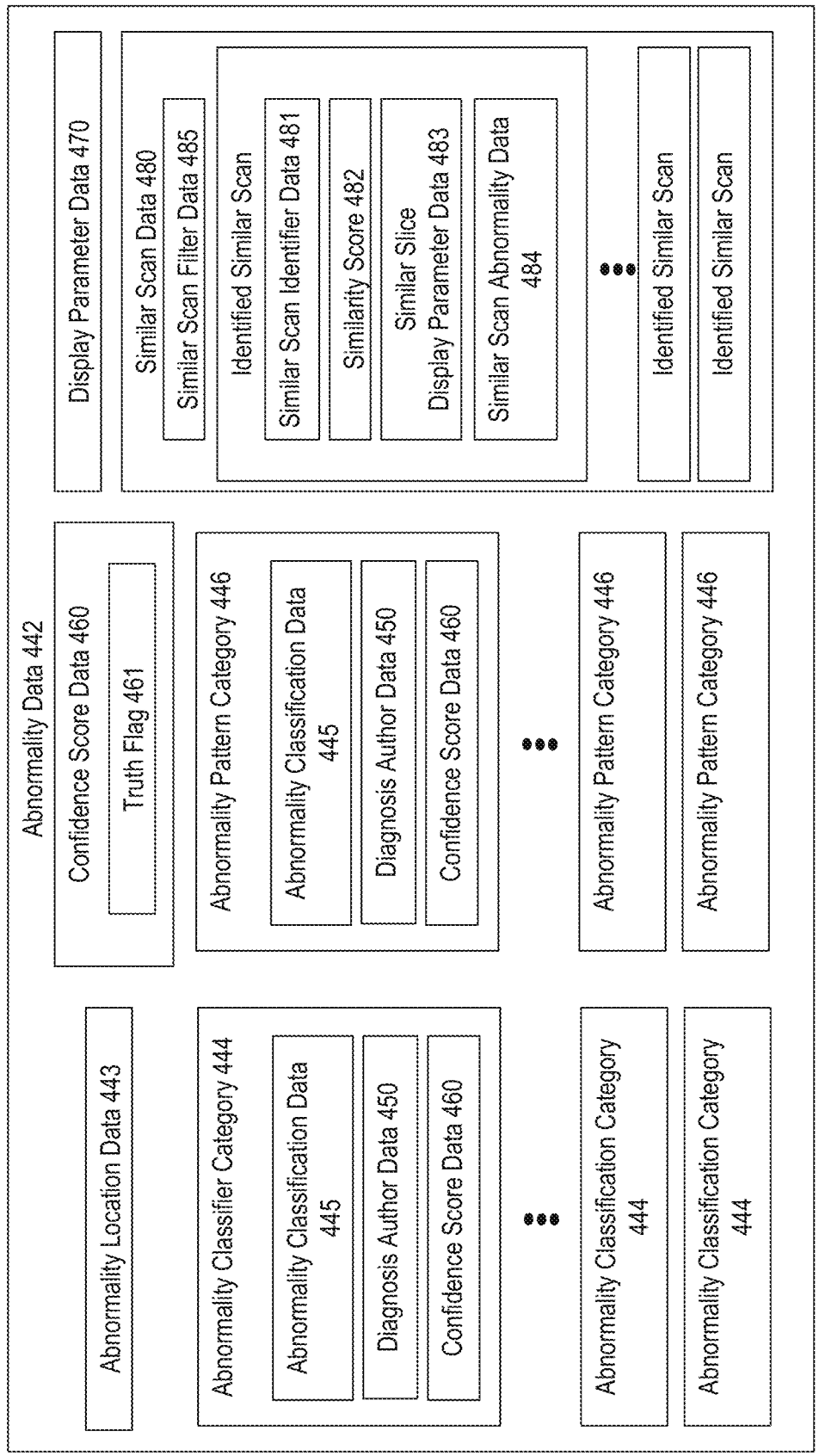
FIG. 4B is a schematic block diagram of abnormality data in accordance with various embodiments.

FIG. 4B presents an embodiment of the abnormality annotation data 442. The abnormality annotation data 442 for each abnormality can include abnormality location data 443, which can include an anatomical location and/or a location specific to pixels, image slices, coordinates or other location information identifying regions of the medical scan itself. The abnormality annotation data 442 can include abnormality classification data 445 which can include binary, quantitative, and/or descriptive data of the abnormality as a whole, or can correspond to one or more abnormality classifier categories 444, which can include size, volume, pre-post contrast, doubling time, calcification, components, smoothness, spiculation, lobulation, sphericity, internal structure, texture, or other categories that can classify and/or otherwise characterize an abnormality. Abnormality classifier categories 444 can be assigned a binary value, indicating whether or not such a category is present. For example, this binary value can be determined by comparing some or all of confidence score data 460 to a threshold, can be determined by comparing a probability value to a threshold, and/or can be determined by comparing another continuous or discrete value indicating a calculated likelihood that a corresponding abnormality classifier category 444 is present to a threshold, which can be the same or different threshold for each abnormality classifier category 444. In some embodiments, abnormality classifier categories 444 can be assigned one or more non-binary values, such as one or more continuous or discrete values indicating a likelihood that the corresponding classifier category 444 is present.

The abnormality classifier categories 444 can also include a malignancy category, and the abnormality classification data 445 can include a malignancy rating such as a Lung-RADS score, a Fleischner score, and/or one or more calculated values that indicate malignancy level, malignancy severity, and/or probability of malignancy. Alternatively or in addition, the malignancy category can be assigned a value of "yes", "no", or "maybe". The abnormality classifier categories 444 can also include abnormality pattern categories 446 such as cardiomegaly, consolidation, effusion, emphysema, and/or fracture, and the abnormality classification data 445 for each abnormality pattern category 446 can indicate whether or not each of the abnormality patterns is present.

The abnormality classifier categories can correspond to Response Evaluation Criteria in Solid Tumors (RECIST) eligibility and/or RECIST evaluation categories. For example, an abnormality classifier category 444 corresponding to RECIST eligibility can have corresponding abnormality classification data 445 indicating a binary value "yes" or "no", and/or can indicate if the abnormality is a "target lesion" and/or a "non-target lesion." As another example, an abnormality classifier category 444 corresponding to a RECIST evaluation category can be determined based on longitudinal data 433 and can have corresponding abnormality classification data 445 that includes one of the set of possible values "Complete Response", "Partial Response", "Stable Disease", or "Progressive Disease."

The diagnosis data 440 as a whole, and/or the abnormality annotation data 442 for each abnormality, can include custom codes or datatypes identifying the binary abnormality identifier 441, abnormality location data 443 and/or some or all of the abnormality classification data 445 of one or more abnormality classifier categories 444. Alternatively or in addition, some or all of the abnormality annotation data 442 for each abnormality and/or other diagnosis data 440 can be presented in a DICOM format or other standardized image annotation format, and/or can be extracted into custom datatypes based on abnormality annotation data originally presented in DICOM format. Alternatively or in addition, the diagnosis data 440 and/or the abnormality annotation data 442 for each abnormality can be presented as one or more medical codes 447 such as SNOMED codes, Current Procedure Technology (CPT) codes, ICD-9 codes, ICD-10 codes, or other standardized medical codes used to label or otherwise describe medical scans.

Alternatively or in addition, the diagnosis data 440 can include natural language text data 448 annotating or otherwise describing the medical scan as a whole, and/or the abnormality annotation data 442 can include natural language text data 448 annotating or otherwise describing each corresponding abnormality. In some embodiments, some or all of the diagnosis data 440 is presented only as natural language text data 448. In some embodiments, some or all of the diagnosis data 440 is automatically generated by one or more subsystems based on the natural language text data 448, for example, without utilizing the medical scan image data 410, for example, by utilizing one or more medical scan natural language analysis functions trained by the medical scan natural language analysis system 114. Alternatively or in addition, some embodiments, some or all of the natural language text data 448 is generated automatically based on other diagnosis data 440 such as abnormality annotation data 442, for example, by utilizing a medical scan natural language generating function trained by the medical scan natural language analysis system 114.

The diagnosis data can include report data 449 that includes at least one medical report, which can be formatted to include some or all of the medical codes 447, some or all of the natural language text data 448, other diagnosis data 440, full or cropped images slices formatted based on the display parameter data 470 and/or links thereto, full or cropped images slices or other data based on similar scans of the similar scan data 480 and/or links thereto, full or cropped images or other data based on patient history data 430 such as longitudinal data 433 and/or links thereto, and/or other data or links to data describing the medical scan and associated abnormalities. The diagnosis data 440 can also include finalized diagnosis data corresponding to future scans and/or future diagnosis for the patient, for example, biopsy data or other longitudinal data 433 determined subsequently after the scan. The medical report of report data 449 can be formatted based on specified formatting parameters such as font, text size, header data, bulleting or numbering type, margins, file type, preferences for including one or more full or cropped image slices 412, preferences for including similar medical scans, preferences for including additional medical scans, or other formatting to list natural language text data and/or image data, for example, based on preferences of a user indicated in the originating entity data 423 or other responsible user in the corresponding report formatting data.

Annotation author data 450 can be mapped to the diagnosis data for each abnormality, and/or mapped to the scan as a whole. This can include one or more annotation author identifiers 451, which can include one or more user profile identifiers of a user of the system, such as an individual medical professional, medical facility and/or medical entity that uses the system. Annotation author data 450 can be used to determine the usage data of a user profile entry 354. Annotation author data 450 can also include one or more medical scan analysis function identifiers 357 or other function identifier indicating one or more functions or other processes of a subsystem responsible for automatically generating and/or assisting a user in generating some or all of the diagnosis data, for example an identifier of a particular type and/or version of a medical scan image analysis functions that was used by the medical scan diagnosing system 108 used to generate part or all of the diagnosis data 440 and/or an interface feature identifier, indicating an one or more interface features presented to a user to facilitate entry of and/or reviewing of the diagnosis data 440. The annotation author data can also simply indicate, for one or more portions of the diagnosis data 440, if this portion was generated by a human or automatically generated by a subsystem of the medical scan processing system.

In some embodiments, if a medical scan was reviewed by multiple entities, multiple, separate diagnosis data entries 440 can be included in the medical scan entry 352, mapped to each diagnosis author in the annotation author data 450. This allows different versions of diagnosis data 440 received from multiple entities. For example, annotation author data of a particular medical scan could indicate that the annotation data was written by a doctor at medical entity A, and the medical code data was generated by user Y by utilizing the medical scan report labeling system 104, which was confirmed by expert user X. The annotation author data of another medical scan could indicate that the medical code was generated automatically by utilizing version 7 of the medical scan image analysis function relating to chest x-rays, and confirmed by expert user X. The annotation author data of another medical scan could indicate that the location and a first malignancy rating were generated automatically by utilizing version 7 of the medical scan image analysis function relating to chest x-rays, and that a second malignancy rating was entered by user Z. In some embodiments, one of the multiple diagnosis entries can include consensus annotation data, for example, generated automatically by a subsystem such as the medical scan annotating system 106 based on the multiple diagnosis data 440, based on confidence score data 460 of each of the multiple diagnosis data 440, and/or based on performance score data of a corresponding user, a medical scan analysis function, or an interface feature, identified in the annotation author data for each corresponding one of the multiple diagnosis data 440.

Confidence score data 460 can be mapped to some or all of the diagnosis data 440 for each abnormality, and/or for the scan as a whole. This can include an overall confidence score for the diagnosis, a confidence score for the binary indicator of whether or not the scan was normal, a confidence score for the location a detected abnormality, and/or confidence scores for some or all of the abnormality classifier data. This may be generated automatically by a subsystem, for example, based on the annotation author data and corresponding performance score of one or more identified users and/or subsystem attributes such as interactive interface types or medical scan image analysis functions indicated by the annotation author data. In the case where multiple diagnosis data entries 440 are included from different sources, confidence score data 460 can be computed for each entry and/or an overall confidence score, for example, corresponding to consensus diagnosis data, can be based on calculated distance or other error and/or discrepancies between the entries, and/or can be weighted on the confidence score data 460 of each entry. In various embodiments, the confidence score data 460 can include a truth flag 461 indicating the diagnosis data is considered as "known" or "truth", for example, flagged based on user input, flagged automatically based on the author data, and/or flagged automatically based on the calculated confidence score of the confidence score data exceeding a truth threshold. As used herein, a "high" confidence score refers to a greater degree or more favorable level of confidence than a "low" confidence score.

Display parameter data 470 can indicate parameters indicating an optimal or preferred display of the medical scan by an interactive interface 275 and/or formatted report for each abnormality and/or for the scan as a whole. Some or all of the display parameter data can have separate entries for each abnormality, for example, generated automatically by a subsystem 101 based on the abnormality annotation data 442. Display parameter data 470 can include interactive interface feature data 471, which can indicate one or more selected interface features associated with the display of abnormalities and/or display of the medical scan as a whole, and/or selected interface features associated with user interaction with a medical scan, for example, based on categorized interface feature performance score data and a category associated with the abnormality and/or with the medical scan itself. The display parameter data can include a slice subset 472, which can indicate a selected subset of the plurality of image slices that includes a single image slice 412 or multiple image slices 412 of the medical scan image data 410 for display by a user interface. The display parameter data 470 can include slice order data 473 that indicates a selected custom ordering and/or ranking for the slice subset 472, or for all of the slices 412 of the medical scan. The display parameter data 470 can include slice cropping data 474 corresponding to some or all of the slice subset 472, or all of the image slices 412 of the medical scan, and can indicating a selected custom cropped region of each image slice 412 for display, or the same selected custom cropped region for the slice subset 472 or for all slices 412. The display parameter data can include density window data 475, which can indicate a selected custom density window for display of the medical scan as a whole, a selected custom density window for the slice subset 472, and/or selected custom density windows for each of the image slices 412 of the slice subset 472, and/or for each image slice 412 of the medical scan. The density window data 475 can indicate a selected upper density value cut off and a selected lower density value cut off, and/or can include a selected deterministic function to map each density value of a pixel to a grayscale value based on the preferred density window. The interactive interface feature data 471, slice subset 472, slice order data 473, slice cropping data 474, and/or the density window data 475 can be selected via user input and/or generated automatically by one or more subsystems 101, for example, based on the abnormality annotation data 442 and/or based on performance score data of different interactive interface versions.

Similar scan data 480 can be mapped to each abnormality, or the scan as a whole, and can include similar scan identifier data 481 corresponding to one or more identified similar medical scans, for example, automatically identified by a subsystem 101, for example, by applying a similar scan identification step of the medical scan image analysis system 112 and/or applying medical scan similarity analysis function to some or all of the data stored in the medical scan entry of the medical scan, and/or to some or all corresponding data of other medical scans in the medical scan database. The similar scan data 480 can also correspond to medical scans received from another source. The stored similarity data can be used to present similar cases to users of the system and/or can be used to train medical scan image analysis functions or medical scan similarity analysis functions.

Each identified similar medical scan can have its own medical scan entry 352 in the medical scan database 342 with its own data, and the similar scan identifier data 481 can include the medical scan identifier 353 each similar medical scan. Each identified similar medical scan can be a scan of the same scan type or different scan type than medical scan.

The similar scan data 480 can include a similarity score 482 for each identified similar scan, for example, generated based on some or all of the data of the medical scan entry 352 for medical scan and based on some or all of the corresponding data of the medical scan entry 352 for the identified similar medical scan. For example, the similarity score 482 can be generated based on applying a medical scan similarity analysis function to the medical image scan data of medical scans and 402, to some or all of the abnormality annotation data of medical scans and 402, and/or to some or all of the patient history data 430 of medical scans and 402 such as risk factor data 432. As used herein, a "high" similarity score refers a higher level of similarity that a "low" similarity score.

The similar scan data 480 can include its own similar scan display parameter data 483, which can be determined based on some or all of the display parameter data 470 of the identified similar medical scan. Some or all of the similar scan display parameter data 483 can be generated automatically by a subsystem, for example, based on the display parameter data 470 of the identified similar medical scan, based on the abnormality annotation data 442 of the medical scan itself and/or based on display parameter data 470 of the medical scan itself. Thus, the similar scan display parameter data 483 can be the same or different than the display parameter data 470 mapped to the identified similar medical scan and/or can be the same or different than the display parameter data 470 of the medical scan itself. This can be utilized when displaying similar scans to a user via interactive interface 275 and/or can be utilized when generating report data 449 that includes similar scans, for example, in conjunction with the medical scan assisted review system 102.

The similar scan data 480 can include similar scan abnormality data 484, which can indicate one of a plurality of abnormalities of the identified similar medical scan and its corresponding abnormality annotation data 442. For example, the similarity scan abnormality data 484 can include an abnormality pair that indicates one of a plurality of abnormalities of the medical scan, and indicates one of a plurality of abnormalities of the identified similar medical scan, for example, that was identified as the similar abnormality.

The similar scan data 480 can include similar scan filter data 485. The similar scan filter data can be generated automatically by a subsystem, and can include a selected ordered or un-ordered subset of all identified similar scans of the similar scan data 480, and/or a ranking of all identified similar scans. For example, the subset can be selected and/or some or all identified similar scans can be ranked based on each similarity score 482, and/or based on other factors such as based on a longitudinal quality score 434 of each identified similar medical scan.

The training set data 490 can indicate one or more training sets that the medical scan belongs to. For example, the training set data can indicate one or more training set identifiers 491 indicating one or more medical scan analysis functions that utilized the medical scan in their training set, and/or indicating a particular version identifier 641 of the one or more medical scan analysis functions that utilized the medical scan in their training set. The training set data 490 can also indicate which portions of the medical scan entry were utilized by the training set, for example, based on model parameter data 623 of the corresponding medical scan analysis functions. For example, the training set data 490 can indicate that the medical scan image data 410 was included in the training set utilized to train version X of the chest x-ray medical scan image analysis function, or that the natural language text data 448 of this medical scan was used to train version Y of the natural language analysis function.

Figure 5A:
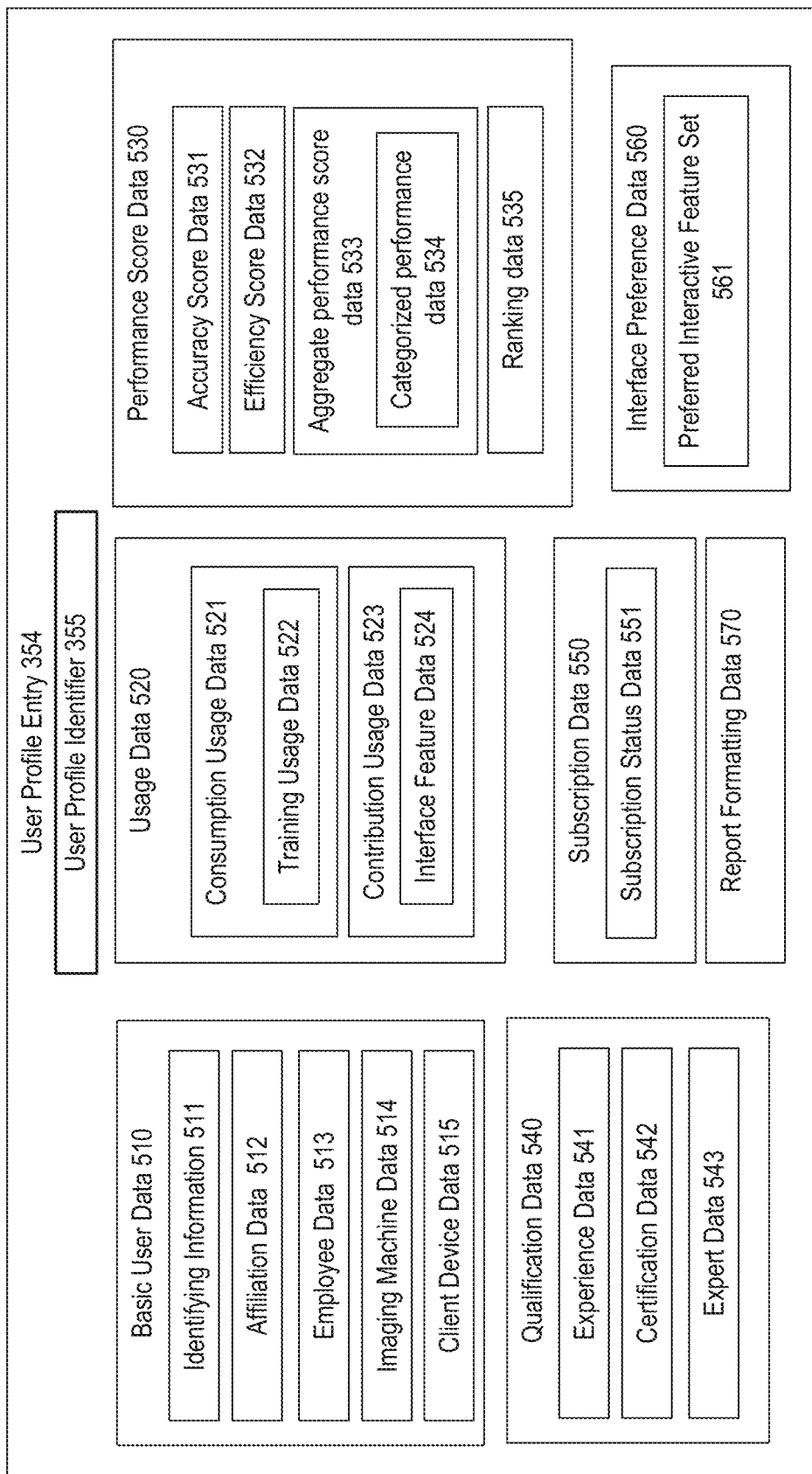
FIG. 5A is a schematic block diagram of a user profile entry in accordance with various embodiments.

FIG. 5A presents an embodiment of a user profile entry 354, stored in user database 344 or otherwise associated with a user. A user can correspond to a user of one or more of the subsystems such as a radiologist, doctor, medical professional, medical report labeler, administrator of one or more subsystems or databases, or other user that uses one or more subsystems 101. A user can also correspond to a medical entity such as a hospital, medical clinic, establishment that utilizes medical scans, establishment that employs one or more of the medical professionals described, an establishment associated with administering one or more subsystems, or other entity. A user can also correspond to a particular client device 120 or account that can be accessed one or more medical professionals or other employees at the same or different medical entities. Each user profile entry can have a corresponding user profile identifier 355.

A user profile entry 354 can include basic user data 510, which can include identifying information 511 corresponding to the user such as a name, contact information, account/login/password information, geographic location information such as geographic region data 424, and/or other basic information. Basic user data 510 can include affiliation data 512, which can list one or more medical entities or other establishments the user is affiliated with, for example, if the user corresponds to a single person such as a medical professional, or if the user corresponds to a hospital in a network of hospitals. The affiliation data 512 can include one or more corresponding user profile identifiers 355 and/or basic user data 510 if the corresponding affiliated medical entity or other establishment has its own entry in the user database. The user identifier data can include employee data 513 listing one or more employees, such as medical professionals with their own user profile entries 354, for example, if the user corresponds to a medical entity or supervising medical professional of other medical professional employees, and can list a user profile identifier 355 and/or basic user data 510 for each employee. The basic user data 510 can also include imaging machine data 514, which can include a list of machines affiliated with the user which can include machine identifiers, model information, calibration information, scan type information, or other data corresponding to each machine, for example, corresponding to the machine data 425. The user profile entry can include client device data 515, which can include identifiers for one or more client devices associated with the user, for example, allowing subsystems 101 to send data to a client device 120 corresponding to a selected user based on the client device data and/or to determine a user that data was received by determining the client device from which the data was received.

The user profile entry can include usage data 520 which can include identifying information for a plurality of usages by the user in conjunction with using one or more subsystems 101. This can include consumption usage data 521, which can include a listing of, or aggregate data associated with, usages of one or more subsystems by the user, for example, where the user is utilizing the subsystem as a service. For example, the consumption usage data 521 can correspond to each instance where diagnosis data was sent to the user for medical scans provided to the user in conjunction with the medical scan diagnosing system 108 and/or the medical scan assisted review system 102. Some or all of consumption usage data 521 can include training usage data 522, corresponding to usage in conjunction with a certification program or other user training provided by one or more subsystems. The training usage data 522 can correspond to each instance where diagnosis feedback data was provided by user for a medical scan with known diagnosis data, but diagnosis feedback data is not utilized by a subsystem to generate, edit, and/or confirm diagnosis data 440 of the medical scan, as it is instead utilized to train a user and/or determine performance data for a user.

Usage data 520 can include contribution usage data 523, which can include a listing of, or aggregate data associated with, usages of one or more subsystems 101 by the user, for example, where the user is generating and/or otherwise providing data and/or feedback that can be utilized by the subsystems, for example, to generate, edit, and/or confirm diagnosis data 440 and/or to otherwise populate, modify, or confirm portions of the medical scan database or other subsystem data. For example, the contribution usage data 523 can correspond to diagnosis feedback data received from user, used to generate, edit, and/or confirm diagnosis data. The contribution usage data 523 can include interactive interface feature data 524 corresponding to the interactive interface features utilized with respect to the contribution.

The consumption usage data 521 and/or the contribution usage data 523 can include medical scan entry 352 whose entries the user utilized and/or contributed to, can indicate one or more specific attributes of a medical scan entry 352 that a user utilized and/or contributed to, and/or a log of the user input generated by a client device of the user in conjunction with the data usage. The contribution usage data 523 can include the diagnosis data that the user may have generated and/or reviewed, for example, indicated by, mapped to, and/or used to generate the annotation author data 450 of corresponding medical scan entries 352. Some usages may correspond to both consumption usage of the consumption usage data 521 and contribution usage of the contribution usage data 523. The usage data 520 can also indicate one or more subsystems 101 that correspond to each consumption and/or contribution.

The user profile entry can include performance score data 530. This can include one or more performance scores generated based on the contribution usage data 523 and/or training usage data 522. The performance scores can include separate performance scores generated for every contribution in the contribution usage data 523 and/or training usage data 522 and/or generated for every training consumption usages corresponding to a training program. As used herein, a "high" performance score refers to a more favorable performance or rating than a "low" performance score.

The performance score data can include accuracy score data 531, which can be generated automatically by a subsystem for each contribution, for example, based on comparing diagnosis data received from a user to data to known truth data such as medical scans with a truth flag 461, for example, retrieved from the corresponding medical scan entry 352 and/or based on other data corresponding to the medical scan, for example, received from an expert user that later reviewed the contribution usage data of the user and/or generated automatically by a subsystem. The accuracy score data 531 can include an aggregate accuracy score generated automatically by a subsystem, for example, based on the accuracy data of multiple contributions by the user over time.

The performance data can also include efficiency score data 532 generated automatically by a subsystem for each contribution based on an amount of time taken to complete a contribution, for example, from a time the request for a contribution was sent to the client device to a time that the contribution was received from the client device, based on timing data received from the client device itself, and/or based on other factors. The efficiency score can include an aggregate efficiency score, which can be generated automatically by a subsystem based on the individual efficiency scores over time and/or based on determining a contribution completion rate, for example based on determining how many contributions were completed in a fixed time window.

Aggregate performance score data 533 can be generated automatically by a subsystem based on the aggregate efficiency and/or accuracy data. The aggregate performance data can include categorized performance data 534, for example, corresponding to different scan types, different anatomical regions, different subsystems, different interactive interface features and/or display parameters. The categorized performance data 534 can be determined automatically by a subsystem based on the scan type data 421 and/or anatomical region data 422 of the medical scan associated with each contribution, one or more subsystems 101 associated with each contribution, and/or interactive interface feature data 524 associated with each contribution. The aggregate performance data can also be based on performance score data 530 of individual employees if the user corresponds to a medical entity, for example, retrieved based on user profile identifiers 355 included in the employee data 513. The performance score data can also include ranking data 535, which can include an overall ranking or categorized rankings, for example, generated automatically by a subsystem or the database itself based on the aggregate performance data.

In some embodiments, aggregate data for each user can be further broken down based on scores for distinct scan categories, for example, based on the scan classifier data 420, for example, where a first aggregate data score is generated for a user "A" based on scores from all knee x-rays, and a second aggregate data score is generated for user A based on scores from all chest CT scans. Aggregate data for each user can be further based on scores for distinct diagnosis categories, where a first aggregate data score is generated for user A based on scores from all normal scans, and a second aggregate data score is generated for user A based on scores from all scans that contain an abnormality. This can be further broken down, where a first aggregate score is generated for user A based on all scores from scans that contain an abnormality of a first type and/or in a first anatomical location, and a second aggregate score is generated for A based on all scores from scans that contain an abnormality of a second type and/or in a second location. Aggregate data for each user can be further based on affiliation data, where a ranking is generated for a medical professional "B" based on scores from all medical professionals with the same affiliation data, and/or where a ranking is generated for a hospital "C" based on scores for all hospitals, all hospitals in the same geographical region, etc. Aggregate data for each user can be further based on scores for interface features, where a first aggregate data score is generated for user A based on scores using a first interface feature, and a second aggregate data score is generated for user A based on scores using a first interface feature.

The user profile entry can include qualification data 540. The qualification data can include experience data 541 such as education data, professional practice data, number of years practicing, awards received, etc. The qualification data 540 can also include certification data 542 corresponding to certifications earned based on contributions to one or more subsystems, for example, assigned to users automatically by a subsystem based on the performance score data 530 and/or based on a number of contributions in the contribution usage data 523 and/or training usage data 522. For example, the certifications can correspond to standard and/or recognized certifications to train medical professionals and/or incentivize medical professionals to use the system. The qualification data 540 can include expert data 543. The expert data 543 can include a binary expert identifier, which can be generated automatically by a subsystem based on experience data 541, certification data 542, and/or the performance score data 530, and can indicate whether the user is an expert user. The expert data 543 can include a plurality of categorized binary expert identifiers corresponding to a plurality of qualification categories corresponding to corresponding to scan types, anatomical regions, and/or the particular subsystems. The categorized binary expert identifiers can be generated automatically by a subsystem based on the categorized performance data 534 and/or the experience data 541. The categories be ranked by performance score in each category to indicate particular specialties. The expert data 543 can also include an expert ranking or categorized expert ranking with respect to all experts in the system.

The user profile entry can include subscription data 550, which can include a selected one of a plurality of subscription options that the user has subscribed to. For example, the subscription options can correspond to allowed usage of one or more subsystems, such as a number of times a user can utilize a subsystem in a month, and/or to a certification program, for example paid for by a user to receive training to earn a subsystem certification of certification data 542. The subscription data can include subscription expiration information, and/or billing information. The subscription data can also include subscription status data 551, which can for example indicate a number of remaining usages of a system and/or available credit information. For example, the remaining number of usages can decrease and/or available credit can decrease in response to usages that utilize one or more subsystems as a service, for example, indicated in the consumption usage data 521 and/or training usage data 522. In some embodiments, the remaining number of usages can increase and/or available credit can increase in response to usages that correspond to contributions, for example, based on the contribution usage data 523. An increase in credit can be variable, and can be based on a determined quality of each contribution, for example, based on the performance score data 530 corresponding to the contribution where a higher performance score corresponds to a higher increase in credit, based on scan priority data 427 of the medical scan where contributing to higher priority scans corresponds to a higher increase in credit, or based on other factors.

The user profile entry 354 can include interface preference data 560. The interface preference data can include a preferred interactive interface feature set 561, which can include one or more interactive interface feature identifiers and/or one or more interactive interface version identifiers of interface feature entries 358 and/or version identifiers of the interface features. Some or all of the interface features of the preferred interactive interface feature set 561 can correspond to display parameter data 470 of medical scans. The preferred interactive interface feature set 561 can include a single interactive feature identifier for one or more feature types and/or interface types, and/or can include a single interactive interface version identifier for one or more interface categories. The preferred interactive interface feature set 561 can include a ranking of multiple features for the same feature type and/or interface type. The ranked and/or unranked preferred interactive interface feature set 561 can be generated based on user input to an interactive interface of the client device to select and/or rank some or all of the interface features and/or versions. Some or all of the features and/or versions of the preferred interactive feature set can be selected and/or ranked automatically by a subsystem such as the medical scan interface evaluator system, for example based on interface feature performance score data and/or feature popularity data. Alternatively or in addition, the performance score data 530 can be utilized by a subsystem to automatically determine the preferred interactive feature set, for example, based on the scores in different feature-based categories of the categorized performance data 534.

The user profile entry 354 can include report formatting data 570, which can indicate report formatting preferences indicated by the user. This can include font, text size, header data, bulleting or numbering type, margins, file type, preferences for including one or more full or cropped image slices 412, preferences for including similar medical scans, preferences for including additional medical scans in reports, or other formatting preference to list natural language text data and/or image data corresponding to each abnormality. Some or all of the report formatting data 570 can be based on interface preference data 560. The report formatting data 570 can be used by one or more subsystems to automatically generate report data 449 of medical scans based on the preferences of the requesting user.

Figure 5B:
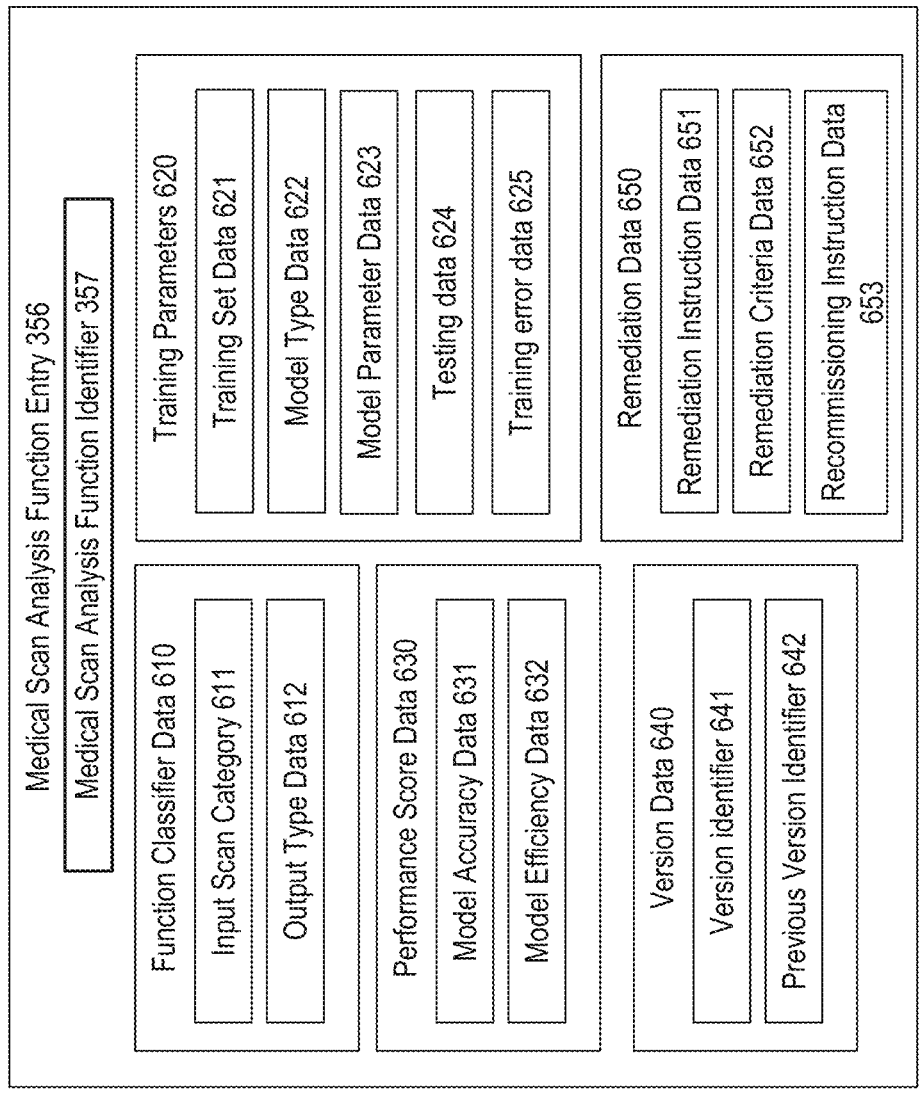
FIG. 5B is a schematic block diagram of a medical scan analysis function entry in accordance with various embodiments.

FIG. 5B presents an embodiment of a medical scan analysis function entry 356, stored in medical scan analysis function database 346 or otherwise associated with one of a plurality of medical scan analysis functions trained by and/or utilized by one or more subsystems 101. For example, a medical scan analysis function can include one or more medical scan image analysis functions trained by the medical scan image analysis system 112; one or more medical scan natural language analysis functions trained by the medical scan natural language analysis system 114; one or more medical scan similarity analysis function trained by the medical scan image analysis system 112, the medical scan natural language analysis system 114, and/or the medical scan comparison system 116; one or more medical report generator functions trained by the medical scan natural language analysis system 114 and/or the medical scan image analysis system 112, and/or the medical report analysis function trained by the medical scan natural language analysis system 114. Some or all of the medical scan analysis functions can correspond to medical scan inference functions of the medical scan diagnosing system 108, the de-identification function and/or the inference functions utilized by a medical picture archive integration system as discussed in conjunction with FIGS. 8A-8F, or other functions and/or processes described herein in conjunction with one or more subsystems 101. Each medical scan analysis function entry 356 can include a medical scan analysis function identifier 357.

A medical scan analysis function entry 356 can include function classifier data 610. Function classifier data 610 can include input and output types corresponding to the function. For example the function classifier data can include input scan category 611 that indicates which types of scans can be used as input to the medical scan analysis function. For example, input scan category 611 can indicate that a medical scan analysis function is for chest CT scans from a particular hospital or other medical entity. The input scan category 611 can include one or more categories included in scan classifier data 420. In various embodiments, the input scan category 611 corresponds to the types of medical scans that were used to train the medical scan analysis function. Function classifier data 610 can also include output type data 612 that characterizes the type of output that will be produced by the function, for example, indicating that a medical scan analysis function is used to generate medical codes 447. The input scan category 611 can also include information identifying which subsystems 101 are responsible for running the medical scan analysis function.

A medical scan analysis function entry 356 can include training parameters 620. This can include training set data 621, which can include identifiers for the data used to train the medical scan analysis function, such as a set of medical scan identifiers 353 corresponding to the medical scans used to train the medical scan analysis function, a list of medical scan reports and corresponding medical codes used to train the medical scan analysis function, etc. Alternatively or in addition to identifying particular scans of the training set, the training set data 621 can identify training set criteria, such as necessary scan classifier data 420, necessary abnormality locations, classifiers, or other criteria corresponding to abnormality annotation data 442, necessary confidence score data 460, for example, indicating that only medical scans with diagnosis data 440 assigned a truth flag 461 or with confidence score data 460 otherwise comparing favorably to a training set confidence score threshold are included, a number of medical scans to be included and proportion data corresponding to different criteria, or other criteria used to populate a training set with data of medical scans. Training parameters 620 can include model type data 622 indicating one or more types of model, methods, and/or training functions used to determine the medical scan analysis function by utilizing the training set 621. Training parameters 620 can include model parameter data 623 that can include a set of features of the training data selected to train the medical scan analysis function, determined values for weights corresponding to selected input and output features, determined values for model parameters corresponding to the model itself, etc. The training parameter data can also include testing data 624, which can identify a test set of medical scans or other data used to test the medical scan analysis function. The test set can be a subset of training set 621, include completely separate data than training set 621, and/or overlap with training set 621. Alternatively or in addition, testing data 624 can include validation parameters such as a percentage of data that will be randomly or pseudo-randomly selected from the training set for testing, parameters characterizing a cross validation process, or other information regarding testing. Training parameters 620 can also include training error data 625 that indicates a training error associated with the medical scan analysis function, for example, based on applying cross validation indicated in testing data 624.

A medical scan analysis function entry 356 can include performance score data 630. Performance data can include model accuracy data 631, for example, generated and/or updated based on the accuracy of the function when performed on new data. For example, the model accuracy data 631 can include or be calculated based on the model error for determined for individual uses, for example, generated by comparing the output of the medical scan analysis function to corresponding data generated by user input to interactive interface 275 in conjunction with a subsystem 101 and/or generated by comparing the output of the medical scan analysis function to medical scans with a truth flag 461. The model accuracy data 631 can include aggregate model accuracy data computed based on model error of individual uses of the function over time. The performance score data 630 can also include model efficiency data 632, which can be generated based on how quickly the medical scan analysis function performs, how much memory is utilized by medical scan analysis function, or other efficiency data relating to the medical scan analysis function. Some or all of the performance score data 630 can be based on training error data 625 or other accuracy and/or efficiency data determined during training and/or validation. As used herein, a "high" performance score refers to a more favorable performance or rating than a "low" performance score.

A medical scan analysis function entry 356 can include version data 640. The version data can include a version identifier 641. The version data can indicate one or more previous version identifiers 642, which can map to version identifiers 641 stored in other medical scan analysis function entry 356 that correspond to previous versions of the function. Alternatively or in addition, the version data can indicate multiple versions of the same type based on function classifier data 610, can indicate the corresponding order and/or rank of the versions, and/or can indicate training parameters 620 associated with each version.

A medical scan analysis function entry 356 can include remediation data 650. Remediation data 650 can include remediation instruction data 651 which can indicate the steps in a remediation process indicating how a medical scan analysis function is taken out of commission and/or reverted to a previous version in the case that remediation is necessary. The version data 640 can further include remediation criteria data 652, which can include threshold data or other criteria used to automatically determine when remediation is necessary. For example, the remediation criteria data 652 can indicate that remediation is necessary at any time where the model accuracy data and/or the model efficiency data compares unfavorably to an indicated model accuracy threshold and/or indicated model efficiency threshold. The remediation data 650 can also include recommissioning instruction data 653, identifying required criteria for recommissioning a medical scan analysis function and/or updating a medical scan analysis function. The remediation data 650 can also include remediation history, indicating one or more instances that the medical scan analysis function was taken out of commission and/or was recommissioned.

Figure 6A:
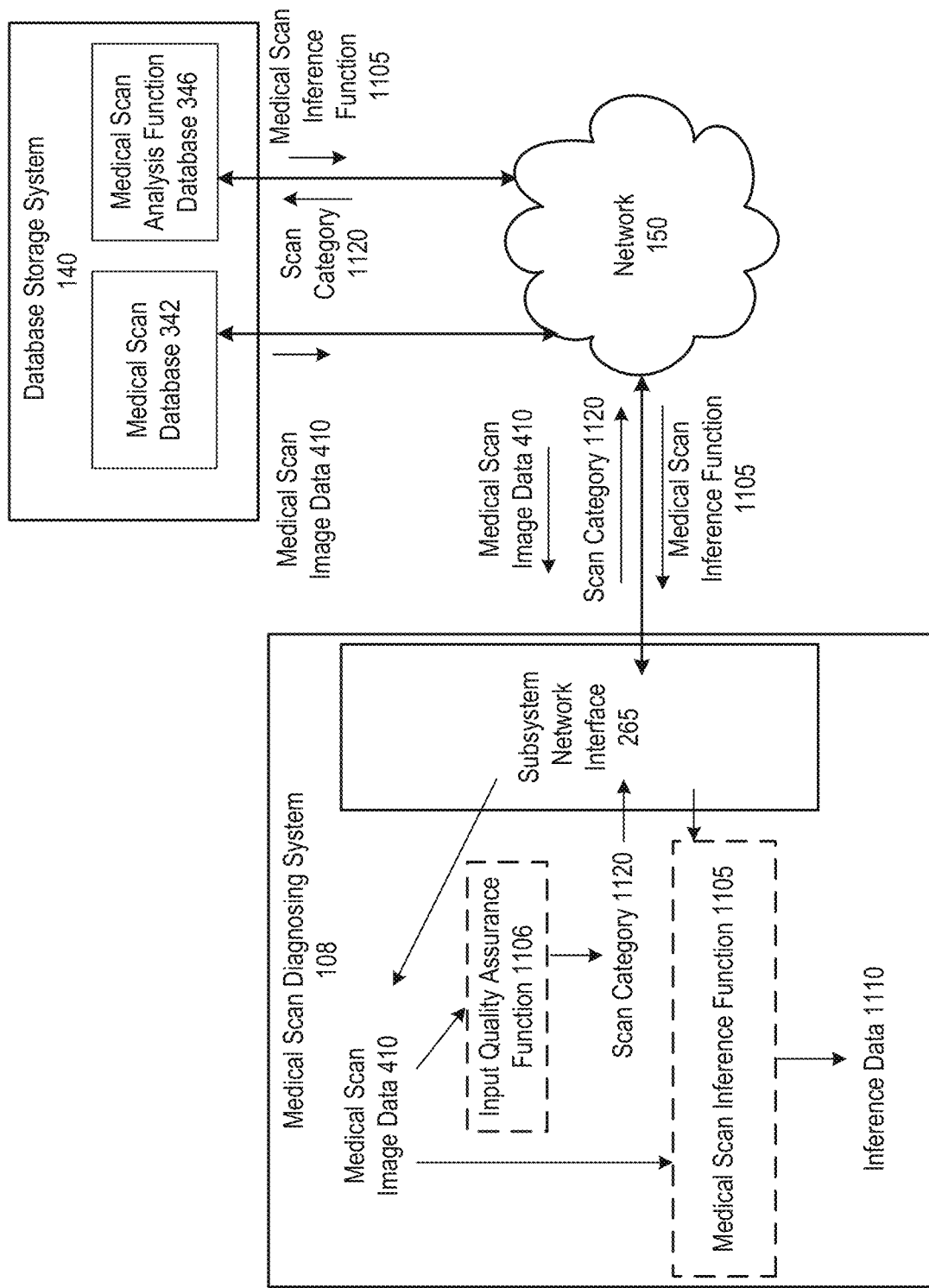
FIGS. 6A-6B are schematic block diagram of a medical scan diagnosing system in accordance with various embodiments.
Figure 6B:
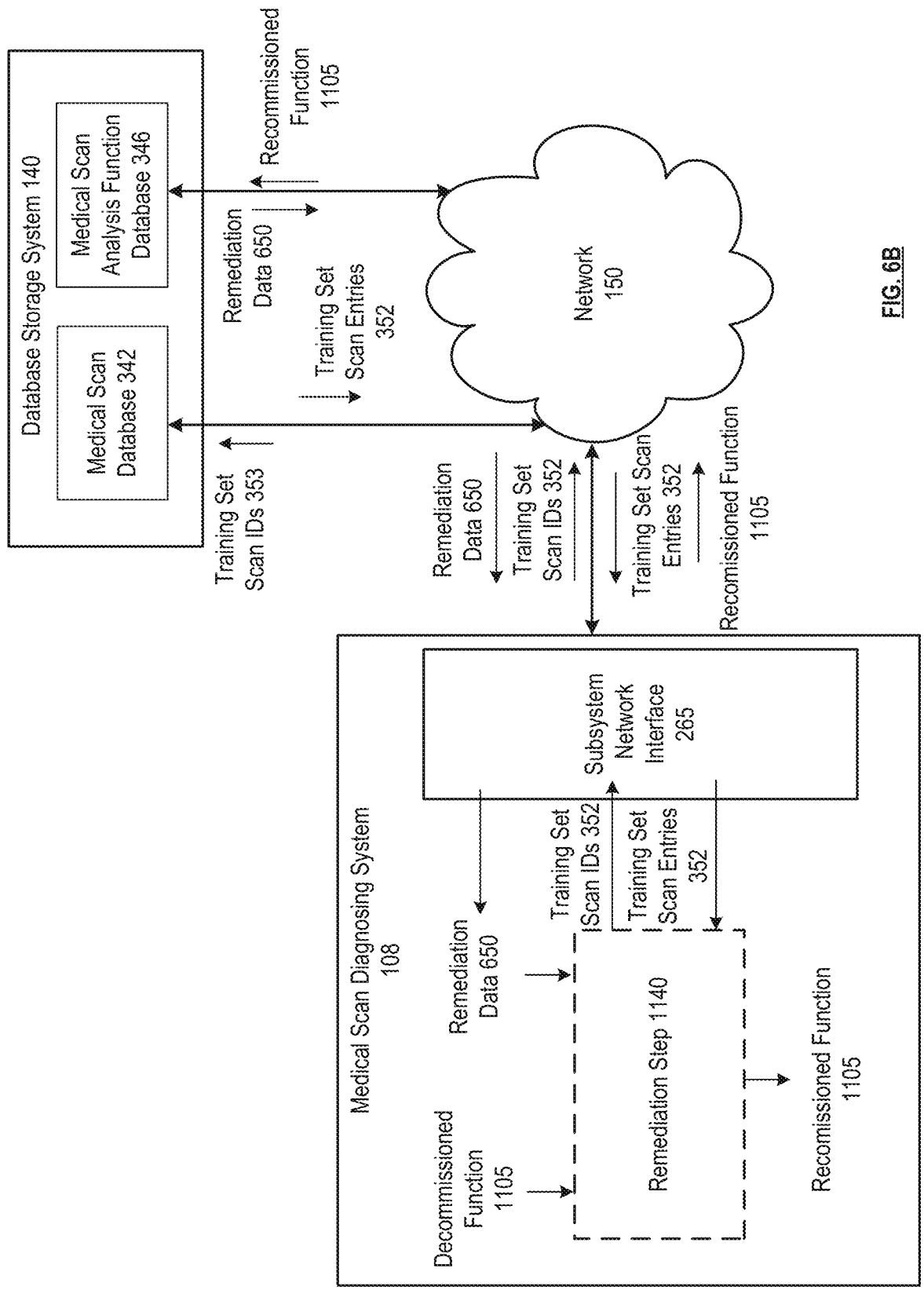

FIGS. 6A and 6B present an embodiment of a medical scan diagnosing system 108.

The medical scan diagnosing system 108 can generate inference data 1110 for medical scans by utilizing a set of medical scan inference functions 1105, stored and run locally, stored and run by another subsystem 101, and/or stored in the medical scan analysis function database 346, where the function and/or parameters of the function can be retrieved from the database by the medical scan diagnosing system. For example, the set of medical scan inference function 1105 can include some or all medical scan analysis functions described herein or other functions that generate inference data 1110 based on some or all data corresponding to a medical scan such as some or all data of a medical scan entry 352. Each medical scan inference function 1105 in the set can correspond to a scan category 1120, and can be trained on a set of medical scans that compare favorably to the scan category 1120. For example, each inference function can be trained on a set of medical scans of the one or more same scan classifier data 420, such as the same and/or similar scan types, same and/or similar anatomical regions locations, same and/or similar machine models, same and/or similar machine calibration, same and/or similar contrasting agent used, same and/or similar originating entity, same and/or similar geographical region, and/or other classifiers. Thus, the scan categories 1120 can correspond to one or more of a scan type, scan anatomical region data, hospital or other originating entity data, machine model data, machine calibration data, contrast agent data, geographic region data, and/or other scan classifying data 420. For example, a first medical scan inference function can be directed to characterizing knee x-rays, and a second medical scan inference function can be directed to chest CT scans. As another example, a first medical scan inference function can be directed to characterizing CT scans from a first hospital, and a second medical scan image analysis function can be directed to characterizing CT scans from a second hospital.

Training on these categorized sets separately can ensure each medical scan inference function 1105 is calibrated according to its scan category 1120, for example, allowing different inference functions to be calibrated on type specific, anatomical region specific, hospital specific, machine model specific, and/or region-specific tendencies and/or discrepancies. Some or all of the medical scan inference functions 1105 can be trained by the medical scan image analysis system and/or the medical scan natural language processing system, and/or some medical scan inference functions 1105 can utilize both image analysis and natural language analysis techniques to generate inference data 1110. For example, some or all of the inference functions can utilize image analysis of the medical scan image data 410 and/or natural language data extracted from abnormality annotation data 442 and/or report data 449 as input, and generate diagnosis data 440 such as medical codes 447 as output. Each medical scan inference function can utilize the same or different learning models to train on the same or different features of the medical scan data, with the same or different model parameters, for example indicated in the model type data 622 and model parameter data 623. Model type and/or parameters can be selected for a particular medical scan inference function based on particular characteristics of the one or more corresponding scan categories 1120, and some or all of the indicated in the model type data 622 and model parameter data 623 can be selected automatically by a subsystem during the training process based on the particular learned and/or otherwise determined characteristics of the one or more corresponding scan categories 1120.

As shown in FIG. 6A, the medical scan diagnosing system 108 can automatically select a medical scan for processing in response to receiving it from a medical entity via the network. Alternatively, the medical scan diagnosing system 108 can automatically retrieve a medical scan from the medical scan database that is selected based on a request received from a user for a particular scan and/or based on a queue of scans automatically ordered by the medical scan diagnosing system 108 or another subsystem based on scan priority data 427.

Once a medical scan to be processed is determined, the medical scan diagnosing system 108 can automatically select an inference function 1105 based on a determined scan category 1120 of the selected medical scan and based on corresponding inference function scan categories. The scan category 1120 of a scan can be determined based one some or all of the scan classifier data 420 and/or based on other metadata associated with the scan. This can include determining which one of the plurality of medical scan inference functions 1105 matches or otherwise compares favorably to the scan category 1120, for example, by comparing the scan category 1120 to the input scan category of the function classifier data 610.

Alternatively or in addition, the medical scan diagnosing system 108 can automatically determine which medical scan inference function 1105 is utilized based on an output preference that corresponding to a desired type of inference data 1110 that is outputted by an inference function 1105. The output preference designated by a user of the medical scan diagnosing system 108 and/or based on the function of a subsystem 101 utilizing the medical scan diagnosing system 108. For example, the set of inference functions 1105 can include inference functions that are utilized to indicate whether or not a medical scan is normal, to automatically identify at least one abnormality in the scan, to automatically characterize the at least one abnormality in the scan, to assign one or more medical codes to the scan, to generate natural language text data and/or a formatted report for the scan, and/or to automatically generate other diagnosis data such as some or all of diagnosis data 440 based on the medical scan. Alternatively or in addition, some inference functions can also be utilized to automatically generate confidence score data 460, display parameter data 470, and/or similar scan data 480. The medical scan diagnosing system 108 can compare the output preference to the output type data 612 of the medical scan inference function 1105 to determine the selected inference function 1105. For example, this can be used to decide between a first medical scan inference function that automatically generates medical codes and a second medical scan inference function that automatically generates natural language text for medical reports based on the desired type of inference data 1110.

Prior to performing the selected medical scan inference function 1105, the medical scan diagnosing system 108 can automatically perform an input quality assurance function 1106 to ensure the scan classifier data 420 or other metadata of the medical scan accurately classifies the medical scan such that the appropriate medical scan inference function 1105 of the appropriate scan category 1120 is selected. The input quality assurance function can be trained on, for example, medical scan image data 410 of plurality of previous medical scans with verified scan categories. Thus, the input quality assurance function 1106 can take medical scan image data 410 as input and can generate an inferred scan category as output. The inferred scan category can be compared to the scan category 1120 of the scan, and the input quality assurance function 1106 can determine whether or not the scan category 1120 is appropriate by determining whether the scan category 1120 compares favorably to the automatically generated inferred scan category. The input quality assurance function 1106 can also be utilized to reassign the generated inferred scan category to the scan category 1120 when the scan category 1120 compares favorably to the automatically generated inferred scan category. The input quality assurance function 1106 can also be utilized to assign the generated inferred scan category to the scan category 1120 for incoming medical scans that do not include any classifying data, and/or to add classifiers in scan classifier data 420 to medical scans missing one or more classifiers.

In various embodiments, upon utilizing the input quality assurance function 1106 to determine that the scan category 1120 determined by a scan classifier data 420 or other metadata is inaccurate, the medical scan diagnosing system 108 can transmit an alert and/or an automatically generated inferred scan category to the medical entity indicating that the scan is incorrectly classified in the scan classifier data 420 or other metadata. In some embodiments, the medical scan diagnosing system 108 can automatically update performance score data corresponding to the originating entity of the scan indicated in originating entity data 423, or another user or entity responsible for classifying the scan, for example, where a lower performance score is generated in response to determining that the scan was incorrectly classified and/or where a higher performance score is generated in response to determining that the scan was correctly classified.

In some embodiments, the medical scan diagnosing system 108 can transmit the medical scan and/or the automatically generated inferred scan category to a selected user. The user can be presented the medical scan image data 410 and/or other data of the medical scan via the interactive interface 275, for example, displayed in conjunction with the medical scan assisted review system 102. The interface can prompt the user to indicate the appropriate scan category 1120 and/or prompt the user to confirm and/or edit the inferred scan category, also presented to the user. For example, scan review data can be automatically generated to reflect the user generated and/or verified scan category 1120. This user indicated scan category 1120 can be utilized to select to the medical scan inference function 1105 and/or to update the scan classifier data 420 or other metadata accordingly. In some embodiments, for example, where the scan review data indicates that the selected user disagrees with the automatically generated inferred scan category created by the input quality assurance function 1106, the medical scan diagnosing system 108 can automatically update performance score data 630 of the input quality assurance function 1106 by generating a low performance score and/or determine to enter the remediation step 1140 for the input quality assurance function 1106.

The medical scan diagnosing system 108 can also automatically perform an output quality assurance step after a medical scan inference function 1105 has been performed on a medical scan to produce the inference data 1110, as illustrated in the embodiment presented in FIG. 6B. The output quality assurance step can be utilized to ensure that the selected medical scan inference function 1105 generated appropriate inference data 1110 based on expert feedback. The inference data 1110 generated by performing the selected medical scan inference function 1105 can be sent to a client device 120 of a selected expert user, such as an expert user in the user database selected based on categorized performance data and/or qualification data that corresponds to the scan category 1120 and/or the inference itself, for example, by selecting an expert user best suited to review an identified abnormality classifier category 444 and/or abnormality pattern category 446 in the inference data 1110 based on categorized performance data and/or qualification data of a corresponding user entry. The selected user can also correspond to a medical professional or other user employed at the originating entity and/or corresponding to the originating medical professional, indicated in the originating entity data 423.

FIG. 6B illustrates an embodiment of the medical scan diagnosing system 108 in conjunction with performing a remediation step 1140. The medical scan diagnosing system 108 can monitor the performance of the set of medical scan inference functions 1105, for example, based on evaluating inference accuracy data outputted by an inference data evaluation function and/or based monitoring on the performance score data 630 in the medical scan analysis function database, and can determine whether or not if the corresponding medical scan inference function 1105 is performing properly. This can include, for example, determining if a remediation step 1140 is necessary for a medical scan inference function 1105, for example, by comparing the performance score data 630 and/or inference accuracy data to remediation criteria data 652. Determining if a remediation step 1140 is necessary can also be based on receiving an indication from the expert user or another user that remediation is necessary for one or more identified medical scan inference functions 1105 and/or for all of the medical scan inference functions 1105.

In various embodiments, a remediation evaluation function is utilized to determine if a remediation step 1140 is necessary for medical scan inference function 1105. The remediation evaluation function can include determining that remediation is necessary when recent accuracy data and/or efficiency data of a particular medical scan inference function 1105 is below the normal performance level of the particular inference function. The remediation evaluation function can include determining that remediation is necessary when recent or overall accuracy data and/or efficiency data of a particular medical scan inference function 1105 is below a recent or overall average for all or similar medical scan inference functions 1105. The remediation evaluation function can include determining that remediation is necessary only after a threshold number of incorrect diagnoses are made. In various embodiments, multiple threshold number of incorrect diagnoses correspond to different diagnoses categories. For example, the threshold number of incorrect diagnoses for remediation can be higher for false negative diagnoses than false positive diagnoses. Similarly, categories corresponding to different diagnosis severities and/or rarities can have different thresholds, for example where a threshold number of more severe and/or more rare diagnoses that were inaccurate to necessitate remediation is lower than a threshold number of less severe and/or less rare diagnoses that were inaccurate.

The remediation step 1140 can include automatically updating an identified medical inference function 1105. This can include automatically retraining identified medical inference function 1105 on the same training set or on a new training set that includes new data, data with higher corresponding confidence scores, or data selected based on new training set criteria. The identified medical inference function 1105 can also be updated and/or changed based on the review data received from the client device. For example, the medical scan and expert feedback data can be added to the training set of the medical scan inference function 1105, and the medical scan inference function 1105 can be retrained on the updated training set. Alternatively or in addition, the expert user can identify additional parameters and/or rules in the expert feedback data based on the errors made by the inference function in generating the inference data 1110 for the medical scan, and these parameters and/or rules can be applied to update the medical scan inference function, for example, by updating the model type data 622 and/or model parameter data 623.

The remediation step 1140 can also include determining to split a scan category 1120 into two or more subcategories. Thus, two or more new medical scan inference functions 1105 can be created, where each new medical scan inference functions 1105 is trained on a corresponding training set that is a subset of the original training set and/or includes new medical scan data corresponding to the subcategory. This can allow medical scan inference functions 1105 to become more specialized and/or allow functions to utilize characteristics and/or discrepancies specific to the subcategory when generating inference data 1110. Similarly, a new scan category 1120 that was not previously represented by any of the medical scan inference functions 1105 can be added in the remediation step, and a new medical scan inference functions 1105 can be trained on a new set of medical scan data that corresponds to the new scan category 1120. Splitting a scan category and/or adding a scan category can be determined automatically by the medical scan diagnosing system 108 when performing the remediation step 1140, for example, based on performance score data 630. This can also be determined based on receiving instructions to split a category and/or add a new scan category from the expert user or other user of the system.

After a medical scan inference function 1105 is updated or created for the first time, the remediation step 1140 can further undergo a commissioning test, which can include rigorous testing of the medical scan inference function 1105 on a testing set, for example, based on the training parameters 620. For example, the commissioning test can be passed when the medical scan inference function 1105 generates a threshold number of correct inference data 1110 and/or the test can be passed if an overall or average discrepancy level between the inference data and the test data is below a set error threshold. The commissioning test can also evaluate efficiency, where the medical scan inference function 1105 only passes the commissioning test if it performs at or exceeds a threshold efficiency level. If the medical scan inference function 1105 fails the commissioning test, the model type and/or model parameters can be modified automatically or based on user input, and the medical scan inference function can be retested, continuing this process until the medical scan inference function 1105 passes the commissioning test.

The remediation step 1140 can include decommissioning the medical scan inference function 1105, for example, while the medical scan inference function is being retrained and/or is undergoing the commissioning test. Incoming scans to the medical scan diagnosing system 108 with a scan category 1120 corresponding to a decommissioned medical scan inference function 1105 can be sent directly to review by one or more users, for example, in conjunction with the medical scan annotator system 106. These user-reviewed medical scans and corresponding annotations can be included in an updated training set used to train the decommissioned medical scan inference function 1105 as part of the remediation step 1140. In some embodiments, previous versions of the plurality of medical scan image analysis functions can be stored in memory of the medical scan diagnosing system and/or can be determined based on the version data 640 of a medical scan inference function 1105. A previous version of a medical scan inference function 1105, such as most recent version or version with the highest performance score, can be utilized during the remediation step 1140 as an alternative to sending all medical scans to user review.

A medical scan inference function can also undergo the remediation step 1140 automatically in response to a hardware and/or software update on processing, memory, and/or other computing devices where the medical scan inference function 1105 is stored and/or performed. Different medical scan inference functions 1105 can be containerized on their own devices by utilizing a micro-service architecture, so hardware and/or software updates may only necessitate that one of the medical scan inference functions 1105 undergo the remediation step 1140 while the others remain unaffected. A medical scan inference function 1105 can also undergo the remediation step 1140 automatically in response to normal system boot-up, and/or periodically in fixed intervals. For example, in response to a scheduled or automatically detected hardware and/or software update, change, or issue, one or more medical scan inference functions 1105 affected by this hardware or software can be taken out of commission until they each pass the commissioning test. Such criteria can be indicated in the remediation criteria data 652.

The medical scan diagnosing system 108 can automatically manage usage data, subscription data, and/or billing data for the plurality of users corresponding to user usage of the system, for example, by utilizing, generating, and/or updating some or all of the subscription data of the user database. Users can pay for subscriptions to the system, which can include different subscription levels that can correspond to different costs. For example, a hospital can pay a monthly cost to automatically diagnose up to 100 medical scans per month. The hospital can choose to upgrade their subscription or pay per-scan costs for automatic diagnosing of additional scans received after the quota is reached and/or the medical scan diagnosing system 108 can automatically send medical scans received after the quota is reached to an expert user associated with the hospital. In various embodiments incentive programs can be used by the medical scan diagnosing system to encourage experts to review medical scans from different medical entities. For example, an expert can receive credit to their account and/or subscription upgrades for every medical scan reviewed, or after a threshold number of medical scans are reviewed. The incentive programs can include interactions by a user with other subsystems, for example, based on contributions made to medical scan entries via interaction with other subsystems.

Figure 7A:
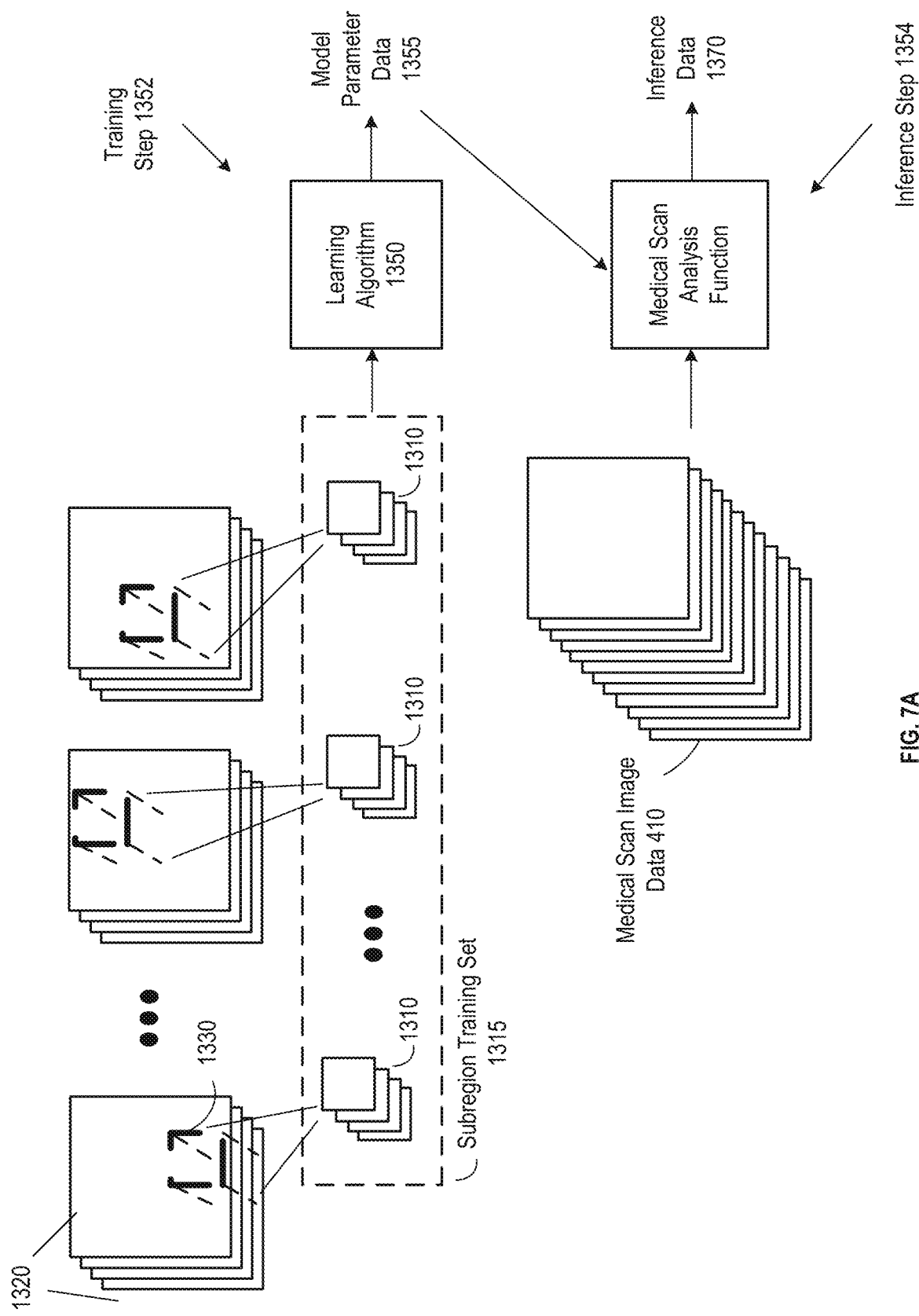
FIG. 7A is a flowchart representation of an inference step in accordance with various embodiments.

FIG. 7A presents an embodiment of a medical scan image analysis system 112. A training set of medical scans used to train one more medical scan image analysis functions can be received from one or more client devices via the network and/or can be retrieved from the medical scan database 342, for example, based on training set data 621 corresponding to medical scan image analysis functions. Training set criteria, for example, identified in training parameters 620 of the medical scan image analysis function, can be utilized to automatically identify and select medical scans to be included in the training set from a plurality of available medical scans. The training set criteria can be automatically generated based on, for example, previously learned criteria, and/or training set criteria can be received via the network, for example, from an administrator of the medical scan image analysis system. The training set criteria can include a minimum training set size. The training set criteria can include data integrity requirements for medical scans in the training set such as requiring that the medical scan is assigned a truth flag 461, requiring that performance score data for a hospital and/or medical professional associated with the medical scan compares favorably to a performance score threshold, requiring that the medical scan has been reviewed by at least a threshold number of medical professionals, requiring that the medical scan and/or a diagnosis corresponding to a patient file of the medical scan is older than a threshold elapsed time period, or based on other criteria intended to insure that the medical scans and associated data in the training set is reliable enough to be considered "truth" data. The training set criteria can include longitudinal requirements such the number of required subsequent medical scans for the patient, multiple required types of additional scans for the patient, and/or other patient file requirements.

The training set criteria can include quota and/or proportion requirements for one or more medical scan classification data. For example, the training set criteria can include meeting quota and/or proportion requirements for one or more scan types and/or human body location of scans, meeting quota or proportion requirements for a number of normal medical scans and a number of medicals scans with identified abnormalities, meeting quota and/or proportion requirements for a number of medical scans with abnormalities in certain locations and/or a number of medical scans with abnormalities that meet certain size, type, or other characteristics, meeting quota and/or proportion data for a number of medical scans with certain diagnosis or certain corresponding medical codes, and/or meeting other identified quota and/or proportion data relating to metadata, patient data, or other data associated with the medical scans.

In some embodiments, multiple training sets are created to generate corresponding medical scan image analysis functions, for example, corresponding to some or all of the set of medical scan inference functions 1105. Some or all training sets can be categorized based on some or all of the scan classifier data 420 as described in conjunction with the medical scan diagnosing system 108, where medical scans are included in a training set based on their scan classifier data 420 matching the scan category of the training set. In some embodiments, the input quality assurance function 1106 or another input check step can be performed on medical scans selected for each training set to confirm that their corresponding scan classifier data 420 is correct. In some embodiments, the input quality assurance function can correspond to its own medical scan image analysis function, trained by the medical scan image analysis system, where the input quality assurance function utilizes high level computer vision technology to determine a scan category 1120 and/or to confirm the scan classifier data 420 already assigned to the medical scan.

In some embodiments, the training set will be used to create a single neural network model, or other model corresponding to model type data 622 and/or model parameter data 623 of the medical scan image analysis function that can be trained on some or all of the medical scan classification data described above and/or other metadata, patient data, or other data associated with the medical scans. In other embodiments, a plurality of training sets will be created to generate a plurality of corresponding neural network models, where the multiple training sets are divided based on some or all of the medical scan classification data described above and/or other metadata, patient data, or other data associated with the medical scans. Each of the plurality of neural network models can be generated based on the same or different learning algorithm that utilizes the same or different features of the medical scans in the corresponding one of the plurality of training sets. The medical scan classifications selected to segregate the medical scans into multiple training sets can be received via the network, for example based on input to an administrator client device from an administrator. The medical scan classifications selected to segregate the medical scans can be automatically determined by the medical scan image analysis system, for example, where an unsupervised clustering algorithm is applied to the original training set to determine appropriate medical scan classifications based on the output of the unsupervised clustering algorithm.

In embodiments where the medical scan image analysis system is used in conjunction with the medical scan diagnosing system, each of the medical scan image analysis functions associated with each neural network model can correspond to one of the plurality of neural network models generated by the medical scan image analysis system. For example, each of the plurality of neural network models can be trained on a training set classified on scan type, scan human body location, hospital or other originating entity data, machine model data, machine calibration data, contrast agent data, geographic region data, and/or other scan classifying data as discussed in conjunction with the medical scan diagnosing system. In embodiments where the training set classifiers are learned, the medical scan diagnosing system can determine which of the medical scan image analysis functions should be applied based on the learned classifying criteria used to segregate the original training set.

A computer vision-based learning algorithm used to create each neural network model can include selecting a three-dimensional subregion 1310 for each medical scan in the training set. This three-dimensional subregion 1310 can correspond to a region that is "sampled" from the entire scan that may represent a small fraction of the entire scan. Recall that a medical scan can include a plurality of ordered cross-sectional image slices. Selecting a three-dimensional subregion 1310 can be accomplished by selecting a proper image slice subset 1320 of the plurality of cross-sectional image slices from each of the plurality of medical scans, and by further selecting a two-dimensional subregion 1330 from each of the selected subset of cross-sectional image slices of the each of the medical scans. In some embodiments, the selected image slices can include one or more non-consecutive image slices and thus a plurality of disconnected three-dimensional subregions will be created. In other embodiments, the selected proper subset of the plurality of image slices correspond to a set of consecutive image slices, as to ensure that a single, connected three-dimensional subregion is selected. In some embodiments, entire scans of the training set are used to train the neural network model. In such embodiment, as used herein, the three-dimensional subregion 1310 can refer to all of the medical scan image data 410 of a medical scan.

In some embodiments, a density windowing step can be applied to the full scan or the selected three-dimensional subregion. The density windowing step can include utilizing a selected upper density value cut off and/or a selected lower density value cut off, and masking pixels with higher values than the upper density value cut off and/or masking pixels with lower values than the lower density value cut off. The upper density value cut off and/or a selected lower density value cut off can be determined based on based on the range and/or distribution of density values included in the region that includes the abnormality, and/or based on the range and/or distribution of density values associated with the abnormality itself, based on user input to a subsystem, based on display parameter data associated with the medical scan or associated with medical scans of the same type, and/or can be learned in the training step. In some embodiments, a non-linear density windowing function can be applied to alter the pixel density values, for example, to stretch or compress contrast. In some embodiments, this density windowing step can be performed as a data augmenting step, to create additional training data for a medical scan in accordance with different density windows.

Having determined the subregion training set 1315 of three-dimensional subregions 1310 corresponding to the set of full medical scans in the training set, the medical scan image analysis system can complete a training step 1352 by performing a learning algorithm on the plurality of three-dimensional subregions to generate model parameter data 1355 of a corresponding learning model. The learning model can include one or more of a neural network, an artificial neural network, a convolutional neural network, a Bayesian model, a support vector machine model, a cluster analysis model, or other supervised or unsupervised learning model. The model parameter data 1355 can generated by performing the learning algorithm 1350, and the model parameter data 1355 can be utilized to determine the corresponding medical scan image analysis functions. For example, some or all of the model parameter data 1355 can be mapped to the medical scan analysis function in the model parameter data 623 or can otherwise define the medical scan analysis function.

The training step 1352 can include creating feature vectors for each three-dimensional subregion of the training set for use by the learning algorithm 1350 to generate the model parameter data 1355. The feature vectors can include the pixel data of the three-dimensional subregions such as density values and/or grayscale values of each pixel based on a determined density window. The feature vectors can also include other features as additional input features or desired output features, such as known abnormality data such as location and/or classification data, patient history data such as risk factor data or previous medical scans, diagnosis data, responsible medical entity data, scan machinery model or calibration data, contrast agent data, medical code data, annotation data that can include raw or processed natural language text data, scan type and/or anatomical region data, or other data associated with the image, such as some or all data of a medical scan entry 352. Features can be selected based on administrator instructions received via the network and/or can be determined based on determining a feature set that reduces error in classifying error, for example, by performing a cross-validation step on multiple models created using different feature sets. The feature vector can be split into an input feature vector and output feature vector. The input feature vector can include data that will be available in subsequent medical scan input, which can include for example, the three-dimensional subregion pixel data and/or patient history data. The output feature vector can include data that will be inferred in in subsequent medical scan input and can include single output value, such as a binary value indicating whether or not the medical scan includes an abnormality or a value corresponding to one of a plurality of medical codes corresponding to the image. The output feature vector can also include multiple values which can include abnormality location and/or classification data, diagnosis data, or other output. The output feature vector can also include a determined upper density value cut off and/or lower density value cut off, for example, characterizing which pixel values were relevant to detecting and/or classifying an abnormality. Features included in the output feature vector can be selected to include features that are known in the training set, but may not be known in subsequent medical scans such as triaged scans to be diagnosed by the medical scan diagnosing system, and/or scans to be labeled by the medical scan report labeling system. The set of features in the input feature vector and output feature vector, as well as the importance of different features where each feature is assigned a corresponding weight, can also be designated in the model parameter data 1355.

Consider a medical scan image analysis function that utilizes a neural network. The neural network can include a plurality of layers, where each layer includes a plurality of neural nodes. Each node in one layer can have a connection to some or all nodes in the next layer, where each connection is defined by a weight value. Thus, the model parameter data 1355 can include a weight vector that includes weight values for every connection in the network. Alternatively or in addition, the model parameter data 1355 can include any vector or set of parameters associated with the neural network model, which can include an upper density value cut off and/or lower density value cut off used to mask some of the pixel data of an incoming image, kernel values, filter parameters, bias parameters, and/or parameters characterizing one or more of a plurality of convolution functions of the neural network model. The medical scan image analysis function can be utilized to produce the output vector as a function of the input feature vector and the model parameter data 1355 that characterizes the neural network model. In particular, the medical scan image analysis function can include performing a forward propagation step plurality of neural network layers to produce an inferred output vector based on the weight vector or other model parameter data 1355. Thus, the learning algorithm 1350 utilized in conjunction with a neural network model can include determining the model parameter data 1355 corresponding to the neural network model, for example, by populating the weight vector with optimal weights that best reduce output error.

In particular, determining the model parameter data 1355 can include utilizing a backpropagation strategy. The forward propagation algorithm can be performed on at least one input feature vector corresponding to at least one medical scan in the training set to propagate the at least one input feature vector through the plurality of neural network layers based on initial and/or default model parameter data 1355, such as an initial weight vector of initial weight values set by an administrator or chosen at random. The at least one output vector generated by performing the forward propagation algorithm on the at least one input feature vector can be compared to the corresponding at least one known output feature vector to determine an output error. Determining the output error can include, for example, computing a vector distance such as the Euclidian distance, or squared Euclidian distance, between the produced output vector and the known output vector, and/or determining an average output error such as an average Euclidian distance or squared Euclidian distance if multiple input feature vectors were employed. Next, gradient descent can be performed to determine an updated weight vector based on the output error or average output error. This gradient descent step can include computing partial derivatives for the error with respect to each weight, or other parameter in the model parameter data 1355, at each layer starting with the output layer. Chain rule can be utilized to iteratively compute the gradient with respect to each weight or parameter at each previous layer until all weight's gradients are computed. Next updated weights, or other parameters in the model parameter data 1355, are generated by updating each weight based on its corresponding calculated gradient. This process can be repeated on at least one input feature vector, which can include the same or different at least one feature vector used in the previous iteration, based on the updated weight vector and/or other updated parameters in the model parameter data 1355 to create a new updated weight vector and/or other new updated parameters in the model parameter data 1355. This process can continue to repeat until the output error converges, the output error is within a certain error threshold, or another criterion is reached to determine the most recently updated weight vector and/or other model parameter data 1355 is optimal or otherwise determined for selection.

Figure 7B:
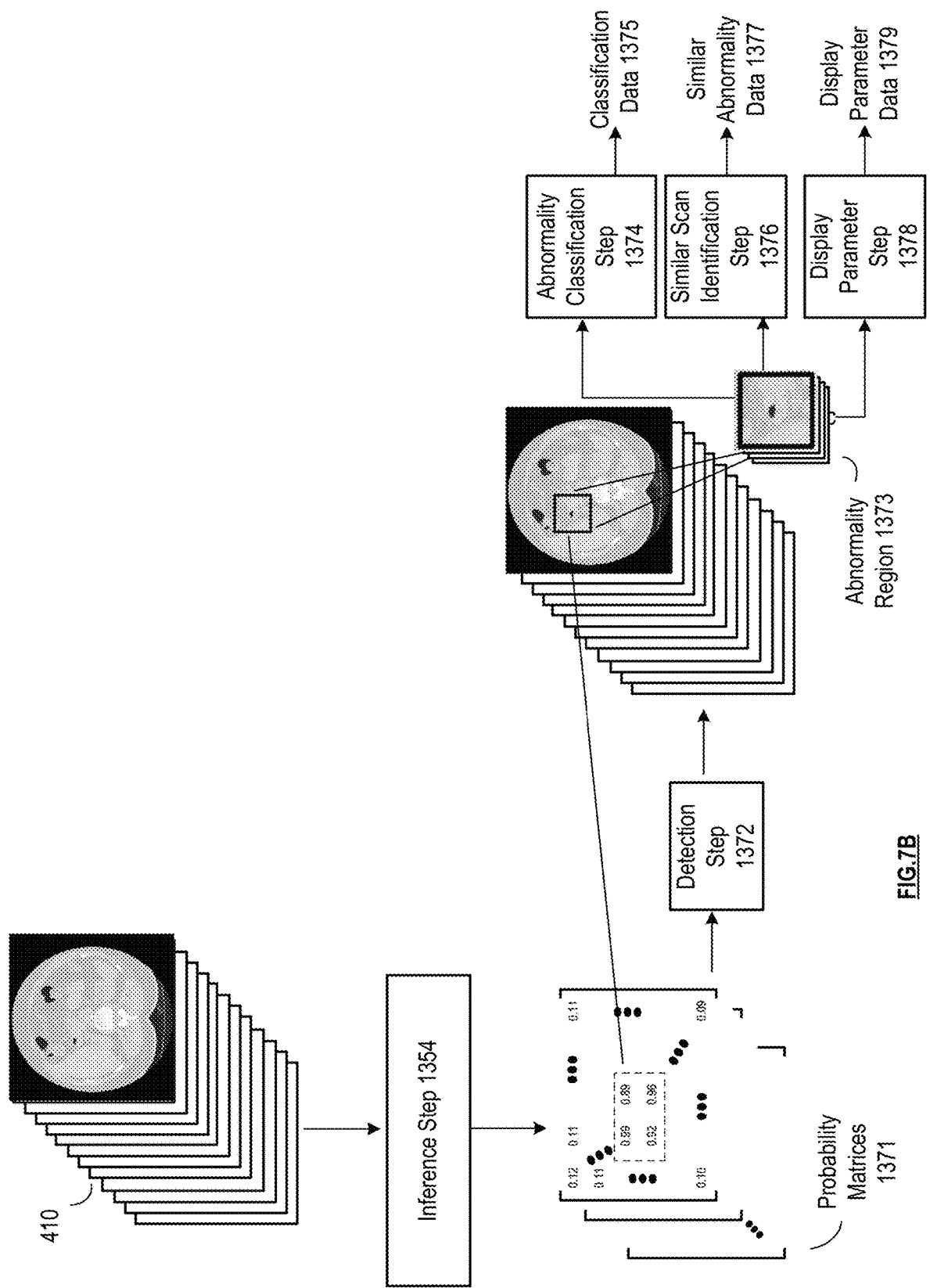
FIG. 7B is a flowchart representation of a detection step in accordance with various embodiments.

Having determined the medical scan neural network and its final other model parameter data 1355, an inference step 1354 can be performed on new medical scans to produce inference data 1370, such as inferred output vectors, as shown in FIG. 7B. The inference step can include performing the forward propagation algorithm to propagate an input feature vector through a plurality of neural network layers based on the final model parameter data 1355, such as the weight values of the final weight vector, to produce the inference data. This inference step 1354 can correspond to performing the medical scan image analysis function, as defined by the final model parameter data 1355, on new medical scans to generate the inference data 1370, for example, in conjunction with the medical scan diagnosing system 108 to generate inferred diagnosis data or other selected output data for triaged medical scans based on its corresponding the input feature vector.

The inference step 1354 can include applying the density windowing step to new medical scans. Density window cut off values and/or a non-linear density windowing function that are learned can be automatically applied when performing the inference step. For example, if the training step 1352 was used to determine optimal upper density value cut off and/or lower density value cut off values to designate an optimal density window, the inference step 1354 can include masking pixels of incoming scans that fall outside of this determined density window before applying the forward propagation algorithm. As another example, if learned parameters of one or more convolutional functions correspond to the optimal upper density value cut off and/or lower density value cut off values, the density windowing step is inherently applied when the forward propagation algorithm is performed on the new medical scans.

In some embodiments where a medical scan analysis function is defined by model parameter data 1355 corresponding to a neutral network model, the neural network model can be a fully convolutional neural network. In such embodiments, only convolution functions are performed to propagate the input feature vector through the layers of the neural network in the forward propagation algorithm. This enables the medical scan image analysis functions to process input feature vectors of any size. For example, as discussed herein, the pixel data corresponding to the three-dimensional subregions is utilized input to the forward propagation algorithm when the training step 1352 is employed to populate the weight vector and/or other model parameter data 1355. However, when performing the forward propagation algorithm in the inference step 1354, the pixel data of full medical scans can be utilized as input, allowing the entire scan to be processed to detect and/or classify abnormalities, or otherwise generate the inference data 1370. This may be a preferred embodiment over other embodiments where new scans must also be sampled by selecting a three-dimensional subregions and/or other embodiments where the inference step requires "piecing together" inference data 1370 corresponding to multiple three-dimensional subregions processed separately.

The inferred output vector of the inference data 1370 can include a plurality of abnormality probabilities mapped to a pixel location of each of a plurality of cross-sectional image slices of the new medical scan. For example, the inferred output vector can indicate a set of probability matrices 1371, where each matrix in the set corresponds to one of the plurality of image slices of the medical scan, where each matrix is a size corresponding to the number of pixels in each image slice, where each cell of each matrix corresponds to a pixel of the corresponding image slice, whose value is the abnormality probability of the corresponding pixel.

A detection step 1372 can include determining if an abnormality is present in the medical scan based on the plurality of abnormality probabilities. Determining if an abnormality is present can include, for example, determining that a cluster of pixels in the same region of the medical scan correspond to high abnormality probabilities, for example, where a threshold proportion of abnormality probabilities must meet or exceed a threshold abnormality probability, where an average abnormality probability of pixels in the region must meet or exceed a threshold abnormality probability, where the region that includes the cluster of pixels must be at least a certain size, etc. Determining if an abnormality is present can also include calculating a confidence score based on the abnormality probabilities and/or other data corresponding to the medical scan such as patient history data. The location of the detected abnormality can be determined in the detection step 1372 based on the location of the pixels with the high abnormality probabilities. The detection step can further include determining an abnormality region 1373, such as a two-dimensional subregion on one or more image slices that includes some or all of the abnormality. The abnormality region 1373 determined in the detection step 1372 can be mapped to the medical scan to populate some or all of the abnormality location data 443 for use by one or more other subsystems 101 and/or client devices 120. Furthermore, determining whether or not an abnormality exists in the detection step 1372 can be used to populate some or all of the diagnosis data 440 of the medical scan, for example, to indicate that the scan is normal or contains an abnormality in the diagnosis data 440.

An abnormality classification step 1374 can be performed on a medical scan in response to determining an abnormality is present. Classification data 1375 corresponding to one or more classification categories such as abnormality size, volume, pre-post contract, doubling time, calcification, components, smoothness, texture, diagnosis data, one or more medical codes, a malignancy rating such as a Lung-RADS score, or other classifying data as described herein can be determined based on the detected abnormality. The classification data 1375 generated by the abnormality classification step 1374 can be mapped to the medical scan to populate some or all of the abnormality classification data 445 of the corresponding abnormality classifier categories 444 and/or abnormality pattern categories 446 and/or to determine one or more medical codes 447 of the medical scan. The abnormality classification step 1374 can include performing an abnormality classification function on the full medical scan, or the abnormality region 1373 determined in the detection step 1372. The abnormality classification function can be based on another model trained on abnormality data such as a support vector machine model, another neural network model, or any supervised classification model trained on medical scans, or portions of medical scans, that include known abnormality classifying data to generate inference data for some or all of the classification categories. For example, the abnormality classification function can include another medical scan analysis function. Classification data 1375 in each of a plurality of classification categories can also be assigned their own calculated confidence score, which can also be generated by utilizing the abnormality classification function. Output to the abnormality classification function can also include at least one identified similar medical scan and/or at least one identified similar cropped image, for example, based on the training data. The abnormality classification step can also be included in the inference step 1354, where the inferred output vector or other inference data 1370 of the medical scan image analysis function includes the classification data 1375.

The abnormality classification function can be trained on full medical scans and/or one or more cropped or full selected image slices from medical scans that contain an abnormality. For example, the abnormality classification function can be trained on a set of two-dimensional cropped image slices that include abnormalities. The selected image slices and/or the cropped region in each selected image slice for each scan in the training set can be automatically selected based upon the known location of the abnormality. Input to the abnormality classification function can include the full medical scan, one or more selected full image slices, and/or one or more selected image slices cropped based on a selected region. Thus, the abnormality classification step can include automatically selecting one or more image slices that include the detected abnormality. The slice selection can include selecting the center slice in a set of consecutive slices that are determined to include the abnormality or selecting a slice that has the largest cross-section of the abnormality, or selecting one or more slices based on other criteria. The abnormality classification step can also include automatically generating one or more cropped two-dimensional images corresponding to the one or more of the selected image slices based on an automatically selected region that includes the abnormality.

Input to the abnormality classification function can also include other data associated with the medical scan, including patient history, risk factors, or other metadata. The abnormality classification step can also include determining some or all of the characteristics based on data of the medical scan itself. For example, the abnormality size and volume can be determined based on a number of pixels determined to be part of the detected abnormality. Other classifiers such as abnormality texture and/or smoothness can be determined by performing one or more other pre-processing functions on the image specifically designed to characterize such features. Such preprocessed characteristics can be included in the input to the abnormality classification function to the more difficult task of assigning a medical code or generating other diagnosis data. The training data can also be preprocessed to include such preprocessed features.

A similar scan identification step 1376 can also be performed on a medical scan with a detected abnormality and/or can be performed on the abnormality region 1373 determined in the detection step 1372. The similar scan identification step 1376 can include generating similar abnormality data 1377, for example, by identifying one or more similar medical scans or one or more similar cropped two-dimensional images from a database of medical scans and/or database of cropped two-dimensional images. Similar medical scans and/or cropped images can include medical scans or cropped images that are visually similar, medical scans or cropped images that have known abnormalities in a similar location to an inferred abnormality location of the given medical scan, medical scans that have known abnormalities with similar characteristics to inferred characteristics of an abnormality in the given scan, medical scans with similar patient history and/or similar risk factors, or some combination of these factors and/or other known and/or inferred factors. The similar abnormality data 1377 can be mapped to the medical scan to populate some or all of its corresponding similar scan data 480 for use by one or more other subsystems 101 and/or client devices 120.

The similar scans identification step 1376 can include performing a scan similarity algorithm, which can include generating a feature vector for the given medical scan and for medical scans in the set of medical scans, where the feature vector can be generated based on quantitative and/or category based visual features, inferred features, abnormality location and/or characteristics such as the predetermined size and/or volume, patient history and/or risk factor features, or other known or inferred features. A medical scan similarity analysis function can be applied to the feature vector of the given medical scan and one or more feature vectors of medical scans in the set. The medical scan similarity analysis function can include computing a similarity distance such as the Euclidian distance between the feature vectors, and assigning the similarity distance to the corresponding medical scan in the set. Similar medical scans can be identified based on determining one or more medical scans in the set with a smallest computed similarity distance, based on ranking medical scans in the set based on the computed similarity distances and identifying a designated number of top ranked medical scans, and/or based on determining if a similarity distance between the given medical scan and a medical scan in the set is smaller than a similarity threshold. Similar medical scans can also be identified based on determining medical scans in a database that mapped to a medical code that matches the medical code of the medical scan, or mapped to other matching classifying data. A set of identified similar medical scans can also be filtered based on other inputted or automatically generated criteria, where for example only medical scans with reliable diagnosis data or rich patient reports, medical scans with corresponding with longitudinal data in the patient file such as multiple subsequent scans taken at later dates, medical scans with patient data that corresponds to risk factors of the given patient, or other identified criteria, where only a subset of scans that compare favorably to the criteria are selected from the set and/or only a highest ranked single scan or subset of scans are selected from the set, where the ranking is automatically computed based on the criteria. Filtering the similar scans in this fashion can include calculating, or can be based on previously calculated, one or more scores as discussed herein. For example, the ranking can be based on a longitudinal quality score, such as the longitudinal quality score 434, which can be calculated for an identified medical scan based on a number of subsequent and/or previous scans for the patient. Alternatively or in addition, the ranking can be based on a confidence score associated with diagnosis data of the scan, such as confidence score data 460, based on performance score data associated with a user or medical entity associated with the scan, based on an amount of patient history data or data in the medical scan entry 352, or other quality factors. The identified similar medical scans can be filtered based on ranking the scans based on their quality score and/or based on comparing their quality score to a quality score threshold. In some embodiments, a longitudinal threshold must be reached, and only scans that compare favorably to the longitudinal threshold will be selected. For example, only scans with at least three scans on file for the patient and final biopsy data will be included.

In some embodiments, the similarity algorithm can be utilized in addition to or instead of the trained abnormality classification function to determine some or all of the inferred classification data 1375 of the medical scan, based on the classification data such as abnormality classification data 445 or other diagnosis data 440 mapped to one or more of the identified similar scans. In other embodiments, the similarity algorithm is merely used to identify similar scans for review by medical professionals to aid in review, diagnosis, and/or generating medical reports for the medical image.

A display parameter step 1378 can be performed based on the detection and/or classification of the abnormality. The display parameter step can include generating display parameter data 1379, which can include parameters that can be used by an interactive interface to best display each abnormality. The same or different display parameters can be generated for each abnormality. The display parameter data generated in the display parameter step 1378 can be mapped to the medical scan to populate some or all of its corresponding display parameter data 470 for use by one or more other subsystems 101 and/or client devices 120.

Performing the display parameter step 1378 can include selecting one or more image slices that include the abnormality by determining the one or more image slices that include the abnormality and/or determining one or more image slices that has a most optimal two-dimensional view of the abnormality, for example by selecting the center slice in a set of consecutive slices that are determined to include the abnormality, selecting a slice that has the largest cross-section of the abnormality, selecting a slice that includes a two-dimensional image of the abnormality that is most similar to a selected most similar two-dimensional-image, selecting the slice that was used as input to the abnormality classification step and/or similar scan identification step, or based on other criteria. This can also include automatically cropping one or more selected image slices based on an identified region that includes the abnormality. This can also select an ideal Hounsfield window that best displays the abnormality. This can also include selecting other display parameters based on data generated by the medical scan interface evaluating system and based on the medical scan.

FIGS. 8A-8F illustrate embodiments of a medical picture archive integration system 2600. The medical picture archive integration system 2600 can provide integration support for a medical picture archive system 2620, such as a PACS that stores medical scans. The medical picture archive integration system 2600 can utilize model parameters received from a central server system 2640 via a network 2630 to perform an inference function on de-identified medical scans of medical scans received from the medical picture archive system 2620. The annotation data produced by performing the inference function can be transmitted back to the medical picture archive system. Furthermore, the annotation data and/or de-identified medical scans can be sent to the central server system 2640, and the central server system can train on this information to produce new and/or updated model parameters for transmission back to the medical picture archive integration system 2600 for use on subsequently received medical scans.

In various embodiments, medical picture archive integration system 2600 includes a de-identification system that includes a first memory designated for protected health information (PHI), operable to perform a de-identification function on a DICOM image, received from a medical picture archive system, to identify at least one patient identifier and generate a de-identified medical scan that does not include the at least one patient identifier. The medical picture archive integration system further includes a de-identified image storage system that stores the de-identified medical scan in a second memory that is separate from the first memory, and an annotating system, operable to utilize model parameters received from a central server to perform an inference function on the de-identified medical scan, retrieved from the second memory to generate annotation data for transmission to the medical picture archive system as an annotated DICOM file.

The first memory and the second memory can be implemented by utilizing separate storage systems: the first memory can be implemented by a first storage system designated for PHI storage, and the second memory can be implemented by a second storage system designated for storage of de-identified data. The first storage system can be protected from access by the annotating system, while the second storage system can be accessible by the annotating system. The medical picture archive integration system 2600 can be operable to perform the de-identification function on data in first storage system to generate de-identified data. The de-identified data can then be stored in the second storage system for access by the annotating system. The first and second storage systems can be physically separate, each utilizing at least one of their own, separate memory devices. Alternatively, the first and second storage systems can be virtually separate, where data is stored in separate virtual memory locations on the same set of memory devices. Firewalls, virtual machines, and/or other protected containerization can be utilized to enforce the separation of data in each storage system, to protect the first storage system from access by the annotating system and/or from other unauthorized access, and/or to ensure that only data of the first storage system that has been properly de-identified through application of the de-identification function can be stored in the second storage system.

Figure 8A:
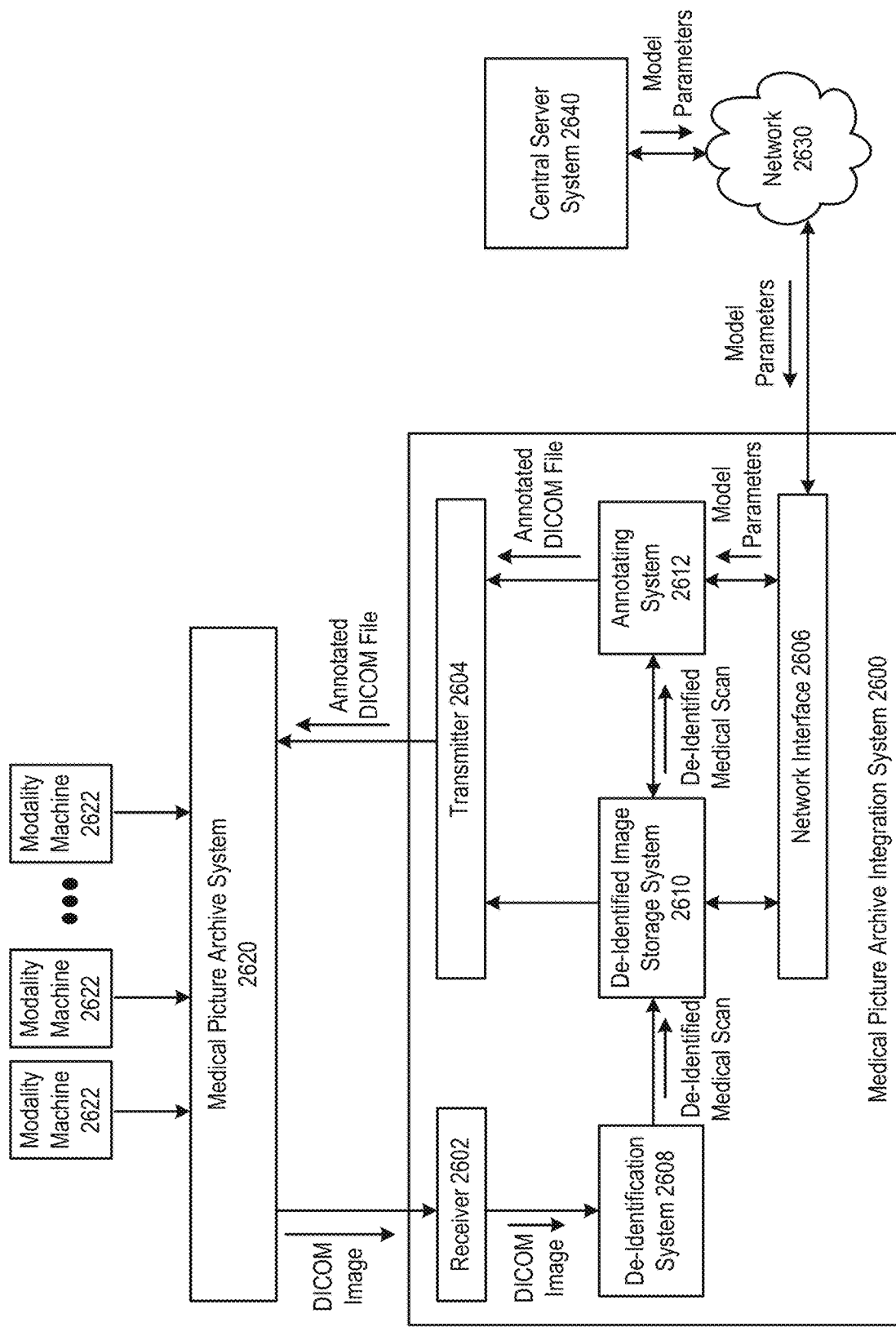
FIGS. 8A-8F are schematic block diagrams of a medical picture archive integration system in accordance with various embodiments.

As shown in FIG. 8A, the medical picture archive system 2620 can receive image data from a plurality of modality machines 2622, such as CT machines, MRI machines, x-ray machines, and/or other medical imaging machines that produce medical scans. The medical picture archive system 2620 can store this image data in a DICOM image format and/or can store the image data in a plurality of medical scan entries 352 as described in conjunction with some or all of the attributes described in conjunction with FIGS. 4A and 4B. While "DICOM image" will be used herein to refer to medical scans stored by the medical picture archive system 2620, the medical picture archive integration system 2600 can provide integration support for medical picture archive systems 2620 that store medical scans in other formats.

The medical picture archive integration system 2600 can include a receiver 2602 and a transmitter 2604, operable to transmit and receive data from the medical picture archive system 2620, respectively. For example, the receiver 2602 and transmitter 2604 can be configured to receive and transmit data, respectively, in accordance with a DICOM communication protocol and/or another communication protocol recognized by the medical picture archive system 2620. The receiver can receive DICOM images from the medical picture archive system 2620. The transmitter 2604 can send annotated DICOM files to the medical picture archive system 2620.

DICOM images received via receiver 2602 can be sent directly to a de-identification system 2608. The de-identification system 2608 can be operable to perform a de-identification function on the first DICOM image to identify at least one patient identifier in the DICOM image, and to generate a de-identified medical scan that does not include the identified at least one patient identifier. As used herein, a patient identifier can include any patient identifying data in the image data, header, and/or metadata of a medical scan, such as a patient ID number or other unique patient identifier, an accession number, a service-object pair (SOP) instance unique identifier (UID) field, scan date and/or time that can be used to determine the identity of the patient that was scanned at that date and/or time, and/or other private data corresponding to the patient, doctor, or hospital. In some embodiments, the de-identified medical scan is still in a DICOM image format. For example, a duplicate DICOM image that does not include the patient identifiers can be generated, and/or the original DICOM image can be altered such that the patient identifiers of the new DICOM image are masked, obfuscated, removed, replaced with a custom fiducial, and/or otherwise anonymized. In other embodiments, the de-identified medical scan is formatted in accordance with a different image format and/or different data format that does not include the identifying information. In some embodiments, other private information, for example, associated with a particular doctor or other medical professional, can be identified and anonymized as well.

Some patient identifying information can be included in a DICOM header of the DICOM image, for example, in designated fields for patient identifiers. These corresponding fields can be anonymized within the corresponding DICOM header field. Other patient identifying information can be included in the image itself, such as in medical scan image data 410. For example, the image data can include a patient name or other identifier that was handwritten on a hard copy of the image before the image was digitized. As another example, a hospital administered armband or other visual patient information in the vicinity of the patient may have been captured in the image itself. A computer vision model can detect the presence of these identifiers for anonymization, for example, where a new DICOM image includes a fiducial image that covers the identifying portion of the original DICOM image. In some embodiments, patient information identified in the DICOM header can be utilized to detect corresponding patient information in the image itself. For example, a patient name extracted from the DICOM header before anonymization can be used to search for the patient name in the image and/or to detect a location of the image that includes the patient name. In some embodiments, the de-identification system 2608 is implemented by the de-identification system discussed in conjunction with FIGS. 10A, 10B and 11, and/or utilizes functions and/or operations discussed in conjunction with FIGS. 10A, 10B and 11.

The de-identified medical scan can be stored in de-identified image storage system 2610 and the annotating system 2612 can access the de-identified medical scan from the de-identified image storage system 2610 for processing. The de-identified storage system can archive a plurality of de-identified DICOM images and/or can serve as temporary storage for the de-identified medical scan until processing of the de-identified medical scan by the annotating system 2612 is complete. The annotating system 2612 can generate annotation data by performing an inference function on the de-identified medical scan, utilizing the model parameters received from the central server system 2640. The annotation data can correspond to some or all of the diagnosis data 440 as discussed in conjunction with FIGS. 4A and 4B. In come embodiments, the annotating system 2612 can utilize the model parameters to perform inference step 1354, the detection step 1372, the abnormality classification step 1374, the similar scan identification step 1376, and/or the display parameter step 1378 of the medical scan image analysis system 112, as discussed in conjunction with FIG. 7B, on de-identified medical scans received from the medical picture archive system 2620.

In some embodiments, model parameters for a plurality of inference functions can be received from the central server system 2640, for example, where each inference function corresponds to one of a set of different scan categories. Each scan category can correspond to a unique combination of one or a plurality of scan modalities, one of a plurality of anatomical regions, and/or other scan classifier data 420. For example, a first inference function can be trained on and intended for de-identified medical scans corresponding chest CT scans, and a second inference function can be trained on and intended for de-identified medical scans corresponding to head MM scans. The annotating system can select one of the set of inference functions based on determining the scan category of the DICOM image, indicated in the de-identified medical scan, and selecting the inference function that corresponds to the determined scan category.

To ensure that scans received from the medical picture archive system 2620 match the set of scan categories for which the annotating system is operable to perform a corresponding inference function, the transmitter can transmit requests, such as DICOM queries, indicating image type parameters such as parameters corresponding to scan classifier data 420, for example indicating one or more scan modalities, one or more anatomical regions, and/or other parameters. For example, the request can indicate that all incoming scans that match the set of scan categories corresponding to a set of inference functions the annotating system 2612 for which the annotating system has obtained model parameters from the central server system 2640 and is operable to perform.

Once the annotation data is generated by performing the selected inference function, the annotating system 2612 can generate an annotated DICOM file for transmission to the medical picture archive system 2620 for storage. The annotated DICOM file can include some or all of the fields of the diagnosis data 440 and/or abnormality annotation data 442 of FIGS. 4A and 4B. The annotated DICOM file can include scan overlay data, providing location data of an identified abnormality and/or display data that can be used in conjunction with the original DICOM image to indicate the abnormality visually in the DICOM image and/or to otherwise visually present the annotation data, for example, for use with the medical scan assisted review system 102. For example, a DICOM presentation state file can be generated to indicate the location of an abnormality identified in the de-identified medical scan. The DICOM presentation state file can include an identifier of the original DICOM image, for example, in metadata of the DICOM presentation state file, to link the annotation data to the original DICOM image. In other embodiments, a full, duplicate DICOM image is generated that includes the annotation data with an identifier linking this duplicate annotated DICOM image to the original DICOM image.

The identifier linking the annotated DICOM file to the original DICOM image can be extracted from the original DICOM file by the de-identification system 2608, thus enabling the medical picture archive system 2620 to link the annotated DICOM file to the original DICOM image in its storage. For example, the de-identified medical scan can include an identifier that links the de-identified medical scan to the original DICOM file, but does not link the de-identified medical scan to a patient identifier or other private data.

In some embodiments, generating the annotated DICOM file includes altering one or more fields of the original DICOM header. For example, standardized header formatting function parameters can be received from the central server system and can be utilized by the annotating system to alter the original DICOM header to match a standardized DICOM header format. The standardized header formatting function can be trained in a similar fashion to other medical scan analysis functions discussed herein and/or can be characterized by some or all fields of a medical scan analysis function entry 356. The annotating system can perform the standardized header formatting function on a de-identified medical scan to generate a new, standardized DICOM header for the medical scan to be sent back to the medical picture archive system 2620 in the annotated DICOM file and/or to replace the header of the original DICOM file. The standardized header formatting function can be run in addition to other inference functions utilized to generate annotation data. In other embodiments, the medical picture archive integration system 2600 is implemented primarily for header standardization for medical scans stored by the medical picture archive system 2620. In such embodiments, only the standardized header formatting function is performed on the de-identified data to generate a modified DICOM header for the original DICOM image, but the de-identified medical scan is not annotated.

In some embodiments of header standardization, the annotation system can store a set of acceptable, standardized entries for some or all of the DICOM header fields, and can select one of the set of acceptable, standardized entries in populating one or more fields of the new DICOM header for the annotated DICOM file. For example, each of the set of scan categories determined by the annotating system can correspond to a standardized entry of one or more fields of the DICOM header. The new DICOM header can thus be populated based on the determined scan category.

In some embodiments, each of the set of standardized entries can be mapped to a set of related, non-standardized entries, such as entries in a different order, commonly misspelled entries, or other similar entries that do not follow a standardized format. For example, one of the set of acceptable, standardized entries for a field corresponding to a scan category can include "Chest CT", which can be mapped to a set of similar, non-standardized entries which can include "CT chest", "computerized topography CT", and/or other entries that are not standardized. In such embodiments, the annotating system can determine the original DICOM header is one of the similar non-standardized entries, and can select the mapped, standardized entry as the entry for the modified DICOM header. In other embodiments, the image data itself and/or or other header data can be utilized by the annotation system to determine a standardized field. For example, an input quality assurance function 1106 can be trained by the central server system and sent to the annotating system to determine one or more appropriate scan classifier fields, or one or more other DICOM header fields, based on the image data or other data of the de-identified medical scan. One or more standardized labels can be assigned to corresponding fields of the modified DICOM header based on the one or more fields determined by the input quality assurance function.

In some embodiments, the DICOM header is modified based on the annotation data generated in performing the inference function. In particular, a DICOM priority header field can be generated and/or modified automatically based on the severity and/or time-sensitivity of the abnormalities detected in performing the inference function. For example, a DICOM priority header field can be changed from a low priority to a high priority in response to annotation data indicating a brain bleed in the de-identified medical scan of a DICOM image corresponding to a head CT scan, and a new DICOM header that includes the high priority DICOM priority header field can be sent back to the medical picture archive system 2620 to replace or otherwise be mapped to the original DICOM image of the head CT scan.

In some embodiments, some or all of this DICOM header altering is performed by utilizing the medical scan header standardization system of FIGS. 12A-12F. Some or all of the steps and/or functionality described in conjunction with the medical scan header standardization system of FIGS. 12A-12F can be utilized by the annotating system 2612.

In various embodiments, the medical picture archive system 2620 is disconnected from network 2630, for example, to comply with requirements regarding Protected Health Information (PHI), such as patient identifiers and other private patient information included in the DICOM images and/or otherwise stored by the medical picture archive system 2620. The medical picture archive integration system 2600 can enable processing of DICOM images while still protecting private patient information by first de-identifying DICOM data by utilizing de-identification system 2608. The de-identification system 2608 can utilize designated processors and memory of the medical picture archive integration system, for example, designated for PHI. The de-identification system 2608 can be decoupled from the network 2630 to prevent the DICOM images that still include patient identifiers from being accessed via the network 2630. For example, as shown in FIG. 8A, the de-identification system 2608 is not connected to network interface 2606. Furthermore, only the de-identification system 2608 has access to the original DICOM files received from the medical picture archive system 2620 via receiver 2602. The de-identified image storage system 2610 and annotating system 2612, as they are connected to network 2630 via network interface 2606, only store and have access to the de-identified medical scan produced by the de-identification system 2608.

Figure 8B:
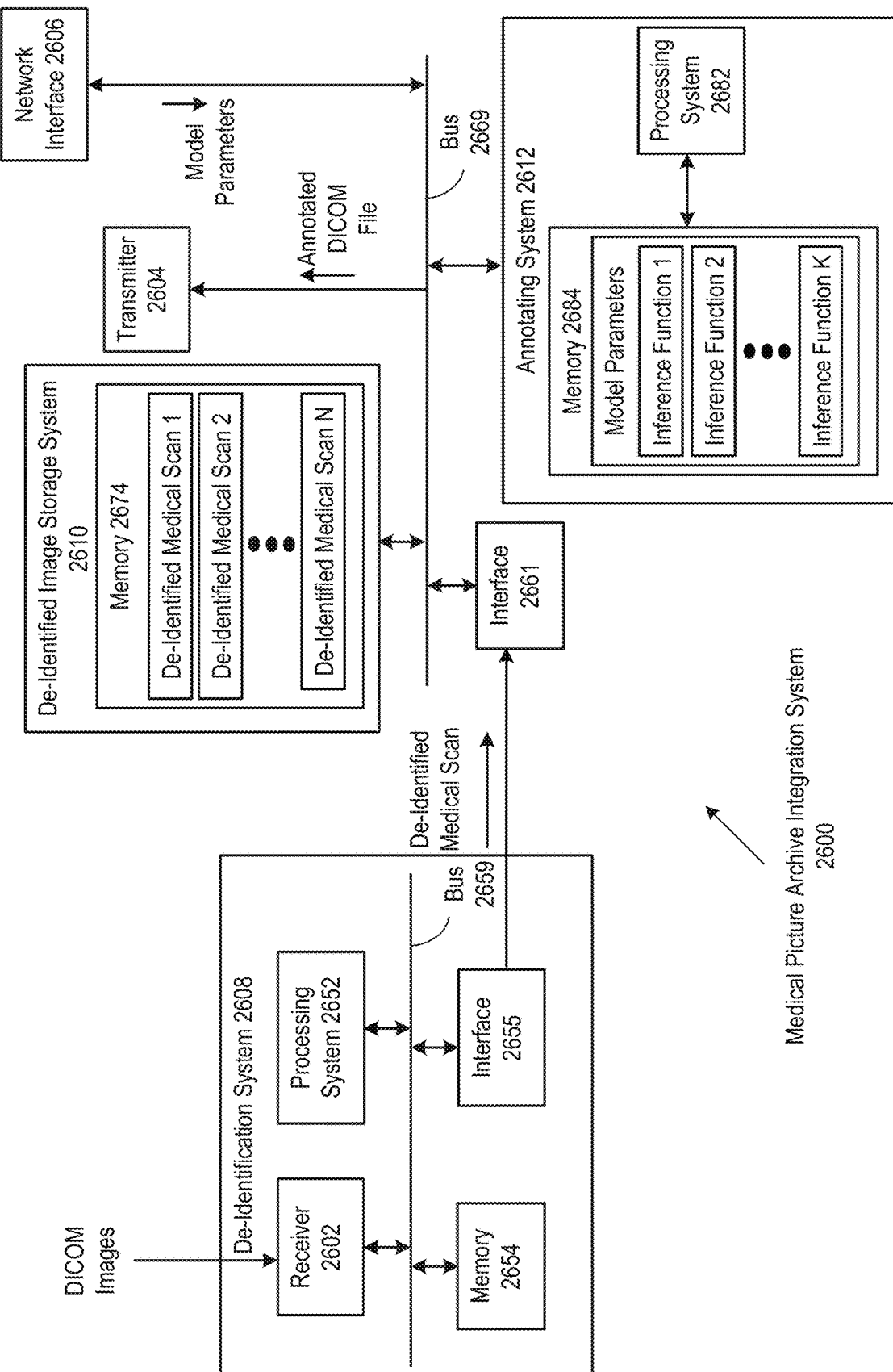

This containerization that separates the de-identification system 2608 from the de-identified image storage system 2610 and the annotating system 2612 is further illustrated in FIG. 8B, which presents an embodiment of the medical picture archive integration system 2600. The de-identification system 2608 can include its own designated memory 2654 and processing system 2652, connected to receiver 2602 via bus 2659. For example, this memory 2654 and processing system 2652 can be designated for PHI, and can adhere to requirements for handling PHI. The memory 2654 can store executable instructions that, when executed by the processing system 2652, enable the de-identification system to perform the de-identification function on DICOM images received via receiver 2602 of the de-identification system. The incoming DICOM images can be temporarily stored in memory 2654 for processing, and patient identifiers detected in performing the de-identification function can be temporarily stored in memory 2654 to undergo anonymization. Interface 2655 can transmit the de-identified medical scan to interface 2661 for use by the de-identified image storage system 2610 and the annotating system 2612. Interface 2655 can be protected from transmitting original DICOM files and can be designated for transmission of de-identified medical scan only.

Bus 2669 connects interface 2661, as well as transmitter 2604 and network interface 2606, to the de-identified image storage system 2610 and the annotating system 2612. The de-identified image storage system 2610 and annotating system 2612 can utilize separate processors and memory, or can utilize shared processors and/or memory. For example, the de-identified image storage system 2610 can serve as temporary memory of the annotating system 2612 as de-identified images are received and processed to generate annotation data.

As depicted in FIG. 8B, the de-identified image storage system 2610 can include memory 2674 that can temporarily store incoming de-identified medical scans as it undergoes processing by the annotating system 2612 and/or can archive a plurality of de-identified medical scans corresponding to a plurality of DICOM images received by the medical picture archive integration system 2600. The annotating system 2612 can include a memory 2684 that stores executable instructions that, when executed by processing system 2682, cause the annotating system 2612 perform a first inference function on de-identified medical scan to generate annotation data by utilizing the model parameters received via interface 2606, and to generate an annotated DICOM file based on the annotation data for transmission via transmitter 2604. The model parameters can be stored in memory 2684, and can include model parameters for a plurality of inference functions, for example, corresponding to a set of different scan categories.

The medical picture archive integration system can be an onsite system, installed at a first geographic site, such as a hospital or other medical entity that is affiliated with the medical picture archive system 2620. The hospital or other medical entity can further be responsible for the PHI of the de-identification system, for example, where the memory 2654 and processing system 2652 are owned by, maintained by, and/or otherwise affiliated with the hospital or other medical entity. The central server system 2640 can be located at a second, separate geographic site that is not affiliated with the hospital or other medical entity and/or at a separate geographic site that is not affiliated with the medical picture archive system 2620. The central server system 2640 can be a server configured to be outside the network firewall and/or out outside the physical security of the hospital or other medical entity or otherwise not covered by the particular administrative, physical and technical safeguards of the hospital or other medical entity.

Figure 8C:
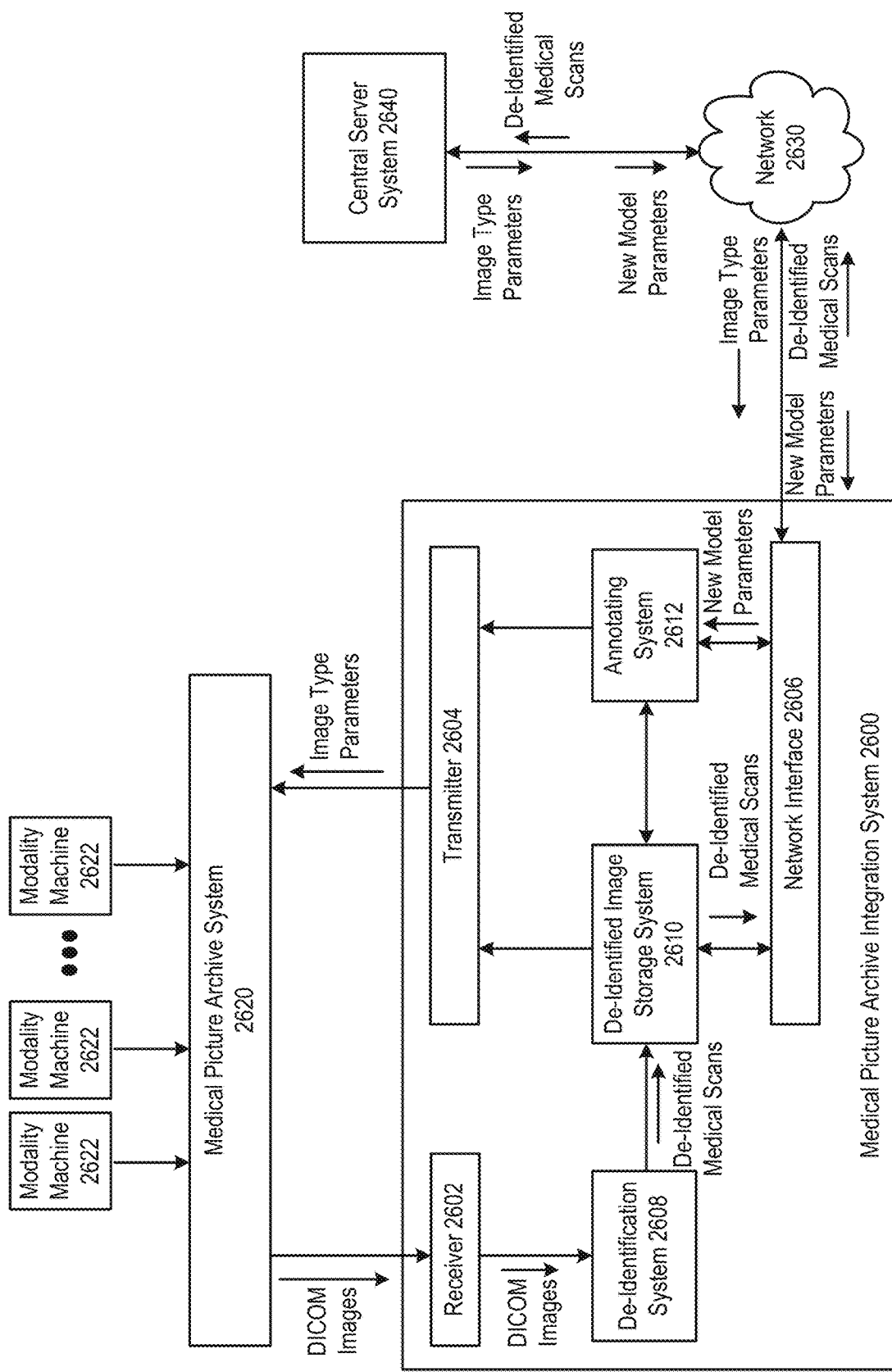

FIG. 8C further illustrates how model parameters can be updated over time to improve existing inference functions and/or to add new inference functions, for example corresponding to new scan categories. In particular, the some or all of the de-identified medical scans generated by the de-identification system 2608 can be transmitted back to the central server system, and the central server system 2640 can train on this data to improve existing models by producing updated model parameters of an existing inference function and/or to generate new models, for example, corresponding to new scan categories, by producing new model parameters for new inference functions. For example, the central server system 2640 can produce updated and/or new model parameters by performing the training step 1352 of the medical scan image analysis system 112, as discussed in conjunction with FIG. 7A, on a plurality of de-identified medical scans received from the medical picture archive integration system 2600.

The image type parameters can be determined by the central server system to dictate characteristics of the set of de-identified medical scans to be received to train and/or retrain the model. For example, the image type parameters can correspond to one or more scan categories, can indicate scan classifier data 420, and/or can indicate one or more scan modalities, one or more anatomical regions, a date range, and/or other parameters. The image type parameters can be determined by the central server system based on training parameters 620 determined for the corresponding inference function to be trained, and/or based on characteristics of a new and/or existing scan category corresponding to the inference function to be trained. The image type parameters can be sent to the medical picture archive integration system 2600, and a request such as a DICOM query can be sent to the medical picture archive system 2620, via transmitter 2604, that indicates the image type parameters. For example, the processing system 2682 can be utilized to generate the DICOM query based on the image type parameters received from the central server system 2640. The medical picture archive system can automatically transmit one or more DICOM images to the medical picture archive integration system in response to determining that the one or more DICOM images compares favorably to the image type parameters. The DICOM images received in response can be de-identified by the de-identification system 2608. In some embodiments, the de-identified medical scans can be transmitted directly to the central server system 2640, for example, without generating annotation data.

The central server system can generate the new and/or updated model parameters by training on the received set of de-identified medical scans, and can transmit the new and/or updated model parameters to the de-identified storage system. If the model parameters correspond to a new inference function for a new scan category, the medical picture archive integration system 2600 can generate a request, such as a DICOM query, for transmission to the medical picture archive system indicating that incoming scans corresponding to image type parameters corresponding to the new scan category be sent to the medical picture archive integration system. The annotating system can update the set of inference functions to include the new inference function, and the annotating system can select the new inference function from the set of inference functions for subsequently generated de-identified medical scans by the de-identification system by determining each of these de-identified medical scans indicate the corresponding DICOM image corresponds to the new scan category. The new model parameters can be utilized to perform the new inference function on each of these de-identified medical scans to generate corresponding annotation data, and an annotated DICOM file corresponding to each of these de-identified medical scans can be generated for transmission to the medical picture archive system via the transmitter.

In some embodiments, the central server system 2640 receives a plurality of de-identified medical scans from a plurality of medical picture archive integration system 2600, for example, each installed at a plurality of different hospitals or other medical entities, via the network 2630. The central server system can generate training sets by integrating de-identified medical scans from some or all of the plurality of medical picture archive integration systems 2600 to train one or more inference functions and generate model parameters. The plurality of medical picture archive integration systems 2600 can utilize the same set of inference functions or different sets of inference functions. In some embodiments, the set of inference functions utilized by the each of the plurality of medical picture archive systems 2620 are trained on different sets of training data. For example, the different sets of training data can correspond to the set of de-identified medical scans received from the corresponding medical picture archive integration system 2600.

In some embodiments, the medical scan diagnosing system 108 can be utilized to implement the annotating system 2612, where the corresponding subsystem processing device 235 and subsystem memory device 245 of the medical scan diagnosing system 108 are utilized to implement the processing system 2682 and the memory 2684, respectively. Rather than receiving the medical scans via the network 150 as discussed in conjunction with FIG. 6A, the medical scan diagnosing system 108 can perform a selected medical scan inference function 1105 on an incoming de-identified medical scan generated by the de-identification system 2608 and/or retrieved from the de-identified image storage system 2610. Memory 2684 can store the set of medical scan inference functions 1105, each corresponding to a scan category 1120, where the inference function is selected from the set based on determining the scan category of the de-identified medical scan and selecting the corresponding inference function. The processing system 2682 can perform the selected inference function 1105 to generate the inference data 1110, which can be further utilized by the annotating system 2612 to generate the annotated DICOM file for transmission back to the medical picture archive system 2620. New medical scan inference functions 1105 can be added to the set when corresponding model parameters are received from the central server system. The remediation step 1140 can be performed locally by the annotating system 2612 and/or can be performed by the central server system 2640 by utilizing one or more de-identified medical scans and corresponding annotation data sent to the central server system 2640. Updated model parameters can be generated by the central server system 2640 and sent to the medical picture archive integration system 2600 as a result of performing the remediation step 1140.

The central server system 2640 can be implemented by utilizing one or more of the medical scan subsystems 101, such as the medical scan image analysis system 112 and/or the medical scan diagnosing system 108, to produce model parameters for one or more inference functions. The central server system can store or otherwise communicate with a medical scan database 342 that includes the de-identified medical scans and/or annotation data received from one or more medical picture archive integration systems 2600. Some or all entries of the medical scan database 342 can be utilized to as training data to produce model parameters for one or more inference functions. These entries of the medical scan database 342 can be utilized by other subsystems 101 as discussed herein. For example, other subsystems 101 can utilize the central server system 2640 to fetch medical scans and/or corresponding annotation data that meet specified criteria. The central server system 2640 can query the medical picture archive integration system 2600 based on this criteria, and can receive de-identified medical scans and/or annotation data in response. This can be sent to the requesting subsystem 101 directly and/or can be added to the medical scan database 342 or another database of the database storage system 140 for access by the requesting subsystem 101.

Alternatively or in addition, the central server system 2640 can store or otherwise communicate with a user database 344 storing user profile entries corresponding to each of a plurality of medical entities that each utilize a corresponding one of a plurality of medical picture archive integration systems 2600. For example, basic user data corresponding to the medical entity can be stored as basic user data, a number of scans or other consumption information indicating usage of one or more inference functions by corresponding medical picture archive integration system can be stored as consumption usage data, and/or a number of scans or other contribution information indicating de-identified scans sent to the central server system as training data can be stored as contribution usage data. The user profile entry can also include inference function data, for example, with a list of model parameters or function identifiers, such as medical scan analysis function identifiers 357, of inference functions currently utilized by the corresponding medical picture archive integration system 2600. These entries of the user database 344 can be utilized by other subsystems 101 as discussed herein.

Alternatively or in addition, the central server system 2640 can store or otherwise communicate with a medical scan analysis function database 346 to store model parameters, training data, or other information for one or more inference functions as medical scan analysis function entries 356. In some embodiments, model parameter data 623 can indicate the model parameters and function classifier data 610 can indicate the scan category of inference function entries. In some embodiments, the medical scan analysis function entry 356 can further include usage identifying information indicating a medical picture archive integration system identifier, medical entity identifier, and/or otherwise indicating which medical archive integration systems and/or medical entities have received the corresponding model parameters to utilize the inference function corresponding to the medical scan analysis function entry 356. These entries of the medical scan analysis function database 346 can be utilized by other subsystems 101 as discussed herein.

In some embodiments, the de-identification function is a medical scan analysis function, for example, with a corresponding medical scan analysis function entry 356 in the medical scan analysis function database 346. In some embodiments, the de-identification function is trained by the central server system 2640. For example, the central server system 2640 can send de-identification function parameters to the medical picture archive integration system 2600 for use by the de-identification system 2608. In embodiments with a plurality of medical picture archive integration systems 2600, each of the plurality of medical picture archive integration systems 2600 can utilize the same or different de-identification functions. In some embodiments, the de-identification function utilized by the each of the plurality of medical picture archive integration systems 2600 are trained on different sets of training data. For example, the different sets of training data can correspond to each different set of de-identified medical scans received from each corresponding medical picture archive integration system 2600.

Figure 8D:
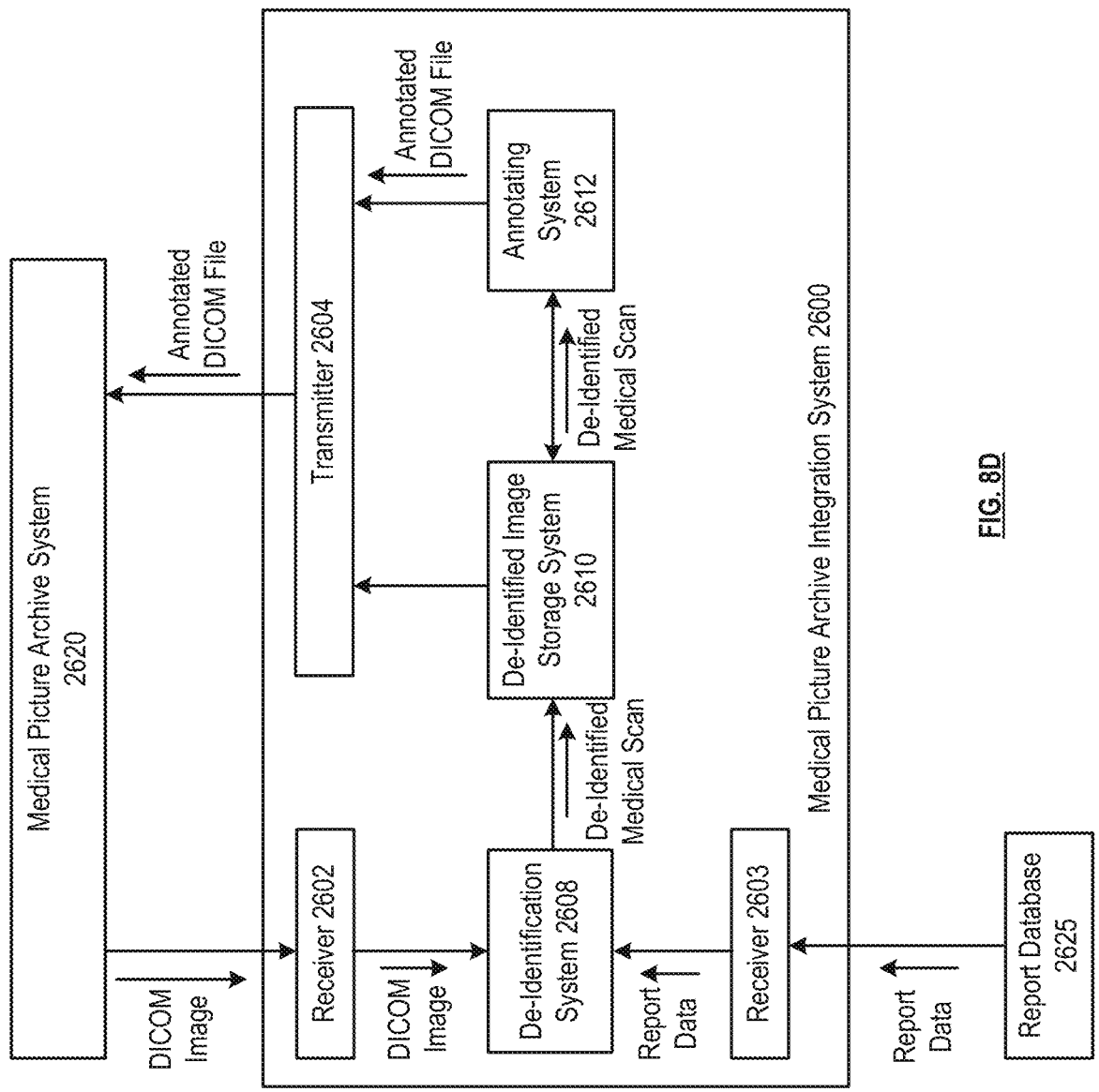
Figure 8E:
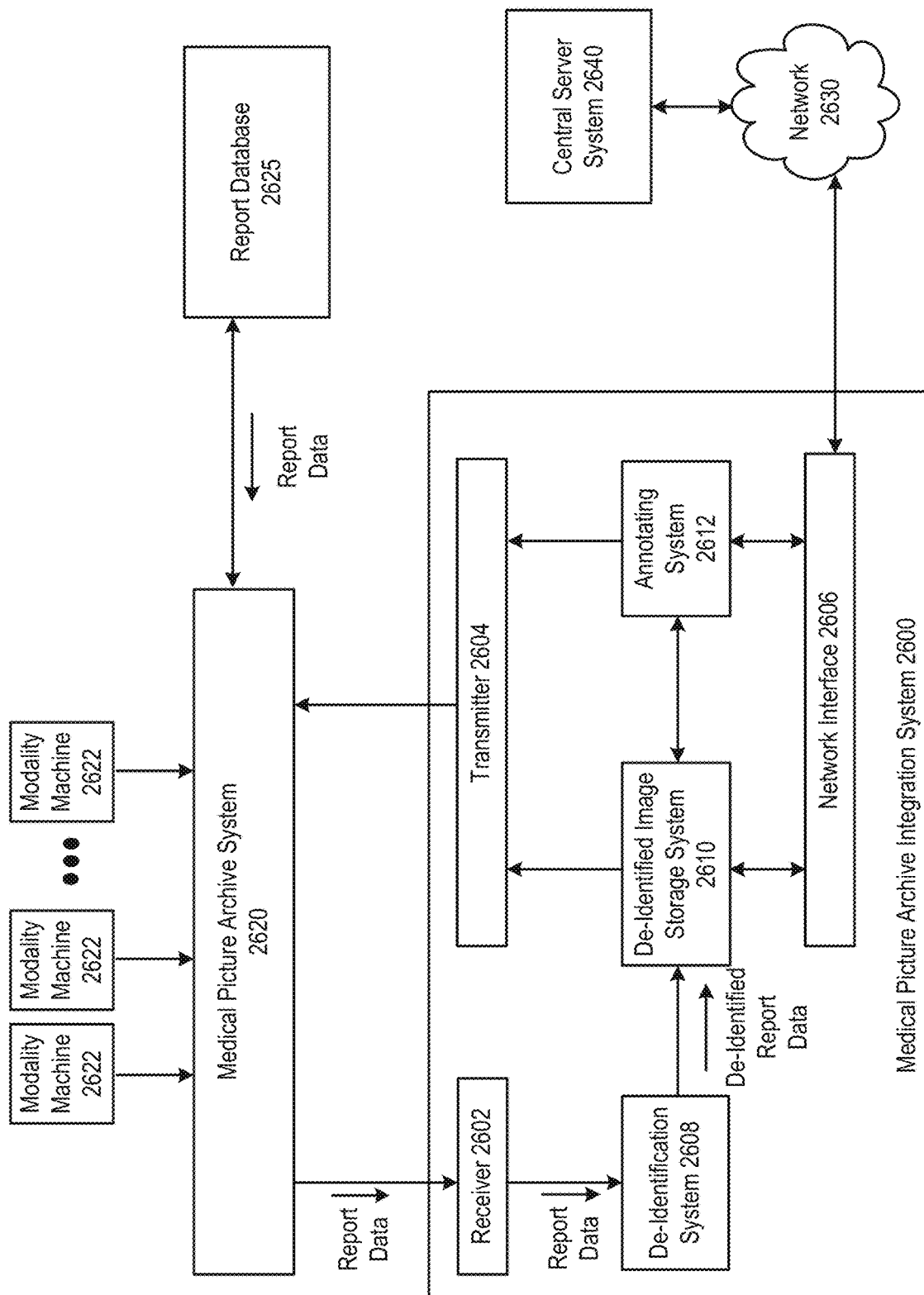
Figure 8F:
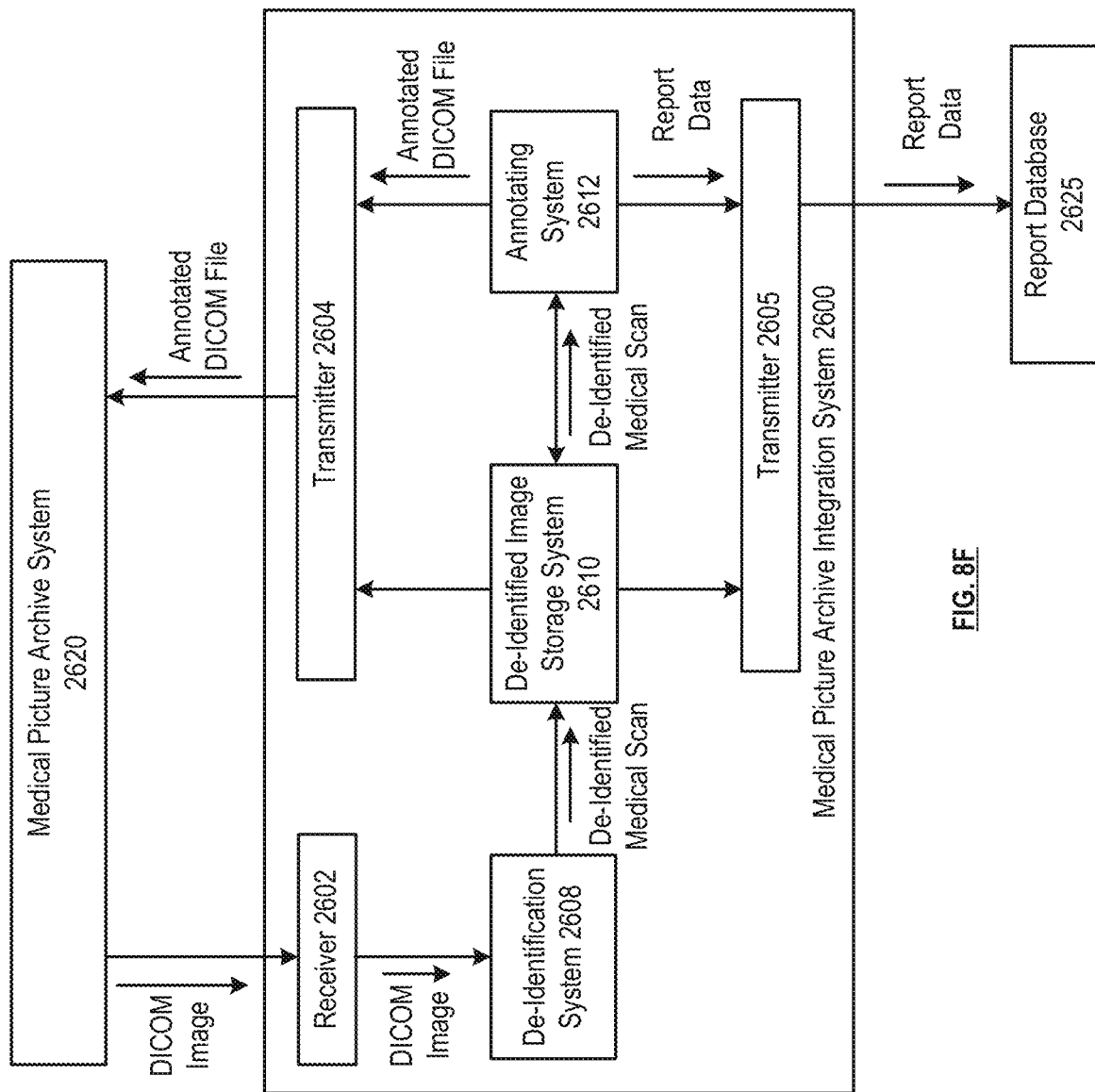

In some embodiments, as illustrated in FIGS. 8D-8F, the medical picture archive integration system 2600 can further communicate with a report database 2625, such as a Radiology Information System (RIS), that includes a plurality of medical reports corresponding to the DICOM images stored by the medical picture archive system 2620.

As shown in FIG. 8D, the medical picture archive integration system 2600 can further include a receiver 2603 that receives report data, corresponding to the DICOM image, from report database 2625. The report database 2625 can be affiliated with the medical picture archive system 2620 and can store report data corresponding to DICOM images stored in the medical picture archive system. The report data of report database 2625 can include PHI, and the report database 2625 can thus be disconnected from network 2630.

The report data can include natural language text, for example, generated by a radiologist that reviewed the corresponding DICOM image. The report data can be used to generate the de-identified medical scan, for example, where the de-identification system 2608 performs a natural language analysis function on the report data to identify patient identifying text in the report data. The de-identification system 2608 can utilize this patient identifying text to detect matching patient identifiers in the DICOM image to identify the patient identifiers of the DICOM image and generate the de-identified medical scan. In some embodiments, the report data can be de-identified by obfuscating, hashing, removing, replacing with a fiducial, or otherwise anonymizing the identified patient identifying text to generate de-identified report data.

The de-identified report data can be utilized by the annotating system 2612, for example, in conjunction with the DICOM image, to generate the annotation data. For example, the annotating system 2612 can perform a natural language analysis function on the de-identified natural language text of the report data to generate some or all of the annotation data. In some embodiments, the de-identified report data is sent to the central server system, for example, to be used as training data for inference functions, for natural language analysis functions, for other medical scan analysis functions, and/or for use by at least one other subsystem 101. For example, other subsystems 101 can utilize the central server system 2640 to fetch medical reports that correspond to particular medical scans or otherwise meet specified criteria. The central server system 2640 can query the medical picture archive integration system 2600 based on this criteria, and can receive de-identified medical reports in response. This can be sent to the requesting subsystem 101 directly, can be added to the medical scan database 342, a de-identified report database, or another database of the database storage system 140 for access by the requesting sub system 101.

In some embodiments the medical picture archive integration system 2600 can query the report database 2625 for the report data corresponding to a received DICOM image by utilizing a common identifier extracted from the DICOM image.

In some embodiments, the report data can correspond to a plurality of DICOM images. For example, the report data can include natural language text describing a plurality of medical scans of a patient that can include multiple sequences, multiple modalities, and/or multiple medical scans taken over time. In such embodiments, the patient identifying text and/or annotation data detected in the report data can also be applied to de-identify and/or generate annotation data for the plurality of DICOM images it describes. In such embodiments, the medical picture archive integration system 2600 can query the medical picture archive system 2620 for one or more additional DICOM images corresponding to the report data, and de-identified data and annotation data for these additional DICOM images can be generated accordingly by utilizing the report data.

In some embodiments, as shown in FIG. 8E, the medical picture archive system 2620 communicates with the report database 2625. The medical picture archive system 2620 can request the report data corresponding to the DICOM image from the report database 2625, and can transmit the report data to the medical picture archive integration system 2600 via a DICOM communication protocol for receipt via receiver 2602. The medical picture archive system 2620 can query the report database 2625 for the report data, utilizing a common identifier extracted from the corresponding DICOM image, in response to determining to send the corresponding DICOM image to the medical picture archive integration system 2600.

FIG. 8F presents an embodiment where report data is generated by the annotating system 2612 and is transmitted, via a transmitter 2605, to the report database 2625, for example via a DICOM communication protocol or other protocol recognized by the report database 2625. In other embodiments, the report data is instead transmitted via transmitter 2604 to the medical picture archive system 2620, and the medical picture archive system 2620 transmits the report data to the report database 2625.

The report data can be generated by the annotating system 2612 as output of performing the inference function on the de-identified medical scan. The report data can include natural language text data 448 generated automatically based on other diagnosis data 440 such as abnormality annotation data 442 determined by performing the inference function, for example, by utilizing a medical scan natural language generating function trained by the medical scan natural language analysis system 114. The report data can be generated instead of, or in addition to, the annotated DICOM file.

Figure 9:
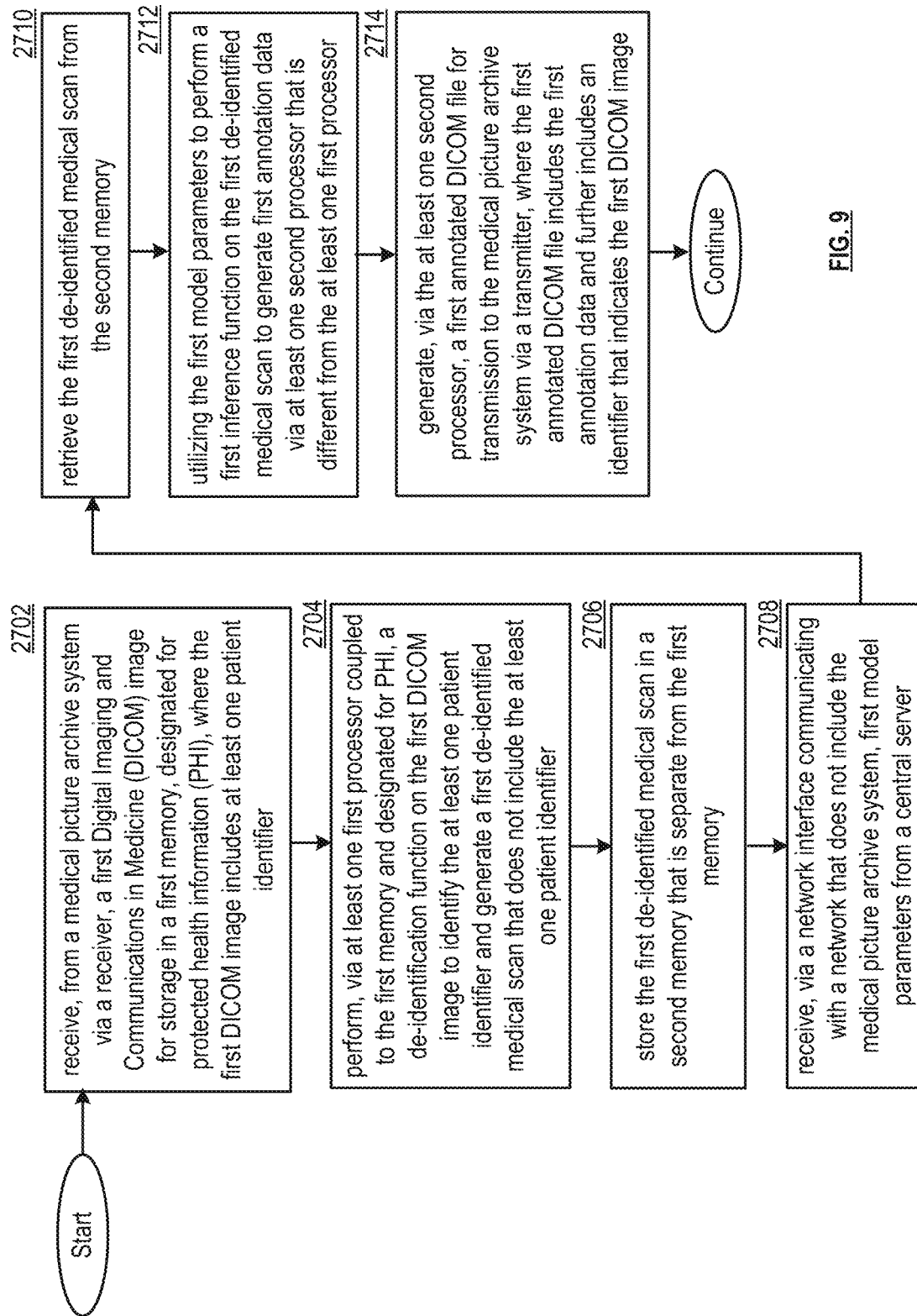
FIG. 9 is a flowchart representation of a method for execution by a medical picture archive integration system in accordance with various embodiments.

FIG. 9 presents a flowchart illustrating a method for execution by a medical picture archive integration system 2600 that includes a first memory and a second memory that store executional instructions that, when executed by at least one first processor and at least one second processor, respectfully, cause the medical picture archive integration system to perform the steps below. In various embodiments, the first memory and at least one first processor are implemented by utilizing, respectfully, the memory 2654 and processing system 2652 of FIG. 8B. In various embodiments, the second memory is implemented by utilizing the memory 2674 and/or the memory 2684 of FIG. 8B. In various embodiments, the at least one second processor is implemented by utilizing the processing system 2682 of FIG. 8B.

Step 2702 includes receiving, from a medical picture archive system via a receiver, a first DICOM image for storage in the first memory, designated for PHI, where the first DICOM image includes at least one patient identifier. Step 2704 includes performing, via at least one first processor coupled to the first memory and designated for PHI, a de-identification function on the first DICOM image to identify the at least one patient identifier and generate a first de-identified medical scan that does not include the at least one patient identifier.

Step 2706 includes storing the first de-identified medical scan in a second memory that is separate from the first memory. Step 2708 includes receiving, via a network interface communicating with a network that does not include the medical picture archive system, first model parameters from a central server.

Step 2710 includes retrieving the first de-identified medical scan from the second memory. Step 2712 includes utilizing the first model parameters to perform a first inference function on the first de-identified medical scan to generate first annotation data via at least one second processor that is different from the at least one first processor. Step 2714 includes generating, via the at least one second processor, a first annotated DICOM file for transmission to the medical picture archive system via a transmitter, where the first annotated DICOM file includes the first annotation data and further includes an identifier that indicates the first DICOM image. In various embodiments, the first annotated DICOM file is a DICOM presentation state file.

In various embodiments, the second memory further includes operational instructions that, when executed by the at least one second processor, further cause the medical picture archive integration system to retrieve a second de-identified medical scan from the de-identified image storage system, where the second de-identified medical scan was generated by the at least one first processor by performing the de-identification function on a second DICOM image received from the medical picture archive system. The updated model parameters are utilized to perform the first inference function on the second de-identified medical scan to generate second annotation data. A second annotated DICOM file is generated for transmission to the medical picture archive system via the transmitter, where the second annotated DICOM file includes the second annotation data and further includes an identifier that indicates the second DICOM image.

In various embodiments, the second memory stores a plurality of de-identified medical scans generated by the at least one first processor by performing the de-identification function on a corresponding plurality of DICOM images received from the medical picture archive system via the receiver. The plurality of de-identified medical scans is transmitted to the central server via the network interface, and the central server generates the first model parameters by performing a training function on training data that includes the plurality of de-identified medical scans.

In various embodiments, the central server generates the first model parameters by performing a training function on training data that includes a plurality of de-identified medical scans received from a plurality of medical picture archive integration systems via the network. Each of the plurality of medical picture archive integration systems communicates bidirectionally with a corresponding one of a plurality of medical picture archive systems, and the plurality of de-identified medical scans corresponds to a plurality of DICOM images stored by the plurality of medical picture archive integration systems.

In various embodiments, the first de-identified medical scan indicates a scan category of the first DICOM image. The second memory further stores operational instructions that, when executed by the at least one second processor, further cause the medical picture archive integration system to select the first inference function from a set of inference functions based on the scan category. The set of inference functions corresponds to a set of unique scan categories that includes the scan category. In various embodiments, each unique scan category of the set of unique scan categories is characterized by one of a plurality of modalities and one of a plurality of anatomical regions.

In various embodiments, the first memory further stores operational instructions that, when executed by the at least one first processor, further cause the medical picture archive integration system to receive a plurality of DICOM image data from the medical picture archive system via the receiver for storage in the first memory in response to a query transmitted to the medical picture archive system via the transmitter. The query is generated by the medical picture archive integration system in response to a request indicating a new scan category received from the central server via the network. The new scan category is not included in the set of unique scan categories, and the plurality of DICOM image data corresponds to the new scan category. The de-identification function is performed on the plurality of DICOM image data to generate a plurality of de-identified medical scans for transmission to the central server via the network.

The second memory further stores operational instructions that, when executed by the at least one second processor, further cause the medical picture archive integration system to receive second model parameters from the central server via the network for a new inference function corresponding to the new scan category. The set of inference functions is updated to include the new inference function. The second de-identified medical scan is retrieved from the first memory, where the second de-identified medical scan was generated by the at least one first processor by performing the de-identification function on a second DICOM image received from the medical picture archive system. The new inference function is selected from the set of inference functions by determining the second de-identified medical scan indicates the second DICOM image corresponds to the new scan category. The second model parameters are utilized to perform the new inference function on the second de-identified medical scan to generate second annotation data. A second annotated DICOM file is generated for transmission to the medical picture archive system via the transmitter, where the second annotated DICOM file includes the second annotation data and further includes an identifier that indicates the second DICOM image.

In various embodiments, the medical picture archive integration system generates parameter data for transmission to the medical picture archive system that indicates the set of unique scan categories. The medical picture archive system automatically transmits the first DICOM image to the medical picture archive integration system in response to determining that the first DICOM image compares favorably to one of the set of unique scan categories.

In various embodiments, the second memory further stores operational instructions that, when executed by the at least one second processor, cause the medical picture archive integration system to generate a natural language report data is based on the first annotation data and to transmit, via a second transmitter, the natural language report data to a report database associated with the medical picture archive integration system, where the natural language report data includes an identifier corresponding to the first DICOM image.

In various embodiments, the first memory further stores operational instructions that, when executed by the at least one first processor, cause the medical picture archive integration system to receive, via a second receiver, a natural language report corresponding to the first DICOM image from the report database. A set of patient identifying text included in the natural language report are identified. Performing the de-identification function on the first DICOM image includes searching the first DICOM image for the set of patient identifying text to identify the at least one patient identifier.

In various embodiments, the first memory is managed by a medical entity associated with the medical picture archive system. The medical picture archive integration system is located at a first geographic site corresponding to the medical entity, and the central server is located at a second geographic site. In various embodiments, the first memory is decoupled from the network to prevent the first DICOM image that includes the at least one patient identifier from being communicated via the network. In various embodiments, the medical picture archive system is a Picture Archive and Communication System (PACS) server, and the first DICOM image is received in response to a query sent to the medical picture archive system by the transmitter in accordance with a DICOM communication protocol.

Figure 10A:
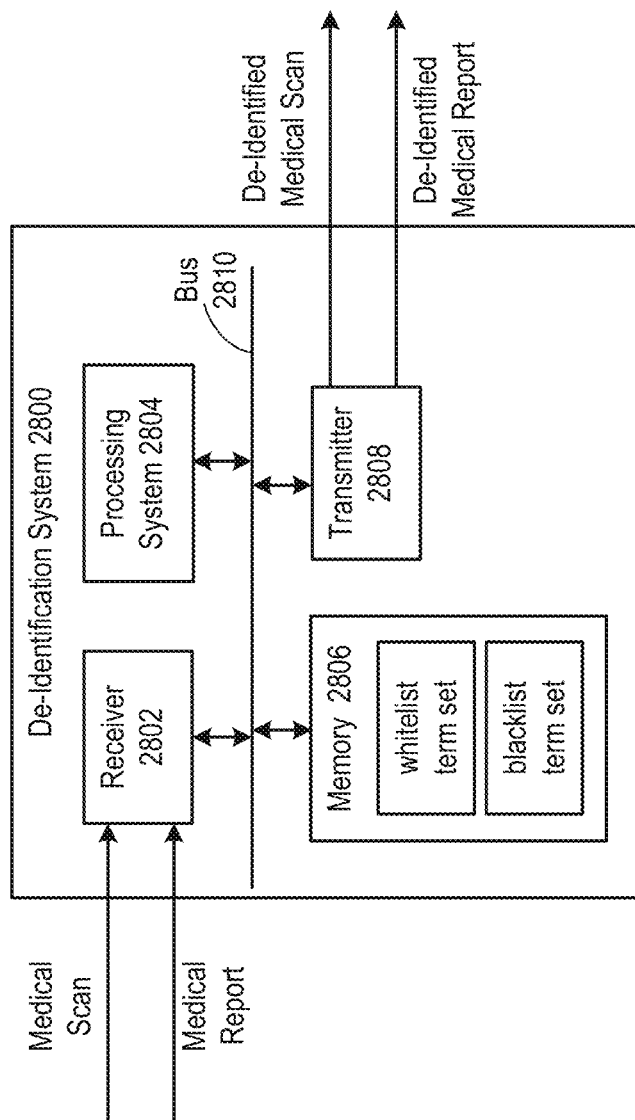
FIG. 10A is a schematic block diagram of a de-identification system in accordance with various embodiments.

FIG. 10A presents an embodiment of a de-identification system 2800. The de-identification system 2800 can be utilized to implement the de-identification system 2608 of FIGS. 8A-8F. In some embodiments, the de-identification system 2800 can be utilized by other subsystems to de-identify image data, medical report data, private fields of medical scan entries 352 such as patient identifier data 431, and/or other private fields stored in databases of the database memory device 340.

The de-identification system can be operable to receive, from at least one first entity, a medical scan and a medical report corresponding to the medical scan. A set of patient identifiers can be identified in a subset of fields of a header of the medical scan. A header anonymization function can be performed on each of the set of patient identifiers to generate a corresponding set of anonymized fields. A de-identified medical scan can be generated by replacing the subset of fields of the header of the medical scan with the corresponding set of anonymized fields.

A subset of patient identifiers of the set of patient identifiers can be identified in the medical report by searching text of the medical report for the set of patient identifiers. A text anonymization function can be performed on the subset of patient identifiers to generate corresponding anonymized placeholder text for each of the subset of patient identifiers. A de-identified medical report can be generated by replacing each of the subset of patient identifiers with the corresponding anonymized placeholder text. The de-identified medical scan and the de-identified medical report can be transmitted to a second entity via a network.

As shown in FIG. 10A, the de-identification system 2800 can include at least one receiver 2802 operable to receive medical scans, such as medical scans in a DICOM image format. The at least one receiver 2802 is further operable to receive medical reports, such as report data 449 or other reports containing natural language text diagnosing, describing, or otherwise associated the medical scans received by the de-identification system. The medical scans and report data can be received from the same or different entity, and can be received by the same or different receiver 2802 in accordance with the same or different communication protocol. For example, the medical scans can be received from the medical picture archive system 2620 of FIGS. 8A-8F and the report data can be received from the report database 2625 of FIGS. 8D-8F. In such embodiments, the receiver 2802 can be utilized to implement the receiver 2602 of FIG. 8B.

The de-identification system 2800 can further include a processing system 2804 that includes at least one processor, and a memory 2806. The memory 2806 can store operational instructions that, when executed by the processing system, cause the de-identification system to perform at least one patient identifier detection function on the received medical scan and/or the medical report to identify a set of patient identifiers in the medical scan and/or the medical report. The operational instructions, when executed by the processing system, can further cause the de-identification system to perform an anonymization function on the medical scan and/or the medical report to generate a de-identified medical scan and/or a de-identified medical report that do not include the set of patient identifiers found in performing the at least one patient identifier detection function. Generating the de-identified medical scan can include generating a de-identified header and generating de-identified image data, where the de-identified medical scan includes both the de-identified header and the de-identified image data. The memory 2806 can be isolated from Internet connectivity, and can be designated for PHI.

The de-identification system 2800 can further include at least one transmitter 2808, operable to transmit the de-identified medical scan and de-identified medical report. The de-identified medical scan and de-identified medical report can be transmitted back to the same entity from which they were received, respectively, and/or can be transmitted to a separate entity. For example, the at least one transmitter can transmit the de-identified medical scan to the de-identified image storage system 2610 of FIGS. 8A-8F and/or can transmit the de-identified medical scan to central server system 2640 via network 2630 of FIGS. 8A-8F. In such embodiments, the transmitter 2808 can be utilized to implement the interface 2655 of FIG. 8B. The receiver 2802, processing system 2804, memory 2806, and/or transmitter 2808 can be connected via bus 2810.

Some or all of the at least one patient identifier detection function and/or at least one anonymization function as discussed herein can be trained and/or implemented by one or subsystems 101 in the same fashion as other medical scan analysis functions discussed herein, can be stored in medical scan analysis function database 346 of FIG. 3, and/or can otherwise be characterized by some or all fields of a medical scan analysis function entry 356 of FIG. 5.

The de-identification system 2800 can perform separate patient identifier detection functions on the header of a medical report and/or medical scan, on the text data of the medical report, and/or on the image data of the medical scan, such as text extracted from the image data of the medical scan. Performance of each of these functions generates an output of its own set of identified patient identifiers. Combining these sets of patient identifiers yields a blacklist term set. A second pass of the header of a medical report and/or medical scan, on the text data of the medical report, and/or on the image data of the medical scan that utilizes this blacklist term set can catch any terms that were missed by the respective patient identifier detection function, and thus, the outputs of these multiple identification processes can support each other. For example, some of the data in the headers will be in a structured form and can thus be easier to reliably identify. This can be exploited and used to further anonymize these identifiers when they appear in free text header fields, report data, and/or in the image data of the medical scan. Meanwhile, unstructured text in free text header fields, report data, and/or image data of the medical scan likely includes pertinent clinical information to be preserved in the anonymization process, for example, so it can be leveraged by at least one subsystems 101 and/or so it can be leveraged in training at least one medical scan analysis function.

At least one first patient identifier detection function can include extracting the data in a subset of fields of a DICOM header, or another header or other metadata of the medical scan and/or medical report with a known type that corresponds to patient identifying data. For example, this patient identifying subset of fields can include a name field, a patient ID number field or other unique patient identifier field, a date field, a time field, an age field, an accession number field, SOP instance UID, and/or other fields that could be utilized to identify the patient and/or contain private information. A non-identifying subset of fields of the header can include hospital identifiers, machine model identifiers, and/or some or all fields of medical scan entry 352 that do not correspond to patient identifying data. The patient identifying subset of fields and the non-identifying subset of fields can be mutually exclusive and collectively exhaustive with respect to the header. The at least one patient identifier function can include generating a first set of patient identifiers by ignoring the non-identifying subset of fields and extracting the entries of the patient identifying subset of fields only. This first set of patient identifiers can be anonymized to generate a de-identified header as discussed herein.

In some embodiments, at least one second patient identifier detection function can be performed on the report data of the medical report. The at least one second patient identifier detection function can include identifying patient identifying text in the report data by performing a natural language analysis function, for example, trained by the medical scan natural language analysis system 114. For example, the at least one second patient identifier detection function can leverage the known structure of the medical report and/or context of the medical report. A second set of patient identifiers corresponding to the patient identifying text can be determined, and the second set of patient identifiers can be anonymized to generate a de-identified medical report. In some embodiments, a de-identified medical report includes clinical information, for example, because the portion of the original medical report that includes the clinical information was deemed to be free of patient identifying text and/or because the portion of the original medical report that includes the clinical information was determined to include pertinent information to be preserved.

In some embodiments, the medical report includes image data corresponding to freehand or typed text. For example the medical report can correspond to a digitized scan of original freehand text written by a radiologist or other medical professional. In such embodiments, the patient identifier detection function can first extract the text from the freehand text in the image data to generate text data before the at least one second patient identifier detection function is performed on the text of the medical report to generate the second set of patient identifiers.

In some embodiments, the at least one second patient identifier detection function can similarly be utilized to identify patient identifying text in free text fields and/or unstructured text fields of a DICOM header and/or other metadata of the medical scan and/or medical report data by performing a natural language analysis function, for example, trained by the medical scan natural language analysis system 114. A third set of patient identifiers corresponding to this patient identifying text of the free text and/or unstructured header fields can be determined, and the third set of patient identifiers can be anonymized to generate de-identified free text header field and/or unstructured header fields. In some embodiments, a de-identified free text header field and/or unstructured header field includes clinical information, for example, because the portion of the original corresponding header field that includes the clinical information was deemed to be free of patient identifying text and/or because the portion of the original corresponding header field that includes the clinical information was determined to include pertinent information to be preserved.

Patient identifiers can also be included in the image data of the medical scan itself. For example, freehand text corresponding to a patient name written on a hard copy of the medical scan before digitizing can be included in the image data, as discussed in conjunction with FIG. 10B. Other patient identifiers, such as information included on a patient wristband or other identifying information located on or within the vicinity of the patient may have been captured when the medical scan was taken, and can thus be included in the image. At least one third patient identifier detection function can include extracting text from the image data and/or detecting non-text identifiers in the image data by performing a medical scan image analysis function, for example, trained by the medical scan image analysis system 112. For example, detected text that corresponds to an image location known to include patient identifiers, detected text that corresponds to a format of a patient identifier, and/or or detected text or other image data determined to correspond to a patient identifier can be identified. The at least one third patient identifier detection function can further include identifying patient identifying text in the text extracted from the image data by performing the at least one second patient identifier detection function and/or by performing a natural language analysis function. A fourth set of patient identifiers corresponding to patient identifying text or other patient identifiers detected in the image data of the medical scan can be determined, and the fourth set of patient identifiers can be anonymized in the image data to generate de-identified image data of the medical scan as described herein. In particular, the fourth set of patient identifiers can be detected in a set of regions of image data of the medical scan, and the set of regions of the image data can be anonymized.

In some embodiments, only a subset of the patient identifier detection functions described herein are performed to generate respective sets of patient identifiers for anonymization. In some embodiments, additional patient identifier detection functions can be performed on the medical scan and/or medical report to determine additional respective sets of patient identifiers for anonymization. The sets of patient identifiers outputted by performing each patient identifier detection function can have a null or non-null intersection. The sets of patient identifiers outputted by performing each patient identifier function can have null or non-null set differences.

Cases where the sets of patient identifiers have non-null set differences can indicate that a patient identifier detected by one function may have been missed by another function. The combined set of patient identifiers, for example, generated as the union of the sets of sets of patient identifiers outputted by performing each patient identifier function, can be used to build a blacklist term set, for example, stored in memory 2806. The blacklist term set can designate the final set of terms to be anonymized. A second pass of header data, medical scans, medical reports, and/or any free text extracted from the header data, the medical scan, and/or the medical report can be performed by utilizing the blacklist term set to flag terms for anonymization that were not caught in performing the respective at least one patient identifier detection function. For example, performing the second pass can include identifying at least one patient identifier of the blacklist term set in the header, medical report, and/or image data of the medical scan. This can include by searching corresponding extracted text of the header, medical report, and/or image data for terms included in blacklist term set and/or by determining if each term in the extracted text is included in the blacklist term set.

In some embodiments, at least one patient identifier is not detected until the second pass is performed. Consider an example where a free text field of a DICOM header included a patient name that was not detected in performing a respective patient identifier detection function on the free text field of the DICOM header. However, the patient name was successfully identified in the text of the medical report in performing a patient identifier detection function on the medical report. This patient name is added to the blacklist term list, and is detected in a second pass of the free text field of the DICOM header. In response to detection in the second pass, the patient name of the free text field of the DICOM header can be anonymized accordingly to generate a de-identified free text field. Consider a further example where the patient name is included in the image data of the medical scan, but was not detected in performing a respective patient identifier detection function on the free text field of the DICOM header. In the second pass, this patient name can be detected in at least one region of image data of the medical scan by searching the image data for the blacklist term set.

In some embodiments, performing some or all of the patient identifier detection functions includes identifying a set of non-identifying terms, such as the non-identifying subset of fields of the header. In particular, the non-identifying terms can include terms identified as clinical information and/or other terms determined to be preserved. The combined set of non-identifying terms, for example, generated as the union of the sets of sets of non-identifying outputted by performing each patient identifier function, can be used to build a whitelist term set, for example, stored in memory 2806. Performing the second pass can further include identifying at least one non-identifying term of the whitelist term set in the header, medical report, and/or image data of the medical scan, and determining not to anonymize, or to otherwise ignore, the non-identifying term.

In various embodiments, some or all terms of the whitelist term set can be removed from the blacklist term set. In particular, at least one term previously identified as a patient identifier in performing one or more patient identifier detection functions is determined to be ignored and not anonymized in response to determining the term is included in the whitelist term set. This can help ensure that clinically important information is not anonymized, and is thus preserved in the de-identified medical scan and de-identified medical report.

In some embodiments, the second pass can be performed after each of the patient identifier detection functions are performed. For example, performing the anonymization function can include performing this second pass by utilizing the blacklist term set to determine the final set of terms to be anonymized. New portions of text in header fields, not previously detected in generating the first set of patient identifiers or the third set of patient identifiers, can be flagged for anonymization by determining these new portions of text correspond to terms of the blacklist term set. New portions of text the medical report, not previously detected in generating in the second set of patient identifiers, can be flagged for anonymization by determining these new portions of text correspond to terms of the blacklist term set. New regions of the image data of the medical scan, not previously detected in generating the fourth set of patient identifiers, can be flagged for anonymization by determining these new portions of text correspond to terms of the blacklist term set.

In some embodiments, the blacklist term set is built as each patient identifier detection function is performed, and performance of subsequent patient identifier detection functions includes utilizing the current blacklist term set. For example, performing the second patient identifier detection function can include identifying a first subset of the blacklist term set in the medical report by searching the text of the medical report for the blacklist term set and/or by determining if each term in the text of the medical report is included in the blacklist term set. Performing the second patient identifier detection function can further include identifying at least one term in the medical report that is included in the whitelist term set, and determining to ignore the term in response. The first subset can be anonymized to generate the de-identified medical report as discussed herein. New patient identifiers not already found can be appended to the blacklist term set, and the updated blacklist term set can be applied to perform a second search of the header and/or image data of the medical scan, and at least one of the new patient identifiers can be identified in the header in the second search of the header and/or in the image data in a second search of the image data. These newly identified patient identifiers in the header and/or image data are anonymized in generating the de-identified medical scan.

As another example, a second subset of the blacklist term set can be detected in a set of regions of image data of the medical scan by performing the medical scan image analysis function on image data of the medical scan, where the image analysis function includes searching the image data for the set of patient identifiers. For example, the medical scan image analysis function can include searching the image data for text, and the second subset can include detected text that matches one or more terms of the blacklist term set. In some embodiments, detected text that matches one or more terms of the whitelist term set can be ignored. The second subset can be anonymized to generate de-identified image data as discussed herein. New patient identifiers that are detected can be appended to the blacklist term set, and the updated blacklist term set can be applied to perform a second search of the header and/or metadata of the medical scan, and/or can be applied to perform a second search of the medical report. At least one of the new patient identifiers can be identified in the header as a result of performing the second search of the header and/or at least one of the new patient identifiers can be identified medical report as a result of performing the second search of the medical report. These newly identified patient identifiers can be anonymized in the header along with the originally identified blacklist term set in generating the de-identified header, and/or can be anonymized in the medical report along with the originally identified first subset in generating the de-identified medical report.

In some embodiments, the memory 2806 further stores a global blacklist, for example, that includes a vast set of known patient identifying terms. In some embodiments, the global blacklist is also utilized by at least one patient identifier detection function and/or in performing the second pass to determine patient identifying terms for anonymization. In some embodiments, the blacklist term set generated for a particular medical scan and corresponding medical report can be appended to the global blacklist for use in performing the second pass and/or in detecting patient identifiers in subsequently received medical scans and/or medical reports.

Alternatively or in addition, the memory 2806 can further store a global whitelist, for example, that includes a vast set of terms that can be ignored. In particular, the global whitelist can include clinical terms and/or other terms that are deemed beneficial to preserve that do not correspond to patient identifying information. In some embodiments, the global whitelist is utilized by at least one patient identifier detection function and/or in performing the second pass to determine terms to ignore in the header, image data, and/or medical report. In some embodiments, the whitelist term set generated for a particular medical scan and corresponding medical report can be appended to the global whitelist for use in performing the second pass and/or in ignoring terms in subsequently received medical scans and/or medical reports.

Alternatively or in addition, the memory 2806 can further store a global graylist, for example, that includes ambiguous terms that could be patient identifying terms in some contexts, but non-identifying terms in other contexts. For example, "Parkinson" could correspond to patient identifying data if part of a patient name such as "John Parkinson", but could correspond to non-patient identifying data meant to be ignored and preserved in the de-identified medical report and/or de-identified medical scan if part of a diagnosis term such as "Parkinson's disease." In some embodiments, the global graylist is also utilized in performing the second pass and/or in performing at least one patient identifier detection function to determine that a term is included in the graylist, and to further determine whether the term should be added to the blacklist term set for anonymization or whitelist term set to be ignored by leveraging context of accompanying text, by leveraging known data types of a header field from which the term was extracted, by leveraging known structure of the term, by leveraging known data types of a location of the image data from which the term was extracted, and/or by leveraging other contextual information. In some embodiments, the graylist term set can be updated based on blacklist and/or whitelist term sets for a particular medical scan and corresponding medical report.

In some embodiments, the at least one anonymization function includes a fiducial replacement function. For example, some or all of the blacklist term set can be replaced with a corresponding, global fiducial in the header, report data, and/or image data. In some embodiments, the global fiducial can be selected from a set of global fiducials based on a type of the corresponding patient identifier. Each patient identifier detected in the header and/or medical report can be replaced with a corresponding one of the set of global text fiducials. Each patient identifiers detected in the image data can be replaced with a corresponding one of the set of global image fiducials. For example, one or more global image fiducials can overlay pixels of regions of the image data that include the identifying patient data, to obfuscate the identifying patient data in the de-identified image data.

The global text fiducials and/or global image fiducials can be recognizable by inference functions and/or training functions, for example, where the global text fiducials and global image fiducials are ignored when processed in a training step to train an inference function and/or are ignored in an inference step when processed by an inference function. Furthermore, the global text fiducials and/or global image fiducials can be recognizable by a human viewing the header, medical report, and/or image data. For example, a radiologist or other medical professional, upon viewing a header, medical report, and/or image data, can clearly identify the location of a patient identifier that was replaced by the fiducial and/or can identify the type of patient identifier that was replaced by the fiducial.

As an example, the name "John Smith" can be replaced in a header and/or medical report with the text "% PATIENT NAME %", where the text "% PATIENT NAME %" is a global fiducial for name types of the header and/or the text of medical reports. The training step and/or inference step of medical scan natural language analysis functions can recognize and ignore text that matches "% PATIENT NAME %" automatically.

Figure 10B:
FIG. 10B is an illustration of an example of anonymizing patient identifiers in image data of a medical scan in accordance with various embodiments.

FIG. 10B illustrates an example of anonymizing patient identifiers in image data of a medical scan. In this example, the name "John Smith" and the date "May 4, 2010" is detected as freehand text in the original image data of a medical scan. The regions of the image data that include the patient identifiers can each be replaced by global fiducial in the shape of a rectangular bar, or any other shape. As shown in FIG. 10B, a first region corresponding to the location of "John Smith" in the original image data is replaced by fiducial 2820 in the de-identified image data, and a second region corresponding to the location of "May 4, 2010" in the original image data is replaced by fiducial 2822 in the de-identified image data. The size, shape, and/or location of each global visual fiducial can be automatically determined based on the size, shape, and/or location of the region that includes the patient identifier to minimize the amount of the image data that is obfuscated, while still ensuring the entirety of the text is covered. While not depicted in FIG. 10B, the fiducial can be of a particular color, for example, where pixels of the particular color are automatically recognized by the training step and/or inference step of medical scan image analysis functions to indicate that the corresponding region be ignored, and/or where the particular color is not included in the original medical scan and/or is known to not be included in any medical scans. The fiducial can include text recognizable to human inspection such as "% PATIENT NAME" and "% DATE" as depicted in FIG. 10B, and/or can include a QR code, logo, or other unique symbol recognizable to human inspection and/or automatically recognizable by the training step and/or inference step of medical scan image analysis functions to indicate that the corresponding region be ignored.

In some embodiments, other anonymization functions can be performed on different ones of the patient identifying subset of fields to generate the de-identified header, de-identified report data, and/or de-identified image data. For example, based on the type of identifying data of each field of the header, different types of header anonymization functions and/or text anonymization functions can be selected and utilized on the header fields, text of the report, and/or text extracted from the image data. A set of anonymization functions can include a shift function, for example, utilized to offset a date, time or other temporal data by a determined amount to preserve absolute time difference and/or to preserve relative order over multiple medical scans and/or medical reports of a single patient. FIG. 10B depicts an example where the shift function is performed on the date detected in the image data to generate fiducial 2822, where the determined amount is 10 years and 1 month. The determined amount can be determined by the de-identification system randomly and/or pseudo-randomly for each patient and/or for each medical scan and corresponding medical report, ensuring the original date cannot be recovered by utilizing a known offset. In various embodiments, other medical scans and/or medical reports are fetched for the same patient by utilizing a patient ID number or other unique patient identifier of the header. These medial scans and reports can be anonymized as well, where the dates and/or times detected in these medical scans and/or medical reports offset by the same determined amount, randomized or pseudo-randomized for particular patient ID number, for example, based on performing a hash function on the patient ID number.

The set of anonymization functions can include at least one hash function, for example utilized to hash a unique patient ID such as a patient ID number, accession number, and/or SOP instance UID of the header and/or text. In some embodiments, the hashed SOP instance UID, accession number, and/or patient ID number are prepended with a unique identifier, stored in a database of the memory 2806 and/or shared with the entities to which the de-identified medical scans and/or medical reports are transmitted, so that de-identified medical scans and their corresponding de-identified medical reports can be linked and retrieved retroactively. Similarly, longitudinal data can be preserved as multiple medical scans and/or medical reports of the same patient will be assigned the same hashed patient ID.

The set of anonymization functions can further include at least one manipulator function for some types of patient identifiers. Some values of header fields and/or report text that would normally not be considered private information can be considered identifying patient data if they correspond to an outlier value or other rare value that could then be utilized to identify the corresponding patient from a very small subset of possible options. For example, a patient age over 89 could be utilized to determine the identity of the patient, for example, if there are very few patients over the age of 89. To prevent such cases, in response to determining that a patient identifier corresponds to an outlier value and/or in response to determining that a patient identifier compares unfavorably to a normal-range threshold value, the patient identifier can be capped at the normal-range threshold value or can otherwise be manipulated. For example, a normal-range threshold value corresponding to age can be set at 89, and generating a de-identified patient age can include capping patient ages that are higher than 89 at 89 and/or can include keeping the same value for patient ages that are less than or equal to 89.

In some embodiments, the de-identified header data is utilized to replace the corresponding first subset of patient identifiers detected in the medical report with text of the de-identified header fields. In other embodiments, a set of text anonymization functions includes a global text fiducial replacement function, shift function, a hash function, and/or manipulator functions that anonymize the corresponding types of patient identifiers in the medical report separately.

In some embodiments where the image data of a medical scan includes an anatomical region corresponding to a patient's head, the image data may include an identifying facial structure and/or facial features that could be utilized to determine the patient's identity. For example, a database of facial images, mapped to a corresponding plurality of people including the patient, could be searched and a facial recognition function could be utilized to identify the patient in the database. Thus, facial structure included in the image data can be considered patient identifying data.

To prevent this problem and maintain patient privacy, the de-identification system can further be implemented to perform facial obfuscation for facial structure detected in medical scans. At least one region of the image data that includes identifying facial structure can be determined by utilizing a medical image analysis function. For example, the medical image analysis function can include a facial detection function that determines the regions of the image data that include identifying facial structure based on searching the image data for pixels with a density value that corresponds to facial skin, facial bone structure, or other density of an anatomical mass type that corresponds to identifying facial structure, and the facial obfuscation function can be performed on the identified pixels. Alternatively or in addition, the facial detection function can determine the region based on identifying at least one shape in the image data that corresponds to a facial structure.

The image obfuscation function can include a facial structure obfuscation function performed on the medical scan to generate de-identified image data that does not include identifying facial structure. For example, the facial structure obfuscation function can mask, scramble, replace with a fiducial, or otherwise obfuscate the pixels of the region identified by the facial detection function. In some embodiments, the facial structure obfuscation function can perform a one-way function on the region that preserves abnormalities of the corresponding portions of the image, such as nose fractures or facial skin legions, while still obfuscating the identifying facial structure such that the patient is not identifiable. For example, the pixels of the identifying facial structure can be altered such that they converge towards a fixed, generic facial structure. In some embodiments, a plurality of facial structure image data of a plurality of patients can be utilized to generate the generic facial structure, for example, corresponding to an average or other combination of the plurality of faces. For example, the pixels of the generic facial structure can be averaged with, superimposed upon, or otherwise combined with the pixels of the region of the image data identified by the facial detection function in generating the de-identified image data.

In some embodiments, a hash function can be performed on an average of the generic facial structure and the identified facial structure of the image data so that the generic facial structure cannot be utilized in conjunction with the resulting data of the de-identified image data to reproduce the original, identifying facial structure. In such embodiments, the hash function can alter the pixel values while still preserving abnormalities. In some embodiments, a plurality of random, generic facial structures can be generated by utilizing the plurality of facial structure image data, for example, where each if the plurality of facial structure image data are assigned a random or pseudo-random weight in an averaging function utilized to create the generic facial structure, where a new, random or pseudo-random set of weights are generated each time the facial structure obfuscation function is utilized to create a new, generic facial structure to be averaged with the identified facial structure in creating the de-identified image data to ensure the original identifying facial structure cannot be extracted from the resulting de-identified image data.

While facial obfuscation is described herein, similar techniques can be applied in a similar fashion to other anatomical regions that are determined to include patient identifiers and/or to other anatomical regions that can be utilized to extract patient identifying information if not anonymized.

In some embodiments, the at least one receiver 2802 is included in at least one transceiver, for example, enabling bidirectional communication between the medical picture archive system 2620 and/or the report database 2625. In such embodiments, the de-identification system 2800 can generate queries to the medical picture archive system 2620 and/or the report database 2625 for particular medical scans and/or medical reports, respectively. In particular, if the medical scan and medical report are stored and/or managed by separate memories and/or separate entities, they may not be received at the same time. However, a linking identifier, such as DICOM identifiers in headers or metadata of the medical scan and/or medical report, such accession number, patient ID number, SOP instance UID, or other linking identifier that maps the medical scan to the medical report can be utilized to fetch a medical report corresponding to a received medical scan and/or to fetch a medical scan corresponding to a received medical report via a query sent utilizing the at least one transceiver. For example, in response to receiving the medical scan from the medical picture archive system 2620, the de-identification system can extract a linking identifier from a DICOM header of the medical scan, and can query the report database 2625 for the corresponding medical report by indicating the linking identifier in the query. Conversely, in response to receiving the medical report from the report database 2625, the de-identification system can extract the linking identifier from a header, metadata, and/or text body of the medical report, and can query the medical picture archive system 2620 for the corresponding medical scan by indicating the linking identifier in the query. In some embodiments, a mapping of de-identified medical scans to original medical scans, and/or a mapping of de-identified medical reports to original medical reports can be stored in memory 2806. In some embodiments, linking identifiers such as patient ID numbers can be utilized to fetch additional medical scans, additional medical reports, or other longitudinal data corresponding to the same patient.

FIG. 11 presents a flowchart illustrating a method for execution by a de-identification system 2800 that stores executional instructions that, when executed by at least one processor, cause the de-identification to perform the steps below.

Step 2902 includes receiving from a first entity, via a receiver, a first medical scan and a medical report corresponding to the medical scan. Step 2904 includes identifying a set of patient identifiers in a subset of fields of a first header of the first medical scan. Step 2906 includes performing a header anonymization function on each of the set of patient identifiers to generate a corresponding set of anonymized fields. Step 2908 includes generating a first de-identified medical scan by replacing the subset of fields of the first header of the first medical scan with the corresponding set of anonymized fields. Step 2910 includes identifying a first subset of patient identifiers of the set of patient identifiers in the medical report by searching text of the medical report for the set of patient identifiers. Step 2912 includes performing a text anonymization function on the first subset of patient identifiers to generate corresponding anonymized placeholder text for each of the first subset of patient identifiers. Step 2914 includes generating a de-identified medical report by replacing each of the first subset of patient identifiers with the corresponding anonymized placeholder text. Step 2916 includes transmitting, via a transmitter, the de-identified first medical scan and the de-identified medical report to a second entity via a network.

In various embodiments, the medical scan is received from a Picture Archive and Communication System (PACS), where the medical report is received from a Radiology Information System (RIS), and where the first de-identified medical scan and the de-identified medical report are transmitted to a central server that is not affiliated with the PACS or the RIS. In various embodiments, first medical scan and the medical report are stored in a first memory for processing. The first memory is decoupled from the network to prevent the set of patient identifiers from being communicated via the network. The first de-identified medical scan and the de-identified medical report are stored in a second memory that is separate from the first memory. The first de-identified medical scan and the de-identified medical report are fetched from the second memory for transmission to the second entity.

In various embodiments, the header anonymization function performed on each of the set of patient identifiers is selected from a plurality of header anonymization functions based on one of a plurality of identifier types of the corresponding one of the subset of fields. In various embodiments, the plurality of identifier types includes a date type. A shift function corresponding to the date type is performed on a first date of the first header to generate the first de-identified medical scan, where the shift function includes offsetting the first date by a determined amount. A second medical scan that includes a second header is received, via the receiver. A unique patient ID of the first header matches a unique patient ID of the second header. The shift function is performed on a second date of the second header by offsetting the second date by the determined amount to generate a second de-identified medical scan. The second de-identified medical scan is transmitted to the second entity via the network.

In various embodiments, the plurality of identifier types includes a unique patient ID type. A hash function corresponding the unique patient ID type is performed on the unique patient ID of the first header to generate the first de-identified medical scan. The hash function is performed on the unique patient ID of the second header to generate the second de-identified medical scan. An anonymized unique patient ID field of the first de-identified medical scan matches an anonymized unique patient ID field of the second de-identified medical scan as a result of the unique patient ID of the first header matching the unique patient ID of the second header.

In various embodiments, the plurality of identifier types includes a linking identifier type that maps the medical scan to the medical report. A hash function corresponding to the linking identifier type is performed on a linking identifier of the first header to generate a hashed linking identifier. A linking identifier field of the first de-identified medical scan includes the hashed linking identifier. Performing the text anonymization function on the first subset of patient identifiers includes determining one of the first subset of patient identifiers corresponds to linking identifier text and performing the hash function on the one of the first subset of patient identifiers to generate the hashed linking identifier, where the de-identified medical report includes the hashed linking identifier.

In various embodiments, a second subset of patient identifiers of the set of patient identifiers is identified in a set of regions of image data of the medical scan by performing an image analysis function on image data of the medical scan. The image analysis function includes searching the image data for the set of patient identifiers. An identifier type is determined for each of the second subset of patient identifiers. One of a plurality of image fiducials is selected for each of the second subset of patient identifiers based on the identifier type. De-identified image data is generated, where a set of regions of the de-identified image data, corresponding to the set of regions of the image data, includes the one of the plurality of image fiducials to obfuscate each of the second subset of patient identifiers. Generating the first de-identified medical scan further includes replacing the image data of the medical scan with the de-identified image data.

In various embodiments, a new patient identifier is identified in the medical report by performing a natural language analysis function on the medical report, where new patient identifier is not included in the set of patient identifiers. The set of patient identifiers is updated to include the new patient identifier prior to searching the image data of the medical scan for the set of patient identifiers, and the second subset of patient identifiers includes the new patient identifier.

In various embodiments, the memory further stores a global identifier blacklist. The natural language analysis function includes searching the medical report for a plurality of terms included in the global identifier blacklist to identify the new patient identifier. In various embodiments, the de-identification system determines that the global identifier blacklist does not include one of the set of patient identifiers, and the global identifier blacklist is updated to include the one of the set of patient identifiers.

In various embodiments, performing the image analysis function further includes identifying a new patient identifier in the image data, where new patient identifier is not included in the set of patient identifiers. Identifying text is extracted from a region of the image data corresponding to the new patient identifier. The new patient identifier is identified in the medical report by searching text of the medical report for the identifying text. The text anonymization function is performed on new patient identifier to generate anonymized placeholder text for the new patient identifier. Generating the de-identified medical report further includes replacing the identifying text with the anonymized placeholder text for the new patient identifier.

In various embodiments, generating the de-identified image data further includes detecting an identifying facial structure in the image data of the medical scan. Generating the de-identified image data includes performing a facial structure obfuscation function on the image data, and where the de-identified image data does not include the identifying facial structure.

FIGS. 12A-12E illustrate embodiments of a medical scan header standardization system 3002. The medical scan header standardization system 3002 can be utilized to generate and/or correct headers for medical scans and/or medical reports based on a standardized header rules, and/or based on properties determined in the medical scans and/or medical reports.

As shown in FIGS. 12A-12E, the medical scan header standardization system 3002 can communicate bi-directionally, via network 150, with the medical scan database 342, a report database 3044, and/or other databases of the database storage system 140. While not shown in FIGS. 12A-12G, the medical scan header standardization system 3002 can further communicate bi-directionally, via network 150, with one or more client devices 120, and/or one or more subsystems 101 of FIG. 1. In some embodiments, the medical scan header standardization system 3002 is an additional subsystem 101 of the medical scan processing system 100, implemented by utilizing the subsystem memory device 245, subsystem processing device 235, and/or subsystem network interface 265 of FIG. 2A. As described in further detail in FIGS. 14A-14B. The medical scan database 342 can correspond to a PACS server and/or medical picture archive system 2620. The report database 3044 can correspond to a RIS and/or report database 2625.

In some embodiments, the medical scan header standardization system 3002 is implemented by utilizing, or otherwise communicates with, the central server 2640. For example, some or all of the databases of the database storage system 140 are populated with de-identified data generated by the medical picture archive integration system 2600. In some embodiments, the medical scan header standardization system 3002 can receive de-identified medical scans, annotation data, and/or reports directly from the medical picture archive integration system 2600. For example, the medical scan header standardization system 3002 can request de-identified medical scans, annotation data, and/or reports that match requested criteria. In some embodiments, some or all of the medical scan header standardization system 3002 is implemented by utilizing other subsystems 101 and/or is operable to perform functions or other operations described in conjunction with one or more other subsystems 101.

Across different radiologists and/or across different hospital systems, medical scan headers such as DICOM headers may not follow a standardized set of requirements. Lack of standardization, for example in a PACS system, can cause problems for users and/or subsystems 101 that utilize medical scans and/or medical reports stored in a PACS system and/or other medical scan database 342. The medical scan header standardization system 3002 presents improvements to existing systems to alleviate many of these problems.

Lack of standardization for fields that should have a fixed set of options, such as header fields indicating modality and/or anatomical region of the scan, can cause inconsistency and lack of clarity for users, interfaces, and/or subsystems 101 that need to know what type of medical scan they have received for use. One example of lack of standardization includes differing entries to convey the same information. Different radiologists and/or hospitals may populate header fields differently, where the same information is conveyed in different formats. For example, "Chest CT" and "CT of Chest" may be entries for different chest CT scans, but both entries refer to the same anatomical region and modality. Another example of lack of standardization includes headers with entries that do not follow a specified format or specified rules. Another example of lack of standardization can include headers with fields in different orders.

PACS user interface systems and/or other interactive interfaces of subsystems 101 that display medical scans to users can automatically determine the layout of interface window arrangements and/or other interface features in displaying the medical scan based on the modality, anatomical region, or other properties of the medical scan type indicated in the header. Medical scans with incorrect and/or unclear header fields for such information can cause these interfaces to display window arrangements incorrectly and/or to display interface features incorrectly. Automatically standardizing such fields for some or all medical scans and/or reports in a PACS or other medical scan database 342 improves existing systems by clarifying what type of study a radiologist is looking at when viewing image data of a medical scan via a user interface of one or more subsystems 101 and/or via a PACS interface. This can improve performance of the interface itself, for example, by ensuring that arrangement of windows is set correctly based on the scan type identified in the header, and by preventing automatic hanging protocols.

Lack of standardization for fields that should have a fixed set of options can also lead to problems in generating training sets to train medical scan analysis functions. For example, multiple entries that convey the same information can lead to training data with inconsistent labels and/or feature vectors. The training process can be improved and more robust models can be generated when a same, single label conveys the same information. Furthermore, if different models are generated for different types of medical scans, and are trained accordingly for these different types of medical scans, automatically standardizing fields for medical scans and/or medical reports can ensure that sets of training data are grouped appropriately by scan type.

Automatically standardizing headers also improves existing systems by easing the querying of the database for other purposes by allowing users and/or subsystems 101 to structure queries based on the standardized fields to fetch and/or otherwise access sets of medical scans that meet desired criteria identified by standardized entries of one or more standardized header fields.

The medical scan header standardization system 3002 can further be utilized to correct errors in medical scan headers and/or medical report headers. Typos, errors, or missing fields in medical scan headers and/or medical report headers can cause confusion and problems. For example, typos, errors, or missing fields can cause multiple medical scans and/or reports for the same patient to become unlinked, based on slightly differing patient names or patient identifiers. As another example, mistyped dates can cause medical scans and/or reports for the same patient to become out of order or reflect the wrong passage of time between medical scans. As another example, mistyped or missing accession numbers can cause medical scans and medical reports to become unlinked. Even missing or incorrect standardized fields, such as an incorrect modality and/or anatomical region, can cause medical scans to be assigned to inappropriate training sets and/or be inadvertently accessed in response to a query. Utilizing the medical scan header standardization system 3002 to correct errors and/or populate missing fields can further improve existing systems by preventing many of these problems. Automatically detecting and correcting these errors not only ensures such problems are proactively prevented, but also alleviates human responsibility to find and correct these errors.

Figure 12A:
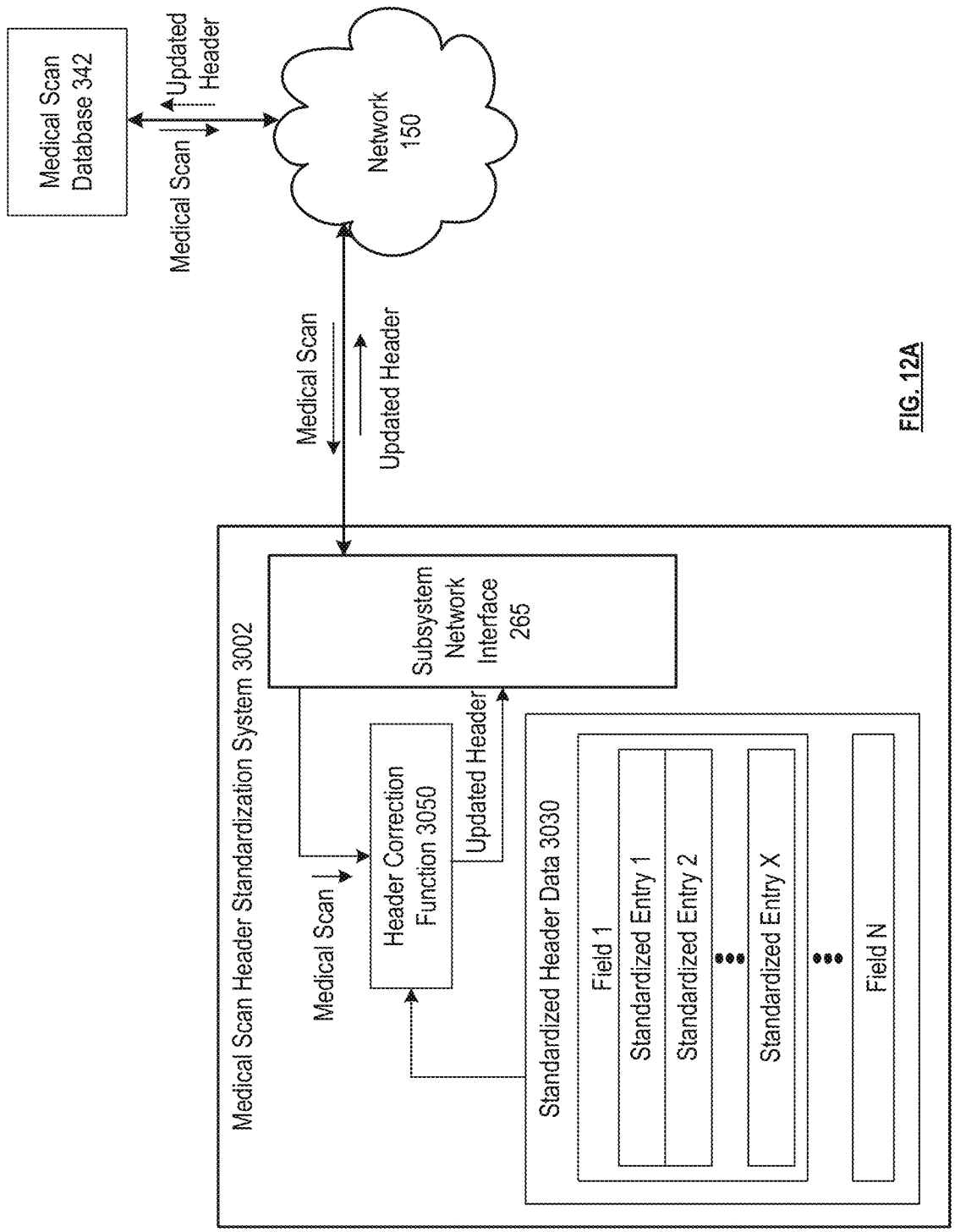

The medical scan header standardization system 3002 can include at least one processor and memory that stores operational instructions to perform the functions of the medical scan header standardization system 3002. The memory can further store header standardization data 3030. As shown in FIG. 12A, the header standardization data 3030 can include a fixed set of standardized entries 1-X for each of a set of standardized fields 1-Z. The number of standardized entries 1-X can be the same or different for some or all of the set of standardized fields 1-Z. The header standardization data 3030 can store a standardized ordering for the standardized set of fields.

In some embodiments, some of the Z standardized fields do not correspond to a fixed set of options. For example, a patient name may not correspond to a discrete, fixed set of options. The header standardization data 3030 can indicate which of the Z standardized fields must adhere to one of a fixed set of entry options, and can indicate other ones of the Z fields that can include an entry that does correspond to a fixed set of entry options. In some embodiments, even fields that do not have a discrete set of options can still have formatting rules or other bounds associated with them. For example, a scan date field can have formatting rules indicating dates must be in "MM/DD/YYYY" format, and that can dates cannot be future dates relative to the current date. Such formatting rules for some or all of the Z fields can also be stored in the header standardization data 3030. The header standardization data 3030 can further indicate if some or all of the Z fields are optional, where a null value may be appropriate, and can indicate that some or all of the Z fields are mandatory, where a null value is not valid.

The set of standardized fields 1-Z can include some or all of: a patient identifier field that indicates a number or other unique patient identifier; one or more other patient information fields that include patient name and/or indicate other information identifying or corresponding to the patient; an accession number field that includes an accession number; a SOP UID field that indicates a SOP UID; one or more temporal fields that indicate a scan date and/or time; one or more medical entity identifiers that indicate a medical professional that performed and/or reviewed the scan and/or a hospital associated with the scan; one or more scan type fields that indicates a modality and/or anatomical regions of the scan; and/or other metadata associated with the medical scan. The set of standardized fields 1-Z can be in accordance a DICOM image format. The set of standardized fields can include fields corresponding to some or all of the scan classifier data 420 and/or any other fields of a medical scan entry 352 as discussed herein.

As shown in FIG. 12A, a medical scan can be received from the medical scan database. A header correction function 3050 can be performed on the medical scan to extract the current header from the medical scan to generate an updated header based on the current header. The updated header can be transmitted back to the medical scan database to replace the original header or otherwise be mapped to the medical scan in the medical scan database. In some embodiments, the medical scan itself is reformatted to include the updated header, and/or is reformatted to replace a subset of fields of the current header with a subset of updated fields generated by performing the header correction function 3050. The reformatted medical scan can be similarly transmitted back to the medical scan database 342 to replace the corresponding original medical scan.

The updated header can be the same as the current header in response to performance of the header correction function 3050 indicating that no correction is necessary. Alternatively, the medical scan header standardization system can forego generation of and transmission of an updated header in response to the header correction function 3050 indicating that no correction is necessary.

In the case that correction occurs, the updated header can include a subset of updated fields and a subset of unaltered fields. In some embodiments, every field of the current header is changed to generate the updated header. In some embodiments, the medical scan header standardization system 3002 determines the current header does not to adhere to one or more rules indicated in the header standardization data 3030 in performing the header correction function 3050. Performing the header correction function 3050 can include firstly evaluating every field of the header to determine whether the corresponding field adheres to the rules of the header standardization data 3030 for that field, and secondly correcting fields determined not to adhere to the header standardization data. In some embodiments, performing the header correction function 3050 includes ignoring some fields, for example, in response to the header standardization data 3030 indicating no standardization rules for these ignored fields. In response to performing the header correction function 3050, the updated header generated by the medical scan header standardization system 3002 can adhere to a standardized header format in accordance with the header standardization data 3030.

In particular, a first subset of fields of the updated header, corresponding to all of the fields indicated in the header standardization data 3030 that must include one of a fixed set of entry options, can each include one of the fixed set of options for the corresponding one of the set of fields, where at least one entry of one of the first subset of fields was altered from a prior entry that did not match any of the corresponding fixed set of entry options to generate the updated header. Alternatively or in addition, a second subset of fields of the updated header, corresponding to all of the fields indicated in the header standardization data 3030 that must adhere to a corresponding formatting rules, can each adhere to the corresponding formatting rules, where at least one entry of one of the second subset of fields was altered from a prior entry that did not adhere to corresponding formatting rules to generate the updated header. Alternatively or in addition, a third subset of fields of the updated header, corresponding to all of the fields indicated in the header standardization data 3030 that are mandatory, can each include a non-null entry that is one of a corresponding fixed set of options and/or otherwise adheres to corresponding formatting rules, where at least one entry of one of the third subset of fields was altered from a prior entry that was null to generate the updated header.

Selecting one of the fixed set of standardized entries to generate a field of the updated header can include comparing the current entry for the field to some or all of the fixed set of standardized entries 1-X for the field, and determining which one of the fixed set of entries compares most favorably to the current entry. For example, an entry comparison function can be performed to determine a comparison value for all of the set of standardized entries, for example, where each comparison value indicates a difference between the current entry and a corresponding one of the set of standardized entries. The one of the set of standardized entries with the most favorable comparison value, for example, corresponding to the smallest difference, can be selected for the updated header.

In some embodiments, the entry comparison function includes a character by character comparison of text in the current entry and each of the set of standardized entries. For example, this can be utilized to catch and correct typos, where the current, unstandardized entry is only a couple of characters off from one of the fixed set of standardized entries. In some embodiments, the entry comparison function includes a word by word comparison function, and/or can include a search for key words, identified in the entry, in each of the set of standardized entries. This can be utilized to catch and correct unstandardized versions of the same information. For example, "x-ray of Chest" can determined to most closely to one of the set of standardized entries that reads "Chest x-ray" based on this search for key words.

Figure 12B:
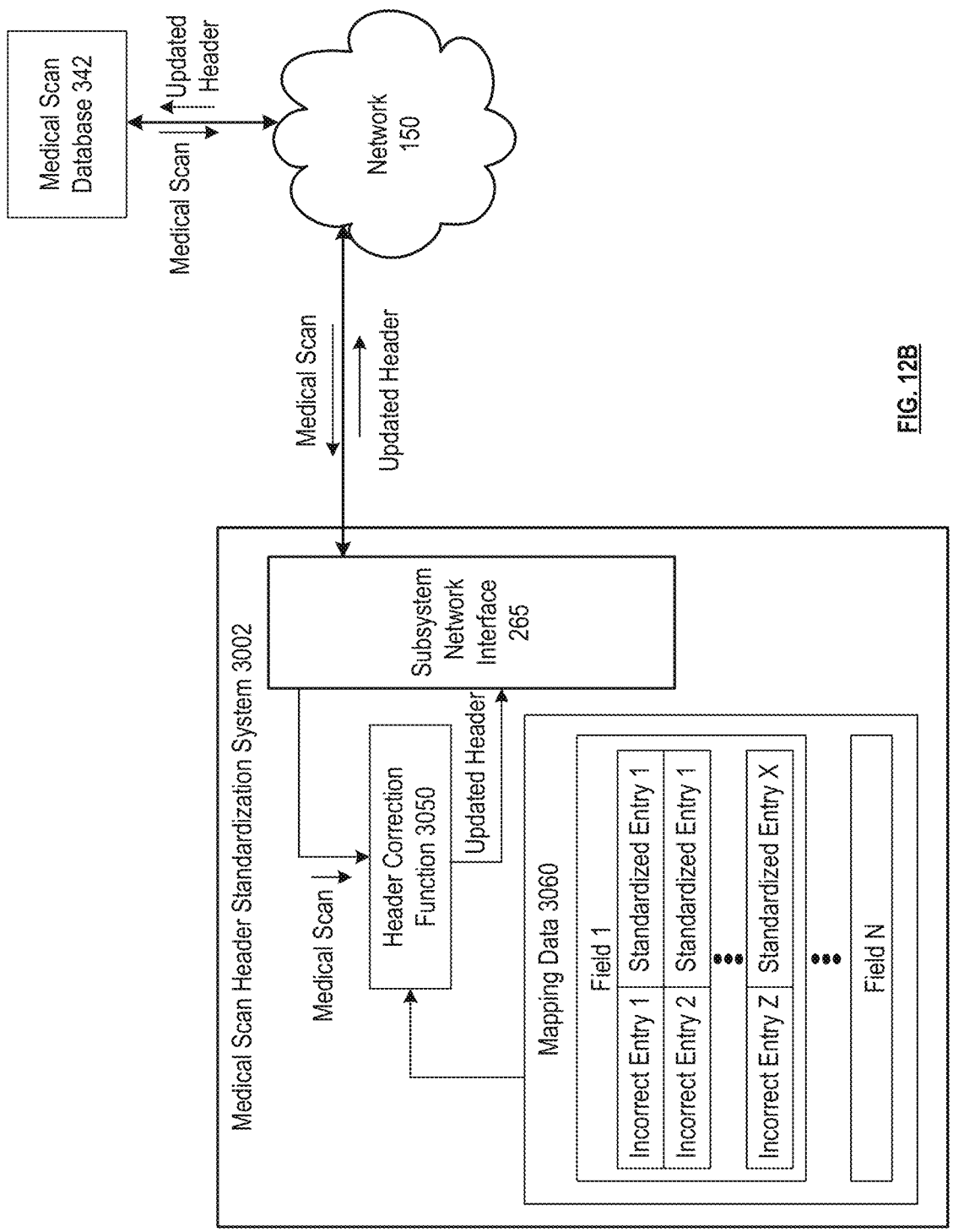

FIG. 12B illustrates an embodiment where the header correction function 3050 utilizes mapping data 3060 to determine one of a fixed set of standardized entries for some or all of the fields. The mapping data 3060 can be indicated in the header standardization data 3030, and can indicate one or more known, unstandardized fields that map to some or all of the standardized set of fields. For example, if one of the set of standardized entries for a field is "Computerized Tomography: Chest", the mapping data 3060 can indicate "CT of Chest", "Chest CT", and "Computerized Tomography of Chest" are all unstandardized entries that map to "Computerized Tomography: Chest". Performing the header correction function 3050 can include determining that an entry of the current header is included in the mapping data 3060 as a known, unstandardized entry for the corresponding field, and can include selecting the corresponding standardized entry mapped to this known, unstandardized entry to generate the updated header.

Performing the header correction function 3050 can include determining that an entry of the current header is not included in the mapping data 3060 for the corresponding field as a standardized entry or as a known, unstandardized entry. In response, performing the header correction function 3050 can include comparing the current entry for the field to some or all of the fixed set of standardized entries 1-X for the field, and also comparing the currently entry to some or all of the known, unstandardized entries mapped to each of these standardized entries 1-X for the field. The entry comparison function can be performed to determine a comparison value for all of the set of standardized entries and for all of the known unstandardized entries. The unstandardized entry with the most favorable comparison value can be determined, and the standardized entry mapped to this unstandardized entry with the most favorable comparison value can be selected for the updated header. In some embodiments, the current entry is added to the mapping data to map to the selected standardized entry.

Selecting the entry can further include determining the corresponding comparison value compares favorably to a comparison threshold, indicating that this most favorable comparison value indicates a small enough difference to be considered valid. In some embodiments, when the most favorably comparison value compares unfavorably to the comparison threshold, the current entry is left unaltered, as the currently entry is determined to be inconclusive. Alternatively, the current entry can be set to null and/or can be set to a standardized "inconclusive" entry value to maintain standardization.

In some embodiments, the inconclusive current entry is sent to a client device for display via a display device. The current entry can be sent and displayed in conjunction with the rest of the header and/or in conjunction with the medical scan. A user of the client device can select one of the fixed set of entries via user input to an interactive interface in response to a prompt to select one of the fixed set of entries, and the selected one of the fixed set of options is transmitted by the client device to the medical scan header standardization system 3002. This selected entry can be included in the updated header. The mapping data 3060 can be updated to include a new entry indicating a mapping of the inconclusive current entry to the selected entry.

The user may have utilized other header fields and/or properties of the medical scan in making the determination to select the selected entry. In such cases, the validity of the selected entry may have been contingent on entries of one or more of these other header fields and/or may have been contingent on one or more of these properties. The user can also indicate mandatory entries of one or more other header and/or one or more mandatory properties of the medical scan via user input to the interactive interface displayed on the display device in responses to a prompt to enter this mandatory information. The mandatory entries of one or more other header and/or one or more mandatory properties of the medical scan entered by the user can be transmitted by the client device to the medical scan header standardization system 3002 with the selected entry. The header standardization data 3030 can include the mandatory entries and/or the mandatory properties as dependency requirements.

If a future medical scan includes the inconclusive entry, performing the header correction function 3050 can include determining whether the dependency requirements are met by determining whether the mandatory entries compare favorably to the corresponding fields of the current header and/or by determining whether the mandatory property is present in the medical scan. The dependency requirements can be determined to be met when the mandatory entries compare favorably to the corresponding fields and when the mandatory property is determined to be present in the medical scan. In response to determining the dependency requirements are not met, the inconclusive entry will not be updated to reflect the corresponding selected entry. Instead, the inconclusive entry in the future medical scan can be left unaltered, can be set to the standardized inconclusive entry value, and/or can be sent to the same or a different client device of the same or different user, where the user similarly determines the appropriate standardized entry via user input and/or determines additional dependency requirements based on this future medical scan, where the appropriate standardized entry and/or the additional dependency requirements are transmitted back to the medical scan header standardization system 3002 to generate the updated header and to update the header standardization data 3030 accordingly.

Similar dependency requirements generated by a user and/or generated automatically can be included in the header standardization data 3030 for other fields, indicating allowable sets of at least two standardized entries in at least two corresponding of fields that are allowed; indicating disallowed sets of at least two standardized entries in at least two corresponding of fields that are disallowed; indicating a standardized entry or subset of standardized entries that must be present in a corresponding field, given at least one standardized entry is present in at least one other corresponding field and/or given at least one property is present in the medical scan; indicating whether such dependencies are one-way or multi-way dependencies; and/or indicating other dependency requirements. Such dependency requirements can be utilized in the performing the header correction function 3050 detecting problems in headers and/or to correct one or more entries of one or more fields in headers in generating updated headers, where the updated headers adhere to the dependency requirements.

If performance of the header correction function 3050 leads to a determination that at least one dependency requirement is irresolvable and/or that an appropriate correction to the at least one dependency requirement is inconclusive, the header and/or the medical scan can be transmitted to a client device for display via a display device, and a user can enter one or more fields for the updated header via a user interface displayed on the display device in response to a prompt to enter the updated fields. These fields can be can be transmitted by the client device back to the medical scan header standardization system 3002 and can be utilized to generate the updated header and/or to update the header standardization data 3030. In some embodiments, the user can enter one or more additional dependency requirements and/or corrected dependency requirements via the user interface displayed on the display device in response to a prompt to enter the additional dependency requirements and/or corrected dependency requirements, in conjunction with the user's review of the header with the irresolvable dependency requirement. The one or more additional dependency requirements and/or corrected dependency requirements can be transmitted by the client device back to the medical scan header standardization system 3002 and can be utilized to update the header standardization data 3030 accordingly.

Generating the updated header can include altering one or more fields based on properties of the medical scan itself, such as properties detected in the image data of the medical scan. These fields can be altered even if they contain entries that are one of the standardized set of entries for the field, in response to determining the current standardized entry is incorrect based on the detected properties. These properties can correspond to some or all of the dependency requirements, can be utilized to determine that one or more header entries is incorrect, and/or can otherwise be utilized to determine an updated entry for one or more fields.

In particular, performing the header correction function 3050 can include performing a medical scan analysis function on image data, metadata, or other data of the medical scan. For example, a medical scan image analysis function generated in conjunction with the medical scan image analysis system 112 can performed on the image data of the medical scan and/or where an inference function received from central server 2640 is performed on the image data of the medical scan to generate inference data. This inference data can be utilized to determine the one or more properties and/or can directly indicate one or more standardized entries of one or more headers. For example, a scan type detection function can be performed on image data of the medical scan to determine the modality of the medical scan and/or the anatomical region of the medical scan. The determined modality of the medical scan and/or the anatomical region of the medical scan can be utilized to determine one or more corresponding fields are incorrect and/or can be utilized to correct one or more corresponding fields to reflect the determined modality of the medical scan and/or the anatomical region of the medical scan in accordance with the standardized format. This scan type detection function can utilize features of one or more medical scan analysis function discussed herein, and can be trained on a training set of multiple medical scans labeled with corresponding modality and/or anatomical region by the medical scan image analysis system 112, the central server 2640, and/or another subsystem 101.

As another example, other information included in the image data of the medical scan, such as patient name, a scan date, and/or other information corresponding to one or more fields can be determined based on detecting this information in image data of the medical scan by performing the patient identifier detection function of the de-identification system 2800 discussed in conjunction with FIGS. 10A and 10B and/or by performing another medical scan analysis function, for example, trained to detect and identify text in the image data of medical scans. This information can be utilized to detect errors for one or more entries in corresponding fields of the header and/or can be utilized to generate an updated header that includes updated fields based on the detected information in the image data. In some embodiments, such fields are left unaltered even if they compare unfavorably to the corresponding text extracted from the image data, for example, if the header fields are determined to be more reliable than text extracted from the image data. In some embodiments, these fields are updated based on the text extracted from the image data only when the corresponding field in the current header is null and/or missing.

Figure 12C:
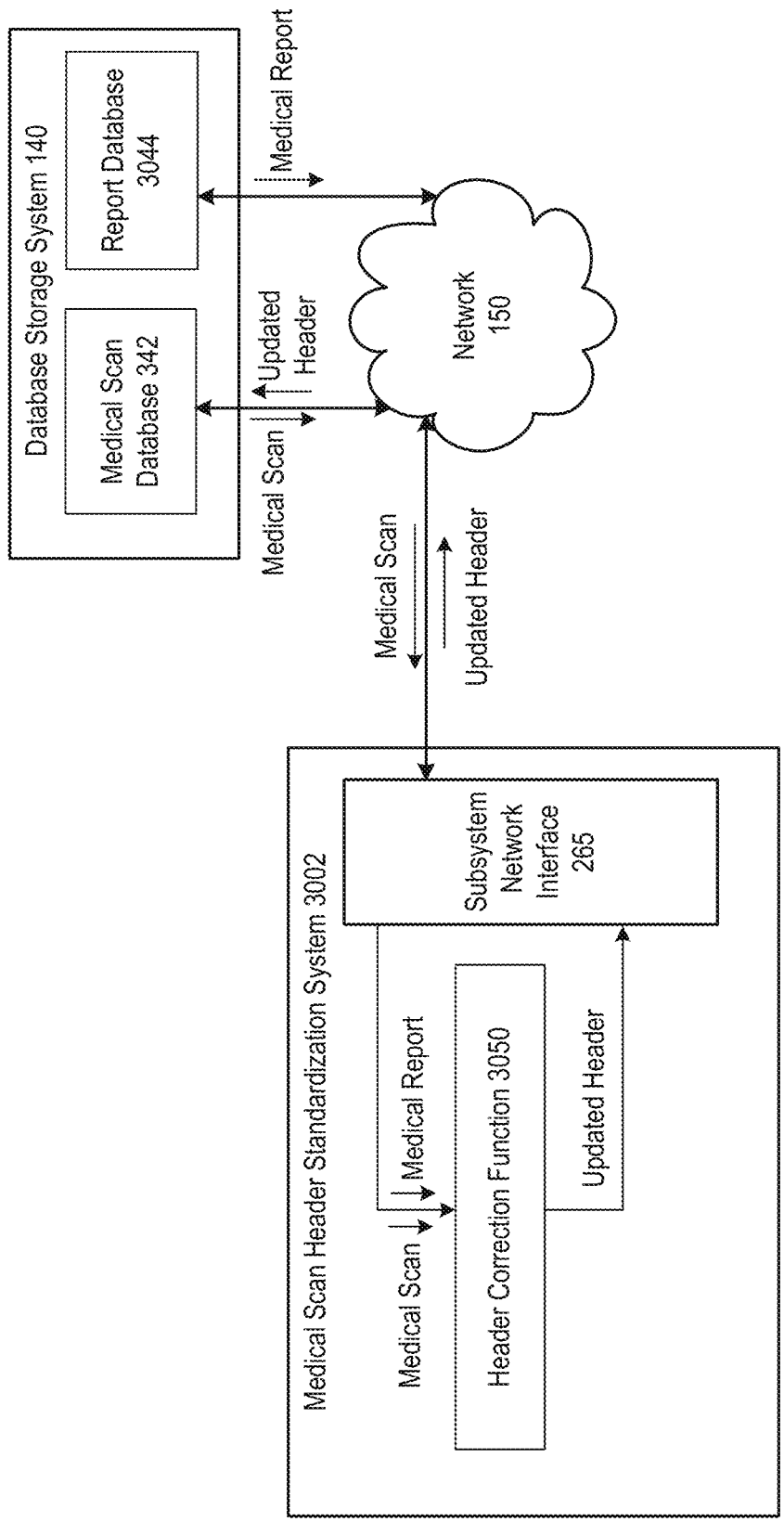

As illustrated in FIG. 12C, the medical scan header standardization system 3002 can further utilize one or more medical reports corresponding to the medical scan to generate the updated header. For example, a patient identifier, scan date, modality, or other data can extracted from the header of the report and/or can be extracted from the text of the report, and can be utilized to detect errors in the header of the medical scan and/or to determine one or more of the fixed set of standardized entries for one or more fields in generating the updated header. The one or more medical reports corresponding to the medical scan can be fetched from the report database based on the accession number field of the header of the medical scan and/or another linking identifier that indicates the one or more medical reports. In some embodiments, a missing and/or incorrect accession number is first corrected, and this corrected accession number is utilized to enable the corresponding one or more medical reports to be fetched from the report database. For example, the accession number correction system of FIGS. 13A and 13B can be utilized to correct the accession number. The corrected accession number can be included in the updated header generated by the medical scan header standardization system.

Figure 12D:
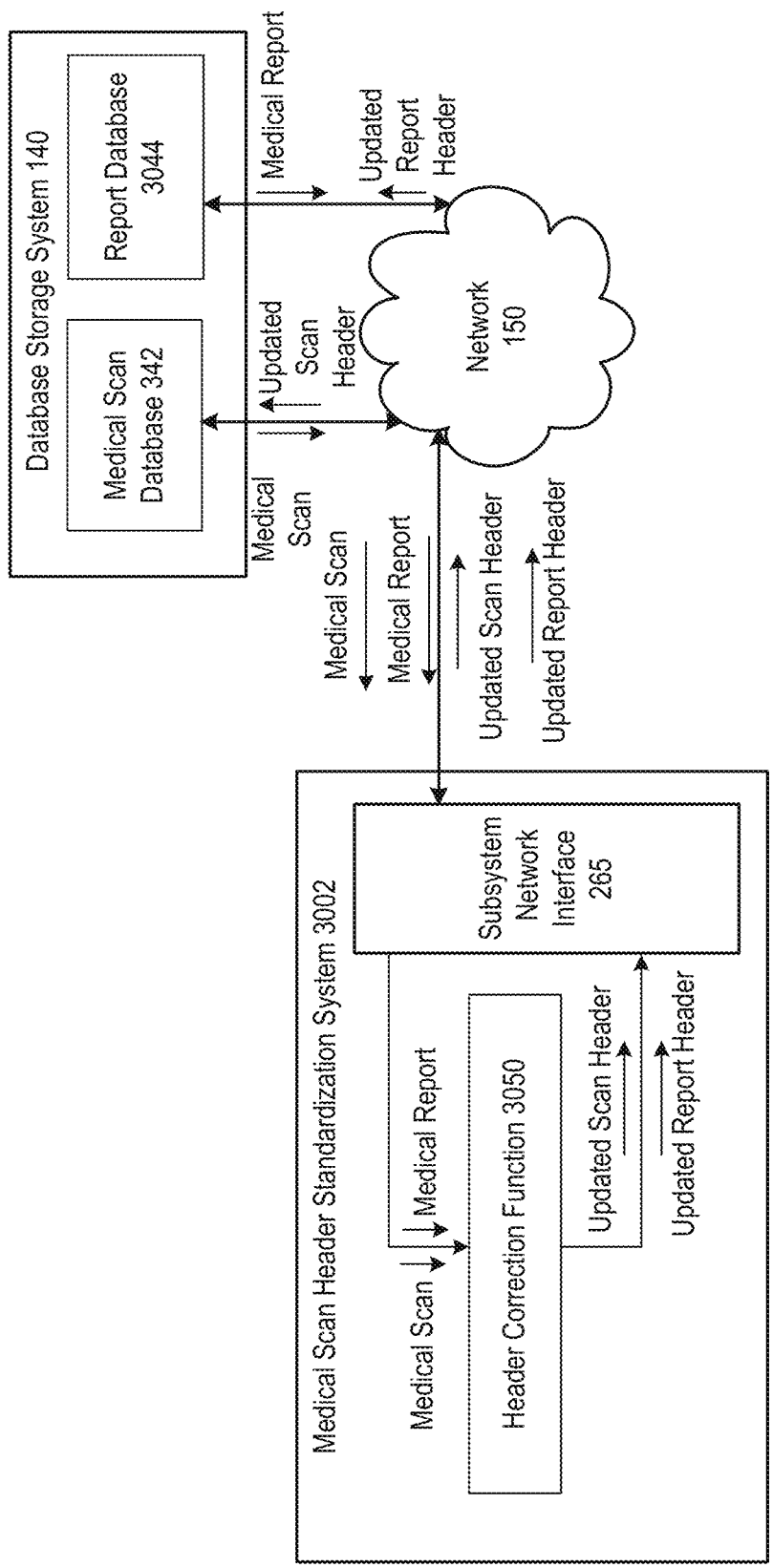

An updated header for both the medical scan and medical report can both be generated, as illustrated in FIG. 12D, based on information of the current header of the scan, the current header of the medical report, and/or based on text extracted from the medical scan and the corresponding report. The medical scan header standardization system 3002 can similarly store header standardization data 3030 for report headers, where some or all of the set of fields and corresponding fixed set of entries and/or formatting rules are the same or different for medical scan headers and for medical report headers. In some embodiments, updated headers for medical reports are generated without utilizing a corresponding medical scan. The patient identifier detection function of the de-identification system can be utilized to identify text in the medical report corresponding to one or more of the header fields of the report, and can be utilized to detect errors in the report header and/or correct errors in the report header. Another text identifier function trained to identify terms in the medical report corresponding to one or more header fields can similarly be trained and performed in this fashion.

Other medical scans and/or medical reports of the same or different study for a same patient can also be fetched from the medical scan database and/or medical report database, and can similarly be utilized to detect errors in the header of the medical scan and/or to determine one or more of the fixed set of standardized entries for one or more field. For example, all of the medical scans and/or medical reports for a same patient can be fetched based on a patient identifier entry of the current header, based on a SOP UID entry of the current header, and/or based on other linking identifiers. Inconsistencies, such as differing patient name spellings, scan dates that are out of order, and/or other inconsistent information can automatically be detected and corrected to generate updated headers for this set of medical scans and medical reports. A consensus entry for an inconsistency can be determined based on the rules of the header standardization data 3030, and the consensus is applied to all corresponding fields to correct the inconsistency. Alternatively or in addition, the consensus entry can be determined by determining and/or selecting a majority or a plurality agreement for the entry amongst the set of headers. Fields of the additional headers of the set of retrieved scans and reports can also be corrected as needed to adhere to the header standardization data 3030 for transmission back to their respective databases.

In some embodiments, any errors or inconsistencies described herein are corrected or determined to remain unaltered based on user input. Rather than automatically "guessing" the appropriate entry for some or all of the header fields based on inconclusive information, the medical scan header standardization system 3002 can transmit to a client device any detected errors and/or inconsistencies between different scans, and/or any other header where the determined entry for one or more fields is determined to be inconclusive. Proposed corrections for some or all of these issues can also be generated by the medical scan header standardization system 3002 for transmission to the client device. A user of the client device can review the headers and/or proposed header corrections by utilizing an interactive interface. In some embodiments, the interactive interface displays this information in conjunction with the medical scan. User input entered by the user in response to a prompt by the interactive interface can indicate the appropriate fields and/or resolve some or all inconsistencies. This can be transmitted back to the medical scan header standardization system 3002. The user input can override the updated headers generated by the medical scan header standardization system 3002. Alternatively, the user input can be taken into consideration when ultimately selecting the appropriate updated header, but does not necessarily override the updated headers selected by the medical scan header standardization system 3002. The client device can also receive some or all updated headers generated by the medical scan header standardization system 3002 as part of a quality assurance process, allowing a user to inspect and/or correct the updated headers generated automatically by the medical scan header standardization system 3002. In some embodiments, all of the updated headers are generated automatically without any of this user intervention.

The medical scan header standardization system 3002 can utilize some or all of the steps and/or functionality discussed in conjunction with the standardized header formatting function performed by the annotating system 2612 in performing the header correction function 3050 to generate updated headers, and can utilize some or all of the standardized header formatting function parameters discussed in conjunction with the annotating system 2612. The medical scan header standardization system 3002 can be utilized to standardize de-identified headers of de-identified medical scans only, for example ensuring that PHI is protected from access by the medical scan header standardization system 3002, the medical scan database 342, and/or the network. Alternatively, the medical scan header standardization system 3002 can be utilized to standardize original headers that include PHI, for example, ensuring that fields that include PHI also adhere to a standardized format. For example, the medical scan header standardization system 3002 can be integrated within the medical picture archive integration system 2600 for utilization before and/or after de-identification, as discussed in conjunction with FIGS. 14A and 14B.

Figure 12E:
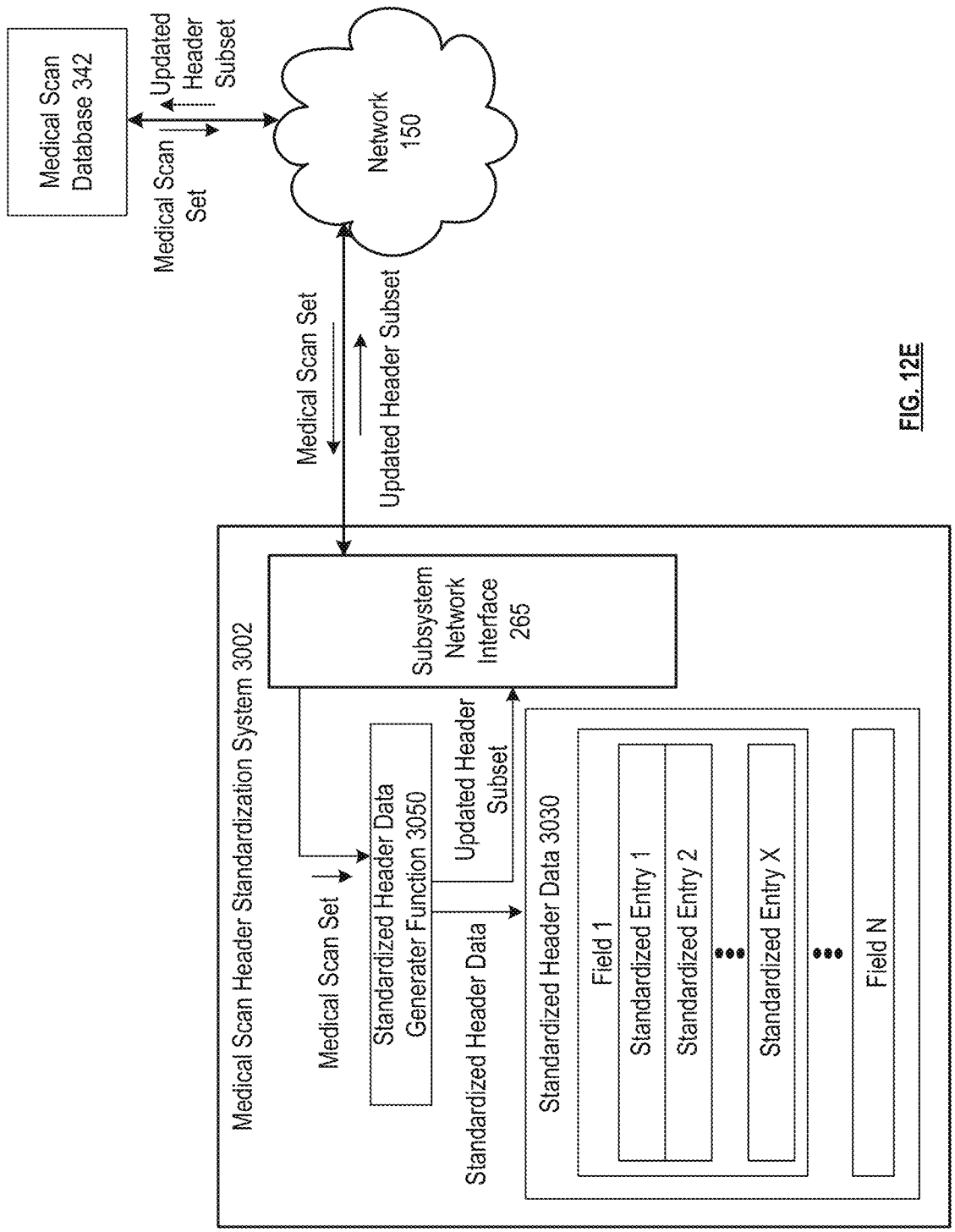

Some or all of the formatting rules, dependency requirements, and/or fixed entries for one or more fields of the header standardization data 3030 can be automatically determined by the medical scan header standardization system 3002. As shown in FIG. 12E, the medical scan header standardization system 3002 can receive a plurality of medical scans from the medical scan database. For example, these medical scans can be known to have headers with standardized headers, and the fixed entries can include the entries of these medical scans. The dependency requirements can be determined based on determining pairs and/or other sets of multiple entries for different fields that are present in at least one medical scan entry are allowed, and determining or temporarily setting pairs and/or other sets of multiple entries that are never present in any medical scan headers as not allowed and/or inconclusive. The dependency requirements for one or more properties can be determined automatically by performing one or more medical scan analysis functions on the medical scans to identify properties, and these properties can be mapped to the corresponding header fields as acceptable (but not necessarily required) dependencies. The determine number and/or ordering of the fixed set of fields can also be determined. Subsets of optional and/or mandatory fields can also be determined. In some embodiments, only headers of the set of medical scans are received, without image data or other data of the medical scans.

Some medical scan analysis functions utilized by the medical scan header standardization system 3002 can be trained by utilizing this set of medical scans as a training set, for example, where the one or more fields of their standardized headers are considered truth data and are utilized as output labels or an output feature vector, and where the image data of the medical scans are utilized as input feature vectors. For example, a scan type detection function and/or other medical scan analysis function that automatically generates inference data indicating a modality of the medical scan, an anatomical region of the medical scan, other scan classifier data 420 header fields, a diagnosis of the medical scan, an urgency of the medical scan, or other header fields as described herein can be trained in this fashion. One or more text identifying functions can similarly be trained in this fashion. These trained medical scan analysis functions can be performed on incoming medical scans to generate original header fields for the corresponding fields, to detect errors in one or more of the corresponding fields, and/or to correct one or more of the corresponding fields. These medical scan analysis functions generated by and/or performed by the medical scan header standardization system 3002 can be stored in and accessed from the medical scan analysis function database 346. In some embodiments, some or all of the fixed set of entries for one or more fields and/or formatting information is sent as direct instructions from a client device or another subsystem 101.

The set of medical scans utilized to generate some or all of the header standardization data 3030 can include medical scan headers generated under no standardization rules and/or loose standardization rules. The medical scan header standardization system 3002 can generate some or all of the header standardization data 3030 automatically based on determining common entries determined to describe the same information and/or based on determining common formatting. Histograms or other aggregate analysis of actual entries or formatting of entries can be determined for some or all of the fields, and can be utilized to determine the most common entries and/or most common format, to determine the level of disagreement between formatting and/or actual entries for one or more fields, and/or can determine trends in the formatting and/or actual entries. For example, the medical scan header standardization system 3002 can determine a subset of date fields are in a "MM/DD/YYYY" format, and that a second subset of dates is in a "MM-DD-YY" format. The medical scan header standardization system 3030 can determine that the "MM/DD/YYYY" format should be selected as the standardized date format based on determining this format is utilized in a majority and/or plurality of date entries, and/or based on determining this format corresponds to a most similar format to an average format determined across all date entries. The medical scan header standardization system 3002 can determine that one subset of field entries include "Computerized Tomography: Chest", a second subset includes "Chest CT" and a third subset includes "CT of chest". The medical scan medical scan header standardization system 3030 can determine that "Computerized Tomography: Chest" is a standardized entry for this field. For example, the header standardization system 3030 can perform a trained scan type detection function on the set of medical scans to group the medical scans into subsets by automatically determined scan type. For some or all of the groups, the medical scan header standardization system 3002 can evaluate the entries for one or more scan type fields to determine the most popular entry and/or to determine an average entry. Furthermore, across all of the groups, a formatting consensus can be reached based on overall trends in formatting. For example, "Computerized Tomography: Chest" may be selected as a standardized entry as a result of determining that "MODALITY: ANATOMICAL REGION" is the standardized format for the field, for example, based on determining this corresponds to a most popular format and/or a consensus format. Other trends can be evaluated to determine number and/or ordering of the fixed set of fields, to determine which fields are mandatory, and/or to determine dependency requirements.

Once the header standardization data 3030 is determined, headers for some or all of the set of medical scans can be updated, where errors are detected and/or corrected as described herein. The header standardization data 3030 can be sent to a client device for review via an interactive interface, and the client device can transmit edits to the header standardization data 3030 generated based on user input. The header standardization data 3030 can be stored in a database and/or sent to other subsystems 101 for use to provide standardization across the system and/or to help ensure original generation of headers adhere to the standardization.

In some embodiments, multiple sets of header standardization data 3030 are stored for a corresponding set of multiple medical entities and/or geographic regions, based on differing preferences across these different entities. In such embodiments, a global set of header standardization rules can still be used internally by the system to ensure standardization for training data and other internal uses, where secondary headers that adhere to the global set of header standardization rules are generated for and mapped to medical scans in the system, while preserving their primary headers that adhere to their own set of header standardization data 3030 dictated by their corresponding medical entity and/or geographic region.

FIGS. 13A and 13B illustrate embodiments of an accession number correction system 3004. The accession number correction system 3004 is operable to correct accession numbers or other linking identifiers that are missing and/or incorrect for medical scans and/or medical reports to link medical scans and their corresponding medical reports in storage.

As shown in FIGS. 13A-13B, the accession number correction system 3004 can communicate bi-directionally, via network 150, with the medical scan database 342, a report database 3044, and/or other databases of the database storage system 140. While not shown in FIGS. 13A-13B, the accession number correction system 3004 can further communicate bi-directionally, via network 150, with one or more client devices 120, and/or one or more subsystems 101 of FIG. 1. In some embodiments, the accession number correction system 3004 is an additional subsystem 101 of the medical scan processing system 100, implemented by utilizing the subsystem memory device 245, subsystem processing device 235, and/or subsystem network interface 265 of FIG. 2A. As described in further detail in FIGS. 15A-15B. The medical scan database 342 can correspond to a PACS server and/or medical picture archive system 2620. The report database 3044 can correspond to a RIS and/or report database 2625.

In some embodiments, the accession number correction system 3004 is implemented by utilizing, or otherwise communicates with, the central server 2640. For example, some or all of the databases of the database storage system 140 are populated with de-identified data generated by the medical picture archive integration system 2600. In some embodiments, the accession number correction system 3004 can receive de-identified medical scans, annotation data, and/or reports directly from the medical picture archive integration system 2600. For example, the accession number correction system 3004 can request de-identified medical scans, annotation data, and/or reports that match requested criteria, for example, corresponding to scan criteria and/or report criteria generated by the accession number correction system 3004 as discussed herein. In some embodiments, some or all of the accession number correction system 3004 is implemented by utilizing other subsystems 101 and/or is operable to perform functions or other operations described in conjunction with one or more other subsystems 101. In particular, the accession number correction system 3004, or some or all steps and/or functionality described in conjunction with the accession number correction system 3004, can be implemented in or otherwise utilized by a medical scan header standardization system 3002 to rectify missing or incorrect accession numbers in medical scan headers and/or report headers to generate updated headers as described herein. Alternatively, the accession number correction system 3004 can be implemented as a separate subsystem 101 from the medical scan header standardization system 3002.

Accession numbers can link medical scans stored by a PACS or other medical scan database to corresponding reports stored separately in a RIS or other report database. Similar to the problems described that result from non-standardized headers, missing and/or incorrect accession numbers due to typos or other human error can lead to missing links between medical scans and medical reports, and/or lead to incorrect links between medical scans and non-corresponding medical reports. This can lead to problems when hospital systems or other medical entities wish to retrieve patient data and/or keep information organized, as this could cause a patient file to include missing and/or mismatched data. Furthermore, if an inference function of one or more subsystems 101 is trained by utilizing medical scans and corresponding medical reports, missing or mismatched pairs can cause improper training data and can lead to poor performance by the trained model. Additionally, de-identification of medical scans that utilizes a corresponding medical report as described herein cannot be performed properly if the corresponding medical report cannot be found due to a missing or incorrect accession number.

Even if these missing and/or incorrect accession numbers are detected, manual intervention to locate the correct corresponding scan and/or report can be timely and/or ineffective. The accession number correction system 3004 can automatically that an accession number missing or incorrect, and can automatically correct such missing and/or incorrect accession numbers to provide proper links between medical scans and corresponding medical reports. This improves existing systems by ensuring that data is organized properly, by proactively and automatically preventing the need to manually locate a medical scan or medical report that is not appropriately linked, by improving the process of generating training data for medical scan analysis functions, and by enabling de-identification of medical scans by utilizing corresponding medical reports.

As used herein, an accession number can correspond to a linking identifier of a header and/or metadata of a medical scan that indicates a corresponding medical report. For example, the corresponding medical report can be indicated as a result of a header and/or metadata of the medical report including the same accession number. As used herein, a corresponding medical report of a medical scan indicates a medical report that describes findings of the medical scan or otherwise includes text generated to describe features in the image data of the medical scan. Medical scans and medical reports can each include header fields and/or other metadata designated for an accession number, and a medical scan can be linked to medical report when the accession number of the medical scan matches the accession number of the medical report. Correct accession numbers can be unique, where only a linked medical scan and medical report will include a particular, matching accession number.

An accession number can be determined to be missing when a corresponding header field includes a null value and/or when no accession number exists in a header and/or metadata of a medical scan or a medical report. An accession number can be determined to be incorrect when an accession number of a medical scan is present, but no medical report exists with the same accession number. An accession number can similarly be determined to be incorrect when an accession number of a medical report is present, but no medical scan exists with the same accession number. An accession number can be determined to be incorrect when an accession number of a medical scan is present, when a medical report exists with the same accession number as the medical scan, but the medical report does not correspond to the medical scan because it does not describe the medical scan and/or because it corresponds to a different medical scan instead. An accession number can be determined to be incorrect when multiple medical reports that describe different medical scans include the same accession number. An accession number can similarly be determined to be incorrect when multiple medical scans that are not all described by the same medical report include the same accession number. In some embodiments, an accession number is determined to be correct if and only if exactly one medical scan includes the accession number, exactly one medical report includes the same accession number, and the exactly one medical scan is described by the exactly one medical report.

As described herein, an accession number is unique for each medical scan/medical report pair, where each accession number indicates a single medical scan and a corresponding single medical report. In other embodiments, the same accession number of a single medical report can be included in multiple medical scans of the same study or otherwise be included in multiple medical scans indicated in or described by the single medical report. The same accession number of a single medical scan can be included in multiple medical reports that indicate or describe the single medical scan. Multiple medical scans and multiple medical reports can have the same accession number if the multiple medical scans are of the same study or are otherwise described by the multiple medical reports. A single medical scan can include multiple accession numbers indicating multiple corresponding medical reports that describe the medical scan. A single medical report can include multiple accession numbers indicating multiple medical scans that are described in the medical report. Any of these embodiments of accession numbers can similarly be determined to be missing and/or incorrect, and can be corrected based on identification of corresponding scans and/or reports.

In some embodiments, an accession number can correspond to other linking identifiers of medical scans to medical reports, and vice versa. These linking identifiers do not necessarily need to match. For example, a medical scan can include an identifier of a corresponding medical report, such as an identification number or unique identifier of the medical report itself. Similarly, the medical report can include an identifier of a corresponding medical scan, such as an identification number or unique identifier of the medical scan itself. A proper, two-way linking exists when a medical scan includes an identifier for a medical report, and when the medical report also includes an identifier back to the same medical scan. These linking identifiers can be determined to be missing and/or incorrect when this proper two-way linking does not exist, and can be similarly corrected by facilitating the proper two-way linking based on identification of a corresponding report for a given medical scan, or vice versa, as described herein.

FIG. 13A illustrates determining a medical report to be properly linked to a medical scan with a missing and/or incorrect accession number. When a medical scan is not properly linked to a corresponding medical report, a set of possible medical reports can be fetched from a report database based on a report criteria query generated by performing a report criteria generator function 3065. The correct, corresponding medical report can be selected from the set of possible medical reports based on a comparison function 3070 performed on the medical scan and corresponding medical report indicates a favorable comparison between the medical scan and corresponding medical report. Once this corresponding medical report is determined, the medical scan and medical report can each be assigned a matching accession number so that they are linked in storage.

A medical scan with a missing and/or incorrect accession number can be received by the accession number correction system 3004 via the network. The medical scan can be received in response to determining the accession number is missing or incorrect, for example, based on an indication from another subsystem 101 and/or from a client device 140. The medical scan can be received in response to a query to the medical scan database for medical scans that have missing accession numbers. The medical scan can be retrieved in a plurality of medical scans, and the accession number correction system 3004 can first determine which of the plurality of medical scans have missing or incorrect accession numbers, for example, by first determining a subset of medical scans in the plurality of received medical scans that have correct accession numbers. This subset can be determined by utilizing the accession number of these medical scans to fetch corresponding medical reports from the report database 3044. A final subset can be further determined by performing the comparison function 3070 to determine whether the fetched medical reports compare favorably to the corresponding medical scans in the subset to determine the final subset. Medical scans that are not included in the final subset can be identified as having missing and/or incorrect accession numbers that require correction.

The accession number correction system 3004 can forego generating report criteria and performing the comparison function for medical scans received that are determined not to require correction of their accession number. The accession number correction system 3004 can transmit the same accession number back to the medical scan database for the medical scan in response to determining no correction is required. Alternatively, the accession number correction system 3004 can forego any transmission of an accession number for the medical scan in response to determining no correction is required.

The accession number correction system 3004 can determine accession number of a medical scan does not to require correction in response to determining no additional medical scans include the same accession number, in response to determining exactly one medical report includes the same accession number, and/or in response to determining the medical scan is described by the exactly one medical report. In some embodiments, all of these first set of conditions must be determined to be true for the accession number to be determined to be correct. In some embodiments, the accession number is determined to be missing or incorrect if any one of these first set of conditions does not hold. Alternatively, the accession number correction system 3004 can determine accession number of the medical scan does not to require correction in response to determining no additional medical scans include the same accession number, in response to determining multiple reports includes the same accession number, and in response to determining the all of the multiple reports describe the medical scan. In some embodiments, the accession number is determined to be missing or incorrect if any one of these second set of conditions does not hold. Alternatively, the accession number correction system 3004 can determine accession number of the medical scan does not to require correction in response to determining at least one additional medical scan includes the same accession number, in response to exactly one reports includes the same accession number, and in response to determining the all of the at least one additional medical scans are described by the exactly one report. In some embodiments, the accession number is determined to be missing or incorrect if any one of these third set of conditions does not hold.

Once the medical scan is determined to have the missing and/or incorrect accession number, the report criteria generator function can be performed to determine report criteria for a medical report that would appropriately correspond to the medical scan. This can include extracting one or more entries from one or more header fields from the medical scan, such as a unique patient identifier, a patient name or other patient identifying information described herein, temporal data such as time and/or date of the scan, an identifier of a hospital and/or radiologist that administered the scan, an SOP UID of the scan, and/or any other information from the header of the medical scan that may be expected in a corresponding medical report. The determined report criteria can be indicated in a report criteria query transmitted to the report database 3044. The query can indicate that all of the extracted fields must match and/or can indicate that a threshold number of fields must match.

Alternatively or in addition, performing the report criteria generator function can include automatically generating diagnosis data and/or otherwise generating determining features of the image data itself. This can include performing one or more medical scan image analysis functions on the image data to automatically extract text from the medical scan, to automatically generate diagnosis data for the medical scan, and/or to automatically detect unique features of the medical scan. This medical scan image analysis function can correspond to any inference function and/or medical scan analysis function described herein, and can utilize a computer vision model trained on a training set of medical scans by utilizing the medical scan image analysis system 112. This medical scan image analysis function can correspond to the patient identifier detection function of the de-identification system 2608.

The extracted text, diagnosis data, and/or unique features detected in the medical scan determined as output to the one or more medical scan image analysis functions performed on the image data can be utilized to generate some or all of the report criteria transmitted in the query to the report database. Other information extracted from the image data, header, and/or metadata of the medical scan that can be utilized to determine a corresponding medical report can also be extracted and included in the report criteria query.

Alternatively or in addition, performing the report criteria generator function can include generating a plurality of similar accession numbers. For example every possible accession number that has only one character difference from the incorrect accession number of the medical scan can be generated and transmitted to the report database, and all reports with matching accession numbers can be retrieved. This can be utilized to catch a typo in typing the accession number. Alternatively or in addition, performing the report criteria generator function can include generating a query for reports that meet the rest of the generated criteria, and that also have a missing and/or incorrect accession number. For example, an indicator that an accession number is incorrect or inconclusive can be indicated in the database. This can ensure that only reports with missing and/or incorrect accession numbers are evaluated.

In response to receiving the report criteria query, the report database 3044 can transmit a set of medical reports to the accession number correction system 3004. In some embodiments, exactly one medical report determined to match or most closely match the report criteria is transmitted. In other embodiments, multiple medical reports determined to compare favorably to some or all of the report criteria is transmitted back to the accession number correction system 3004. In other embodiments, no medical reports are determined to compare favorably, and no medical reports are transmitted. In such embodiments, the accession number correction system 3004 can regenerate report criteria by generating looser criteria that encompasses a greater number of possible medical reports for transmission to the report database, and can continue generating looser criteria until at least one medical report is received.

A comparison function 3070 can be performed on the medical scan and each of the received medical reports. The comparison function 3070 can take a medical scan/medical report pair as input, and can generate a comparison value indicating how similar or dissimilar the medical scan is to the medical report. The comparison value can be compared to a predefined comparison threshold to determine if the comparison value indicates a sufficiently favorable comparison that indicates the medical scan does indeed corresponds to the medical report.

In some embodiments, each medical report received from the report database 3044 is fed into the comparison function 3070 with the medical scan to generate comparison values for every one of the set of medical reports. The one of the set of medical reports with a most favorable comparison value can be determined to be the corresponding medical report. In some embodiments, a comparison threshold must be met for a medical report to be selected as corresponding to the medical scan, where the one of the set of medical reports with the most favorable comparison value is only selected as corresponding to the medical scan if the comparison value also compares favorably to the comparison threshold.

In other embodiments, the set of medical reports are fed into the comparison function 3070 one at a time with the medical scan until an output comparison value compares favorably to the comparison threshold. The medical report that resulted in the output comparison value that compared favorably to the comparison threshold can be selected as the corresponding medical report, and the accession number correction system 3004 can forego comparison of any remaining medical reports that have not yet been compared to the medical scan.

In some embodiments, a subset of the set of medical reports is first generated by determining which ones of the set of medical reports have missing and/or incorrect accession numbers themselves, where only these improperly linked medical reports are evaluated as candidates for the corresponding medical report. Determining which ones of the set of medical reports have missing and/or incorrect accession numbers can be performed as discussed in conjunction with FIG. 13B. In such embodiments, the comparison function 3070 is only performed on this subset of the set of medical reports. Alternatively, the comparison function 3070 is performed on this subset of the set of medical reports first, and if no favorable comparison is identified, the comparison function 3070 is then performed on remaining ones of the set of medical reports.

Performing the comparison function 3070 can include generating a feature vector for the medical scan and a corresponding feature vector of the medical report, where corresponding fields of the feature vectors are compared to generate the comparison value. Generating the feature vectors can include extracting one or more header fields of the medical scan and a corresponding one or more header fields of the medical report, where some or all fields of the feature vectors include the one or more header fields. In this fashion, comparing the feature vectors includes comparing corresponding header fields.

Alternatively or in addition, generating the medical scan feature vectors can include performing inference functions or other medical scan analysis function as described herein. For example, entries of one or more diagnosis fields of the medical scan feature vector can be generated by performing a medical scan image analysis function on the medical scan to detect and/or characterize one or more abnormalities and/or indicates a diagnosis, by utilizing a computer vision model trained on a training set of medical scans, for example, trained by the medical scan image analysis system 112. Entries of one or more corresponding diagnosis fields of the medical report feature vector can be generated by performing a natural language function on the medical report to detect text that characterizes or otherwise describes one or more abnormalities and/or indicates a diagnosis, by utilizing a natural language model trained on a training set of medical reports, for example, trained by the medical scan natural language analysis system 114. Some of the entries of the medical scan feature vector can correspond to text such as patient identifying text extracted from the image data of the medical scan, and corresponding entries of the medical report feature vector can correspond to patient identifying text extracted from the text of the medical report. The patient identifier detection function of the de-identification system 2608 can be performed on the image data of the medical scan and/or the text of the medical report to populate some fields of the medical scan feature vector and/or the medical report feature vector, respectively.

The comparison value can compare favorably to the comparison threshold when a threshold number of feature vector fields match exactly, for example, when a patient identifier, temporal fields, and/or a SOP UID matches exactly. In some embodiments the threshold number of feature vector fields that must match exactly include at least one particular feature vector fields that must match exactly, such as the field corresponding to the unique patient identifier. In some embodiments, if one or more predetermined fields do not match, the comparison value will automatically compare unfavorably to the comparison threshold. As an example, if entries of unique patient identifier fields do not match, the comparison value will never compare favorably to the comparison threshold, and the accession number correction system 3004 will never determine that the input medical scan and input medical report are meant to be linked.

A more favorable comparison value can be assigned to medical scan/medical report pair with a first number of matching fields that is greater than a second number of matching fields of another medical scan/medical report pair. The comparison value can be further weighted for different feature vector fields. The assigned weights can be based on fields that more substantially indicate the medical scan and medical report should be linked if these fields match, for example, where unique patient identifier is assigned a weight that is higher than weights assigned to patient name or medical institution. The sum of the weights of matching fields can be utilized to determine the comparison value, where a higher sum corresponds to a more favorable comparison value than a lower sum.

In some embodiments, a comparison value can still compare favorably to the comparison threshold when a threshold number of fields are substantially similar, for example, when two fields are determined to be substantially similar when they differ by less than a threshold number of characters and/or are determined to have a difference of meaning within a threshold. For example "Frank Smith" and "Frank J. Smith" can be determined to be substantially similar patient name entries, and/or "12:52 pm, Oct. 12, 2018" can be determined to be substantially similar to "12:53 pm, Oct. 12, 2018." The entry comparison function of the medical scan header standardization system 3002 can be performed to determine this difference between feature vector fields. In some embodiments, a set of fields that are allowed to be substantially similar, such as automatically detected diagnosis data, patient name, and/or scan time, can be identified and utilized in generating the comparison value. In particular, fields that correspond to standardized values of headers generated by the medical scan header standardization system 3002 can be required to match exactly, and fields that include unstructured text or other unstructured data can be required to substantially match.

In some embodiments, feature vector fields corresponding to accession number are weighed more heavily when the accession number of the medical report is determined to have missing or incorrect accession numbers. Determining one of the set of medical reports has a missing and/or incorrect accession number can otherwise cause the comparison function 3070 to generate a comparison value with a higher comparison value than if the accession number was present and/or correct.

In some embodiments, no medical report is selected because none of the comparison values compare favorably to the comparison threshold. In such embodiments, the accession number correction system 3004 can continue generating looser report criteria for transmission to the medical report database, and can continue performing the comparison for subsequently received medical reports until a medical report with comparison value that compares favorably to the comparison threshold is determined. In some embodiments, the accession number correction system 3004 can perform the comparison for all reports stored in the report database until a medical report with comparison value that compares favorably to the comparison threshold is determined. In some embodiments, if no medical reports are determined to compare favorably, the accession number of the medical scan can be updated to a standardized "inconclusive" value, indicating the accession number correction system 3004 has searched for a corresponding medical report but no corresponding medical reports were found.

In some embodiments, the accession number correction system 3004 can determine to transmit one or more of the possible medical reports, such as one or more reports with the highest comparison values, to a client device in conjunction with the medical scan for display via a display device, and a user of the client device can interact with an interactive interface via user input to select one of the set of possible medical reports that corresponds to the medical scan and/or to indicate none of the set of possible medical reports correspond to the medical scan. The accession number can be assigned to a selected medical report indicated based on the user input and/or can be assigned the standardized "inconclusive" value based on the user input. The accession number correction system 3004 can determine to transmit one or more possible medical reports only when none of the possible reports resulted in a comparison value that compared favorably to the comparison threshold.

In some embodiments, the existing accession number of the medical scan and medical report are included in corresponding feature vector fields. When the existing accession numbers are determined to be substantially similar, for example, differing by a threshold number of characters, this can lead to a comparison value that compares favorably to the comparison threshold when at least a threshold number of other fields match and/or are substantially similar. This threshold number can be smaller than a threshold number required when the existing accession numbers are not substantially similar. In this fashion, potential typos in accession number can be detected. Determining other information such as patient identifying information or diagnosis information of the medical scan and medical report compares favorably can confirm that the accession number discrepancy corresponded to a typo, and were meant to match.

Some or all of the mechanisms utilized to identify matching patient identifying information of the medical scan and the medical report in performing de-identification of the medical scan and the medical report as described in conjunction with the de-identification system 2608 can be utilized to in generating the medical scan feature vector and medical report feature vector to include this extracted information and/or to compare corresponding information to determine whether or not this information matches.

Once a corresponding medical report is selected for the medical scan based on the corresponding comparison value, the accession number correction system 3004 can facilitate linking the medical scan and corresponding medical report properly in storage. This can include updating the missing or incorrect accession number of the medical scan by selecting the existing accession number of the selected medial report as the new accession number of the medical scan. As illustrated in FIG. 13A, the updated accession number to the medical scan database for storage in conjunction with the medical scan, to replace the previous incorrect accession number and/or to populate the missing accession number. An identifier of the selected report can be included in the transmission to identify which report the updated accession number corresponds to. This can also include generating an updated header as discussed in conjunction with the medical scan header standardization system 3002 to include the updated accession number, and transmitting the updated header to the medical scan database to replace a previous header. This can also include reformatting the medical scan to include the updated accession number, and transmitting the reformatted medical scan to replace the prior version of the medical scan in the medical scan database.

Rather than automatically assigning the accession number of the medical report to the medical scan, the accession number correction system 3004 can determine which accession number to utilize. For example, the accession number correction system 3004 can determine to assign an existing accession number of the medical report to the medical scan when the accession number of the medical scan is missing, when the existing accession number of the medical scan links to an incorrect, non-corresponding medical report, and/or when the accession number of the medical report is non-null and does not map to any incorrect, non-corresponding medical scans.

Similarly, the accession number correction system 3004 can instead determine to assign the existing accession number of the medical scan to the medical report. This can be in response to determining that the medical report has a missing accession number, in response to determining the existing accession number of the medical report links the medical report to an incorrect, non-corresponding medical scan, and/or in response to determining the accession number of the medical scan is non-null and does not map to any incorrect, non-corresponding medical reports. In such embodiments, the updated accession number can be determined to be the existing accession number of the medical scan. This updated accession number can be transmitted to the report database for storage in conjunction with the medical report. This can also include generating an updated header for the medical report as discussed in conjunction with the medical scan header standardization system 3002 to include the updated accession number, and transmitting the updated header to the report database to replace a previous header. This can also include reformatting the medical report to include the updated accession number, and transmitting the reformatted medical report to replace the prior version of the medical report in the report database.

In some embodiments, the accession number correction system 3004 can determine to generate a new accession number that does not correspond to either accession number of the medical scan/medical report pair. The new updated accession number can be sent to both the medical scan database and report database to be mapped to the medical scan and medical report, respectively, in storage. Updated headers and/or a reformatted medical scan and reformatted medical report can similarly be generated for transmission back to the respective database for storage. The new accession number can be determined based on determining the new accession number is not in use by other linked pairs. The new accession number can be determined based on a fixed set of accession number options indicated in header standardization data 3030 and/or a standardized accession number format indicated in header standardization data 3030.

As described previously, the accession number of the medical scan can be determined to be incorrect when an accession number of a medical scan is present, when a medical report exists with the same accession number as the medical scan, but the medical report does not correspond to the medical scan because it does not describe the medical scan and/or because it corresponds to a different medical scan instead. For example, this is determined in response to the accession number correction system 3004 fetching the corresponding medical report from the report database based on the accession number, perform the comparison function 3070, and determining the comparison value does not compare favorably to the comparison threshold. In such embodiments, once the appropriate medical report is determined for the medical scan, the medical scan's accession number is updated, and the original medical report that was previously linked to the medical scan no longer has a medical scan linked to its accession number. In some embodiments, the accession number correction system 3004 can determine whether an additional medical scan includes the same accession number as the original medical report based on a query to the medical scan database, and can perform the comparison function on this medical scan and the original medical report to determine if the accession number is appropriate. If not, or if no medical scan included the same accession number, the accession number for this medical report can be corrected by utilizing the steps described in FIG. 13B.

FIG. 13B illustrates determining a medical scan to be linked to a medical report with a missing and/or incorrect accession number. When a medical report is not properly linked to a corresponding medical scan, a set of possible medical scans can be fetched from a medical scan database based on a scan criteria query generated by performing a scan criteria generator function 3075. The corresponding medical scan can be selected from the set of possible medical scans based on the comparison function 3070 performed on the medical report and corresponding medical scan indicating a favorable comparison between the medical report and corresponding medical report. Once the corresponding medical scan is determined, the medical report and corresponding medical scan can each be assigned a matching accession number so that they are linked in storage.

A medical report with a missing and/or incorrect accession number can be received by the accession number correction system 3004 via the network. The medical report can be received in response to determining the accession number is missing or incorrect, for example, based on an indication from another subsystem 101 and/or from a client device 140. The medical report can be received in response to a query to the report database for medical reports that have missing accession numbers. The medical report can be retrieved in a plurality of medical reports, and the accession number correction system 3004 can first determine which of the plurality of medical reports have missing or incorrect accession numbers, for example, by first determining a subset of medical reports in the plurality of received medical reports that have correct accession numbers. This subset can be determined by utilizing the accession number of these medical reports to fetch corresponding medical scans from the medical scan database 342. The subset can be further determined by performing the comparison function 3070 to determine whether the fetched medical scans compare favorably to the corresponding medical reports in the subset. Medical reports that are not included in the subset can be identified as having missing and/or incorrect accession numbers that require correction.

A scan criteria generator function 3075 can be performed on a medical report determined to have the missing or incorrect accession number. The scan criteria generator function 3075 can include some or all of the criteria determined by report criteria generator function 3065. For example, header fields can similarly be extracted and/or substantially similar accession numbers can be generated and included in the scan criteria. The scan criteria can indicate a request for only medical scans that meet the criteria and that also have missing and/or incorrect accession numbers. Performing the scan criteria generator function 3075 can further include performing a natural language function to extract text from the medical report to be included in the scan criteria, such as patient identifying information, diagnosis data, and/or other information extracted from the medical report that can be utilized to determine a corresponding medical scan. Performing the scan criteria generator function 3075 can include performing the patient identifier detection function of the de-identification system 2608.

A single medical scan or multiple medical scans can similarly be received from the medical scan database, transmitted by the medical scan database in response to receiving the scan criteria query. The set of received medical scans can be fed into the comparison function 3070 with the medical report to select a medical scan with a most favorable comparison value and/or to select a medical scan with a comparison value that compares favorably to the comparison threshold, as described in conjunction with FIG. 13A. An updated accession number for the medical report and/or selected medical scan can be determined as described in conjunction with FIG. 13A for transmission to the report database and/or medical scan database, respectively. An identifier of the medical report and/or selected medical scan is transmitted in conjunction with the updated accession number to indicate which medical report and/or selected medical scan the updated accession number corresponds to. An inconclusive value can be assigned to the medical report's accession number if none of the comparison values compare favorably to the comparison threshold. Some of the possible medical scans can be sent to a client device for review if none of the comparison values compare favorably to the comparison threshold, as discussed in conjunction with FIG. 13A, and the selected medical scan that corresponds to the medical report can be determined based on user input. Looser scan criteria can be continued to be generated to retrieve additional scans from the medical scan database if no medical scans are received from the medical scan database and/or if none of the comparison values compare favorably to the comparison threshold.

As described previously, the accession number of the medical report can be determined to be incorrect when an accession number of a medical report is present, when a medical scan exists with the same accession number as the medical report, but the medical report does not correspond to the medical scan because it does not describe the medical scan and/or because the medical scan corresponds to a different medical report instead. For example, this is determined in response to the accession number correction system 3004 fetching the corresponding medical scan from the medical scan database based on the accession number of the medical report, performing the comparison function 3070, and determining the comparison value does not compare favorably to the comparison threshold. In such embodiments, once the appropriate medical scan is determined for the medical report, the medical report's accession number is updated, and the original medical scan that was previously linked to the medical report no longer has a medical report linked to its accession number. In some embodiments, the accession number correction system 3004 can determine whether an additional medical report includes the same accession number as the original medical scan based on a query to the report database, and can perform the comparison function on this medical report and the original medical scan to determine if the accession number is appropriate. If not, or if no medical report included the same accession number as the original medical scan, the accession number for this medical scan can be corrected by utilizing the steps described in FIG. 13A.

In some embodiments, a plurality of medical scans and plurality of medical reports, such as all of the medical scans and/or all of the medical reports, can be retrieved from the medical scan database by the accession number correction system 3004. A subset of the plurality of medical scans and a subset of the plurality of medical reports can be determined to have missing or incorrect accession numbers as described herein. Alternatively, only medical scans and medical reports with missing, incorrect, or inconclusive accession numbers are requested from the medical scan database and report database in the first place. Rather than generating report criteria or scan criteria, each of the subset of medical scans can be compared to each of the subset of medical reports already determined to have incorrect or missing accession numbers by utilizing the comparison function 3070. For example, every possible medical scan/medical report pair of the subset of medical scans and subset of medical reports can be fed into the comparison function 3070 to generate the plurality of comparison values to be compared to the comparison threshold. Pairs of medical scans and corresponding medical reports with comparison values that compare favorably to the comparison threshold can be assigned matching accession numbers to link the pairs for transmission to the corresponding medical scan and/or medical report database accordingly as described herein.

FIGS. 14A-15B present example embodiments illustrating how the medical scan header standardization system 3002 and/or the accession number correction system 3004 can be integrated within the medical picture archive integration system 2600. The medical scans can correspond to DICOM images stored in the medical picture archive system 2620, and/or the medical reports can correspond to report data stored in the report database 2625. For example, as presented in FIG. 14A, de-identified medical scans can be sent from the de-identified image storage system 2610 to the medical scan header standardization system 3002. Parameters for the header correction function 3050 or for other functionality of the medical scan header standardization system 3002 can be sent to the medical scan header standardization system 3002 via network 2630. The de-identified header fields can be standardized, and these standardized fields can be sent to the medical picture archive system 2620 for storage. In some embodiments, these standardized fields replace previous versions of these fields, but the entire header is not updated so that the patient identifying information in the header can be maintained in the medical picture archive system. The de-identified medical scans can be sent in conjunction with their standardized headers to the central server system 2640, allowing the central server system 2640 to generate one or more inference functions for transmission to one or more subsystems 101 and/or for use by the annotating system 2612. The medical scan header standardization system 3002 can be integrated within the annotating system 2612. While not depicted in FIG. 14A, the accession number correction system 3004 can also be integrated within the medical picture archive integration system 2600 in the same fashion, operating on de-identified medical scans and de-identified medical images to generate accession numbers for transmission to the medical picture archive system 2620 for storage in conjunction with the corresponding medical scan and/or to the report database 2625 for storage in conjunction with the corresponding report.

While the implementation illustrated in FIG. 14A allows de-identified medical scans headers to be communicated to the central server system 262 via the network interface, it may be ideal to standardize all of the header fields, even those that include PHI. FIG. 14B illustrates an example embodiment that can be utilized to accomplish this. The header standardization can be implemented before de-identification of medical scans, where the medical scan header standardization system 3002 receives the medical scans and medical reports from the medical picture archive system 2620 and the report database 2625, respectively, as DICOM images and report data. The updated scan headers can be in a DICOM header format, generated for transmission back to the medical picture archive system 2620. The updated report headers can be transmitted to back to the report database 2625. The DICOM image and report data, along with their updated, standardized headers, can be sent to the de-identification system 2608 for processing. Alternatively, the medical scan header standardization system 3002 can be integrated within and/or share resources with the de-identification system 2608.

The accession number correction system 3004 can similarly be implemented before de-identification, as shown in FIGS. 15A and 15B. For example, the accession number correction system 3004 and the medical scan header standardization system 3002 can be integrated together before de-identification and/or integrated within and/or share resources with the de-identification system 2608. As shown in FIG. 15A, the process illustrated in FIG. 13A can be performed. In particular, a DICOM image can be received from the medical picture archive system 2620, and a report query indicating report criteria can be generated in response to determining the DICOM image has a missing or incorrect accession number. The report criteria can be transmitted to the report database 2625. A set of reports can be received from the report database 2625 in response. An updated accession number for the DICOM image and/or for a corresponding one of the set of reports can be determined as discussed herein. The updated accession number for the DICOM image can be transmitted to the medical picture archive system 2620 with a corresponding identifier of the DICOM image. If the accession number of the selected medical report is alternatively or similarly updated, the updated accession number for the selected medical report can be transmitted to the report database 2625 with an identifier for the selected medical report. The DICOM image data, and the report data for the selected medical report determined to correspond to the DICOM image, can be sent to the de-identification system 2608 for processing.

As shown in FIG. 15B, the process illustrated in FIG. 13B can be performed. In particular, a report data for a medical report can be received from the report database 2625, and a scan query indicating scan criteria can be generated in response to determining the medical report has a missing or incorrect accession number. The scan criteria can be transmitted to the medical picture archive system 2620. A set of DICOM images can be received from the medical picture archive system 2620 in response. An updated accession number for the medical report and/or for a corresponding one of the set of DICOM images can be determined as discussed herein. The updated accession number for the medical report can be transmitted to the report database 2625 with a corresponding identifier of the medical report. If the accession number of the selected DICOM image is alternatively or similarly updated, the updated accession number for the selected DICOM image can be transmitted to the report database 2625 with an identifier for the selected medical report. The report data, and the DICOM image data for the selected DICOM image determined to correspond to the medical report, can be sent to the de-identification system 2608 for processing.

While not depicted in FIGS. 14A-15B, the report database 2625 can be configured to communicate with the medical picture archive system 2620, as illustrated in FIG. 8E. The medical picture archive integration system 2600 can transmit queries to the report database 2625 via the medical picture archive system 2620 such as report criteria, requests for reports, updated headers for storage and/or updated accession numbers for storage. The medical picture archive system 2620 forwards the queries to the report database 2625, receives responses to the queries such as report data from the report database 2625, and forwards the responses to the medical picture archive integration system 2600.

In various embodiments, a medical scan header standardization system 3002 includes at least one processor and a memory that stores executable instructions that, when executed by the at least one processor, cause the medical scan header standardization system to determine a set of standard DICOM headers based on determining a standard set of fields and based on further determining a standard set of entries for each of the standard set of fields. The medical scan header standardization system 3002 receives a DICOM image via a network, and determines that a header of the DICOM image is incorrect. The medical scan header standardization system 3002 determines a selected one of the set of standard DICOM headers to replace the header of the DICOM image, and transmits the selected one of the set of standard DICOM headers, via the network, to a medical scan database for storage in conjunction with the DICOM image.

In various embodiments, an accession number correction system 3004 includes at least one processor and a memory that stores executable instructions that, when executed by the at least one processor, cause the accession number correction system to receive a first DICOM image from a PACS server that stores a plurality of DICOM images. The accession number correction system 3004 determines that an accession number of the first DICOM image does not link to any corresponding one of a plurality of medical reports. Medical report criteria is generated based on the first DICOM image, and a first query indicating the medical report criteria is transmitted to a report database that stores the plurality of medical reports. The accession number correction system 3004 receives a set of medical reports from the report database in response to the first query, and performs a comparison function on the first DICOM image and at least one of the set of medical reports to generate a comparison value for each of the at least one of the set of medical reports. The accession number correction system 3004 determines a selected one of the set of medical reports that corresponds to the first DICOM image by determining the comparison value corresponding to the selected one of the set of medical reports compares favorably to a comparison threshold.

In some embodiments, updated report header data is generated for the selected one of the set of medical reports, where the updated report header data includes the accession number of the first DICOM image. The updated report header data is transmitted to the report database for storage in conjunction with the selected one of the set of medical reports. Alternatively or in addition, updated DICOM image header data is generated for the first DICOM image, where the updated DICOM image header data includes the accession number of the selected one of the set of medical reports. The updated DICOM image data is transmitted to the PACS server for storage in conjunction with the first DICOM image.

FIG. 16 presents a flowchart illustrating a method for execution by a medical scan header standardization system 3002 that stores executional instructions that, when executed by at least one processor, cause the medical scan header standardization system 3002 to perform the steps below. Alternatively or in addition, some or all of the steps of FIG. 16 can be performed by the accession number correction system 3004.

Step 4002 includes determining a set of DICOM headers based on determining a standard set of fields and based on further determining a standard set of entries for each of the standard set of fields. Step 4004 includes receiving, via a network, a DICOM image. Step 4006 includes determining that a header of the DICOM image is incorrect. Step 4008 includes determining a selected one of the set of standard DICOM headers to replace the header of the DICOM image. Step 4010 includes transmitting the selected one of the set of standard DICOM headers, via the network, to a medical scan database for storage in conjunction with the DICOM image.

In various embodiments, the medical scan database is associated with PACS server, and the selected one of the set of standard DICOM headers of the DICOM image is transmitted to the PACS server in accordance with a DICOM communication protocol. In various embodiments, determining that the header of the DICOM image is incorrect includes determining that the header is not included in the set of standard DICOM headers. In various embodiments, determining that the DICOM image is incorrect includes determining an entry of a field of the header is not included in the set of standard entries for one of the standard set of fields corresponding to the field. In various embodiments, determining the selected one of the set of standard DICOM headers includes determining one of the set of standard entries of the one of the standard set of fields that compares most favorably to the entry.

In various embodiments, a memory of the medical scan header standardization system 3002 stores, for each of the set of standard fields, a mapping of incorrect entries to ones of the set of standard entries to one of the standard set of entries for the each of the set of standard fields. Determining the selected one of the set of standard DICOM headers includes determining one of the set of standard entries of the one of the standard set of fields by utilizing the mapping. In various embodiments, the medical scan header standardization system 3002 transmits a notification to a client device for display to a user via a display device in response to determining the mapping does not include an incorrect entry that compares favorably to the entry, where the notification indicates the entry. The medical scan header standardization system 3002 receives, from the client device, an identified one of the standard set of entries. The identified one of the standard set of entries is generated by the client device based on user input via an interactive interface in response to a prompt displayed by the display device to select one of the standard set of entries for the entry. The medical scan header standardization system 3002 generates a new mapping entry that maps the entry to the identified one of the standard set of entries. The selected one of the set of standard DICOM headers includes the identified one of the standard set of entries.

In various embodiments, the medical scan header standardization system 3002 receives a plurality of DICOM images. The set of standard DICOM headers is determined automatically based on headers of the plurality of DICOM images. In various embodiments, headers of all of the plurality of DICOM images are included in the set of standard DICOM headers. In various embodiments, determining the set of standard DICOM headers includes determining a histogram of entries for each of the standard set of fields for headers of the plurality of DICOM images. The standard set of entries is determined for each of the standard set of fields by including ones of the entries for each of the standard set of fields with counts in the histogram that compare favorably to a threshold. In various embodiments, the medical scan header standardization system 3002 determines an entry of a header of one of the plurality of DICOM images with count in the histogram that compares unfavorably to a threshold. The medical scan header standardization system 3002 determines one of the standard set of entries for a corresponding one of the standard set of fields to replace the entry. The medical scan header standardization system 3002 generates an updated header for the one of the plurality of DICOM images based on the one the standard set of entries, and transmits the updated header, via the network, to a medical scan database for storage in conjunction with the DICOM image.

In various embodiments, at least two of the standard set of DICOM fields have dependency requirements. The header includes one of the standard set of entries for each one of the standard set of fields, and the header is not included in the standard set of headers due to the at least two of the standard set of entries comparing unfavorably to the dependency requirements. In various embodiments, determining that the DICOM image is incorrect includes determining a set of fields of the header does not match the standard set of fields. In various embodiments, determining the set of fields of the header does not match the standard set of fields includes determining a number of the set of fields compares unfavorably to a number of the standard set of fields and/or an ordering of the set of fields compares unfavorably to a standard ordering of the standard set of fields. In various embodiments, determining that the header of the DICOM image is incorrect includes determining that at least one field of the DICOM header is null. The selected one of the set of standard DICOM headers includes a non-null entry for the at least one field.

In various embodiments, the header is included in the standard set of DICOM headers. Determining the header is incorrect includes automatically determining at least one property of the DICOM image. A field of the standard set of fields corresponding to the at least one property is determined. An entry of the field of the header is determined to compare unfavorably to the at least one property. Determining the selected one of the set of standard DICOM headers to replace the header includes selecting one of the standard set of entries for the field that compares favorably to the at least one property. The entry is replaced with the one of the standard set of entries. In various embodiments, the property corresponds to a modality of the DICOM image and/or an anatomical region of the DICOM image. In various embodiments, automatically determining the property includes performing an inference function that utilizes a computer vision model on image data of the DICOM image. In various embodiments, the inference function was trained on a training set of DICOM images. In various embodiments, the training set of DICOM images included headers included in the set of standard DICOM headers.

In various embodiments, the medical scan header standardization system 3002 generates an updated DICOM image by replacing the header of the DICOM image with the selected one of the set of standard DICOM headers. The updated DICOM image is transmitted to the medical scan database to replace the DICOM image.

FIG. 17A presents a flowchart illustrating a method for execution by an accession number correction system 3004 that stores executional instructions that, when executed by at least one processor, cause the accession number correction system 3004 to perform the steps below. Alternatively or in addition, some or all of the steps of FIG. 17A can be performed by the medical scan header standardization system 3002.

Step S002 includes receiving a first DICOM image from a PACS server, or other medical scan database, that stores a plurality of DICOM images. Step S004 includes determining that an accession number of the first DICOM image does not link to any corresponding one of a plurality of medical reports. Step S006 includes generating medical report criteria based on the first DICOM image. Step S008 includes transmitting a first query indicating the medical report criteria to a report database that stores the plurality of medical reports. Step S010 includes receiving a set of medical reports from the report database in response to the first query. Step S012 includes performing a comparison function on the first DICOM image and at least one of the set of medical reports to generate a comparison value for each of the at least one of the set of medical reports. Step S014 includes determining a selected one of the set of medical reports that corresponds to the first DICOM image by determining the comparison value corresponding to the selected one of the set of medical reports compares favorably to a comparison threshold. Step S016 includes generating updated report header data for the selected one of the set of medical reports, where the updated report header data includes the accession number of the first DICOM image. Step S018 includes transmitting the updated report header data to the report database for storage in conjunction with the selected one of the set of medical reports.

Alternatively or in addition to performing steps S016 and S018, the method can include generating updated DICOM image header data for the first DICOM image, where the updated DICOM image header data includes the accession number of the selected one of the set of medical reports. The updated DICOM image data can be transmitted to the PACS server for storage in conjunction with the first DICOM image.

In various embodiments, generating the medical report criteria includes extracting at least one entry of at least one field of a DICOM image header of the first DICOM image. The at least one entry of the at least one field of the DICOM image header is included in the medical report criteria. In various embodiments, the at least one entry includes a unique patient identifier and/or a service-object pair (SOP) instance unique identifier (UID). In various embodiments, the at least one entry includes at least one temporal entry corresponding to at least one temporal field, such as a time field and/or a date field. In various embodiments, generating the medical report criteria includes generating a plurality of possible accession numbers based on the accession number of the first DICOM image. All but one digit of each of the plurality of possible accession numbers match a set of digits of the accession number of the first DICOM image. The medical report criteria indicates the plurality of possible accession numbers.

In various generating the medical report criteria includes performing at least one inference function on image data of the first DICOM image to generate inference data. The inference function utilizes computer vision model trained on a training set of DICOM images. The medical report criteria indicates the inference data. In various embodiments, the inference data includes diagnosis data for at least one abnormality detected in the image data.

In various embodiments, generating the updated report header data includes generating a reformatted medical report that includes the updated report header data. Transmitting the updated report header data to the report database for storage includes transmitting the reformatted medical report to the report database to replace the selected one of the set of medical reports.

In various embodiments, determining that an accession number of the first DICOM image does not link to any corresponding one of a plurality of medical reports includes transmitting a query that includes the accession number of the first DICOM image to the report database, and receiving a response from the report database that indicates none of the plurality of medical reports stored in the report database match the accession number of the first DICOM image. In various embodiments, determining that the accession number of the first DICOM image does not link to any corresponding one of a plurality of medical reports includes transmitting a second query that includes the accession number of the first DICOM image to the report database. A medical report is received from the report database in response to the second query, where an accession number of the medical report matches the accession number of the first DICOM image. A comparison value is generated by performing the comparison function on the first DICOM image and the medical report. The first DICOM image is determined to not correspond to the medical report in response to determining the comparison value compares unfavorably to the comparison threshold.

In various embodiments, performing the comparison function on the first DICOM image and one of the set of medical reports includes comparing at least one header field of a DICOM image header of the first DICOM image to at least one corresponding header field of a report header of the one of the set of medical reports. The comparison value compares unfavorably to the comparison threshold in response to the at least one header field of the DICOM image header comparing unfavorably to the at least one corresponding header field of the report header. In various embodiments, performing the comparison function on the first DICOM image and one of the set of medical reports includes comparing at least one header field of a DICOM image header of the first DICOM image to at least one corresponding header field of a report header of the one of the set of medical reports. The comparison value compares unfavorably to the comparison threshold in response to the at least one header field of the DICOM image header comparing unfavorably to the at least one corresponding header field of the report header.

In various embodiments, performing the comparison function on the first DICOM image and one of the set of medical reports includes performing a first inference function on image data of the first DICOM image to generate first inference data. The first inference function utilizes computer vision model trained on a training set of DICOM images, and the first inference data indicates first diagnosis data for at least one abnormality detected in the image data. Performing the comparison function further includes performing a second inference function on text data of the one of the set of medical reports to generate second inference data. The second inference function utilizes a natural language model trained on a training set of medical reports, and the second inference data indicates second diagnosis data identified in the text data. Performing the comparison function further includes comparing the first inference data to the second inference data to generate the comparison value. The comparison value compares unfavorably to the comparison threshold in response to the first diagnosis data indicating a different diagnosis from the second diagnosis data.

In various embodiments, the accession number correction system 3004 receives a second DICOM image from the PACS server. The accession number correction system 3004 that an accession number of the second DICOM image is missing. The accession number correction system 3004 generates second medical report criteria based on the second DICOM image, and transmits a second query indicating the second medical report criteria to the report database. The accession number correction system 3004 receives a second set of medical reports from the report database in response to the first query, and determines a selected one of the second set of medical reports that corresponds to the second DICOM image. For example, the comparison function can be performed on the second DICOM image and at least one of the second set of medical reports to generate a comparison value for each of the at least one of the second set of medical reports, and a selected one of the second set of medical reports that corresponds to the second DICOM image is determined by determining the comparison value corresponding to the selected one of the second set of medical reports compares favorably to the comparison threshold. Updated DICOM image is header data is generated for the second DICOM image, where the updated DICOM image header data includes an accession number of the selected one of the second set of medical reports. This updated DICOM image header data of the second DICOM image is transmitted to the PACS server for storage in conjunction with the second DICOM image.

In various embodiments, generate a new accession number to be assigned to the second DICOM image and the selected one of the second set of medical reports, where the updated DICOM image header data includes the new accession number. Updated report header data is generated for the selected one of the second set of medical reports, where the updated DICOM image header data includes the new accession number. The updated report header data to the report database for storage in conjunction with the selected one of the second set of medical reports.

FIG. 17B presents a flowchart illustrating a method for execution by an accession number correction system 3004 that stores executional instructions that, when executed by at least one processor, cause the accession number correction system 3004 to perform the steps below. The accession number correction system 3004 can perform some or all of the steps of FIG. 17B instead of, or in addition to, some or all of the steps of FIG. 17A. Alternatively or in addition, some or all of the steps of FIG. 17B can be performed by the medical scan header standardization system 3002. Some or all of the various embodiments described in conjunction with FIG. 17A can be similarly applied as various embodiments of performance of the steps of FIG. 17B.

Step S102 includes receiving a second medical report from the report database. Step S104 includes determining that an accession number of the second medical report does not link to any corresponding one of a plurality of DICOM images. Step S106 includes generating DICOM image criteria based on the second medical report. Some or all of the DICOM image criteria can be generated utilizing similar embodiments as described in conjunction with generation of the medical report criteria of step S006 of FIG. 7A. Step S108 includes transmitting a second query indicating the DICOM image criteria to the PACS server. Step S110 includes receiving a set of DICOM images from the PACS server in response to the second query.

Step S112 includes performing a comparison function on the second medical report and at least one of the set of DICOM images to generate a comparison value for each of the at least one of the set of DICOM images. The comparison function can be the same or different comparison function as described in conjunction with step S012 of FIG. 7A, and can be performed utilizing any of the various embodiments of the comparison function described herein. Step S114 includes determining a selected one of the set of DICOM images that corresponds to the second medical report by determining the comparison value corresponding to the selected one of the set of DICOM images compares favorably to a comparison threshold. The comparison threshold can be the same or different comparison threshold as described in conjunction with step S014 of FIG. 7A. Step S116 includes generating updated DICOM image header data for the selected one of the set of DICOM images, where the updated DICOM image header data for the selected one of the set of DICOM images includes the accession number of the second medical report. Step S118 includes transmitting the updated DICOM image header data to the PACS server for storage in conjunction with the selected one of the set of DICOM images.

FIG. 17C presents a flowchart illustrating a method for execution by an accession number correction system 3004 that stores executional instructions that, when executed by at least one processor, cause the accession number correction system 3004 to perform the steps below. The accession number correction system 3004 can perform some or all of the steps of FIG. 17C instead of, or in addition to, some or all of the steps of FIG. 17A and/or FIG. 17B. Alternatively or in addition, some or all of the steps of FIG. 17C can be performed by the medical scan header standardization system 3002. Some or all of the various embodiments described in conjunction with FIG. 17A can be similarly applied as various embodiments of performance of the steps of FIG. 17C.

Step S202 includes determining that accession numbers of a set of DICOM images received from the PACS server do not link to any corresponding one of the plurality of medical reports stored in the report database. Step S204 includes determining that accession numbers of a set of medical reports received from the report database do not link to any corresponding one of the plurality of DICOM images stored in the PACS server. Step S206 includes performing a comparison function on each pair of one of the set of DICOM images and one of the set of medical reports to generate a plurality of comparison values. The comparison function can be the same or different comparison function as described in conjunction with step S012 of FIG. 7A, and can be performed utilizing any of the various embodiments of the comparison function described herein. Step S208 includes identifying a favorable pair by determining a corresponding comparison value compares favorably to a comparison threshold. The comparison threshold can be the same or different comparison threshold as described in conjunction with step S014 of FIG. 7A.

Step S210 includes determining a matching accession number for the one of the set of DICOM images and the one of the set of medical reports of the favorable pair. Step S212 includes facilitating storage of the matching accession number for the one of the set of DICOM images and the one of the set of medical reports in the PACS server and the report database. For example, updated report header data that indicates the matching accession number can be generated and transmitted, as discussed in steps S016 and S018 of FIG. 7A, to the report database for storage in conjunction with the one of the set of medical reports of the favorable pair. Alternatively or in addition, updated DICOM image data that indicates the matching accession number can be generated and transmitted, as discussed in steps S116 and S118 of FIG. 7B, to the PACS server for storage in conjunction with the one of the set of DICOM images of the favorable pair.

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, component values, integrated circuit process variations, temperature variations, rise and fall times, and/or thermal noise. Such relativity between items ranges from a difference of a few percent to magnitude differences. As may also be used herein, the term(s) "configured to", "operably coupled to", "coupled to", and/or "coupling" includes direct coupling between items and/or indirect coupling between items via an intervening item (e.g., an item includes, but is not limited to, a component, an element, a circuit, and/or a module) where, for an example of indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to". As may even further be used herein, the term "configured to", "operable to", "coupled to", or "operably coupled to" indicates that an item includes one or more of power connections, input(s), output(s), etc., to perform, when activated, one or more its corresponding functions and may further include inferred coupling to one or more other items. As may further be used herein, the term "associated with", includes direct and/or indirect coupling of separate items and/or one item being embedded within another item. As may still further be used herein, the term "automatically" refers to an action caused directly by a processor of a computer network in response to a triggering event and particularly without human interaction.

As may be used herein, the term "compares favorably", indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1. As may be used herein, the term "compares unfavorably", indicates that a comparison between two or more items, signals, etc., fails to provide the desired relationship.

As may also be used herein, the terms "processing module", "processing circuit", "processor", "processing device" and/or "processing unit" may be a single processing device or a plurality of processing devices. Such a processing device may be a microprocessor, micro-controller, digital signal processor, graphics processing unit, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, and/or processing unit may be, or further include, memory and/or an integrated memory element, which may be a single memory device, a plurality of memory devices, and/or embedded circuitry of another processing module, module, processing circuit, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Further note that if the processing module, module, processing circuit, and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, and/or processing unit executes, hard coded and/or operational instructions corresponding to at least some of the steps and/or functions illustrated in one or more of the Figures and/or described herein. Such a memory device or memory element can be included in an article of manufacture. While the processing module, module, processing circuit, and/or processing unit device may be a general purpose computing device, the execution of the hard coded and/or operational instructions by the processing module, module, processing circuit, and/or processing unit configures such a general purpose computing device as a special purpose computing device to implement the corresponding steps and/or functions illustrated in one or more of the Figures and/or described herein. In particular, the hard coded and/or operational instructions by the processing module, module, processing circuit, and/or processing unit implement acts and algorithms performed by the processing module, module, processing circuit, and/or processing unit. Such acts and algorithms can be identified by name, can be illustrated via flowchart and/or described in words.

One or more embodiments have been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claims. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality.

To the extent used, the flow diagram block boundaries and sequence could have been defined otherwise and still perform the certain significant functionality. Such alternate definitions of both functional building blocks and flow diagram blocks and sequences are thus within the scope and spirit of the claims. One of average skill in the art will also recognize that the functional building blocks, and other illustrative blocks, modules and components herein, can be implemented as illustrated or by discrete components, application specific integrated circuits, processors executing appropriate software and the like or any combination thereof.

In addition, a flow diagram may include a "start" and/or "continue" indication. The "start" and "continue" indications reflect that the steps presented can optionally be incorporated in or otherwise used in conjunction with other routines. In this context, "start" indicates the beginning of the first step presented and may be preceded by other activities not specifically shown. Further, the "continue" indication reflects that the steps presented may be performed multiple times and/or may be succeeded by other activities not specifically shown. Further, while a flow diagram indicates a particular ordering of steps, other orderings are likewise possible provided that the principles of causality are maintained.

The one or more embodiments are used herein to illustrate one or more aspects, one or more features, one or more concepts, and/or one or more examples. A physical embodiment of an apparatus, an article of manufacture, a machine, and/or of a process may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

The term "system" is used in the description of one or more of the embodiments. A system implements one or more functions via a device such as a processor or other processing device or other hardware that may include or operate in association with a memory that stores operational instructions. A system may operate independently and/or in conjunction with software and/or firmware. As also used herein, a system may contain one or more sub-system, each of which may be one or more systems.

As may further be used herein, a computer readable memory includes one or more memory elements. A memory element may be a separate memory device, multiple memory devices, or a set of memory locations within a memory device. Such a memory device may be a read-only memory, random access memory, volatile memory, non-volatile memory, static memory, dynamic memory, flash memory, cache memory, and/or any device that stores digital information. The memory device may be in a form a solid state memory, a hard drive memory, cloud memory, thumb drive, server memory, computing device memory, and/or other physical medium for storing digital information.

While particular combinations of various functions and features of the one or more embodiments have been expressly described herein, other combinations of these features and functions are likewise possible. The present disclosure is not limited by the particular examples disclosed herein and expressly incorporates these other combinations.

What is claimed is:

1. A medical scan header standardization system, comprising:
   at least one processor; and
   a memory that stores executable instructions that, when executed by the at least one processor, cause the medical scan header standardization system to:
   receive a plurality of DICOM images;
   determine a plurality of counts for a plurality of entries of at least one of a standard set of fields for headers of the plurality of DICOM images;
   determine a standard set of Digital Imaging and Communications in Medicine (DICOM) header entries for at least one of the standard set of fields by including ones of the entries for the each of the standard set of fields with counts of the plurality of counts that compare favorably to a threshold;
   receive a DICOM image;
   determine to correct an entry of a field the header of the DICOM image;
   select one of the standard set of DICOM header entries for the field to replace the entry of the field of the header of the DICOM image;
   train a computer vision model via artificial intelligence utilizing a training set of DICOM images that includes the DICOM image and the one of the standard set of DICOM header entries; and
   generate inference data for at least one new medical scan based on performing an inference function on image data of the at least one new medical scan via artificial intelligence by utilizing the computer vision model.

2. The medical scan header standardization system of claim 1, wherein determining to correct the entry of the header of the DICOM image is based on determining the header is incorrect.

3. The medical scan header standardization system of claim 2, wherein determining to correct the entry of the field the header of the DICOM image includes determining the entry of the field of the header is not included in the standard set of DICOM header entries for one of the at least one of the standard set of fields corresponding to the field.

4. The medical scan header standardization system of claim 3, wherein selecting the one of the standard set of DICOM header entries includes determining one of the standard set of DICOM header entries for the field that compares most favorably to the entry.

5. The medical scan header standardization system of claim 3,
   wherein the memory stores, for each of the standard set of fields, a mapping of incorrect entries to ones of the standard set of DICOM header entries to one of the standard set of DICOM header entries for the each of the standard set of fields; and
   wherein selecting the one of the standard set of DICOM header entries includes determining one of the standard set of DICOM header entries of the one of the standard set of fields by utilizing the mapping.

6. The medical scan header standardization system of claim 5, wherein the executable instructions, when executed by the at least one processor, further cause the medical scan header standardization system to:
   transmit a notification to a client device for display to a user via a display device in response to determining the mapping does not include an incorrect entry that compares favorably to the entry, wherein the notification indicates the entry;
   receive, from the client device, an identified one of the standard set of DICOM header entries, wherein the identified one of the standard set of DICOM header entries is generated by the client device based on user input via an interactive interface in response to a prompt displayed by the display device to select one of the standard set of DICOM header entries for the entry; and
   generate a new mapping entry that maps the entry to the identified one of the standard set of DICOM header entries;
   wherein the one of the standard set of DICOM header entries includes the identified one of the standard set of DICOM header entries.

7. The medical scan header standardization system of claim 1, wherein the executable instructions, when executed by the at least one processor, further cause the medical scan header standardization system to:
   receive a second DICOM image;
   determine a second header of the second DICOM image is incorrect; and
   update the second header of the second DICOM image based on the standard set of DICOM header entries.

8. The medical scan header standardization system of claim 7,
   wherein determining the second header is incorrect includes:
     automatically determining at least one property of the second DICOM image;
     determining a second field of the standard set of fields corresponding to the at least one property; and
     determining a second entry of the second field of the second header compares unfavorably to the at least one property;
   wherein updating the second header includes:
     selecting a second one of the standard set of DICOM header entries for the field that compares favorably to the at least one property; and
     replacing the second entry of the second field of the second header with the second one of the standard set of DICOM header entries.

9. The medical scan header standardization system of claim 8, wherein the second entry of the second field of the second header is included in the standard set of DICOM header entries for the field, and wherein the second one of the standard set of DICOM header entries replacing the second entry is different from the second entry.

10. The medical scan header standardization system of claim 8, wherein the property corresponds to one of: a modality of the DICOM image or an anatomical region of the DICOM image.

11. The medical scan header standardization system of claim 8, wherein the executable instructions, when executed by the at least one processor, further cause the medical scan header standardization system to:
    train a second computer vision model via artificial intelligence utilizing a training set of DICOM images; and
    automatically determine the at least one property of the second DICOM image based on performing a second inference function on second image data of the second DICOM image via artificial intelligence by utilizing the second computer vision model.

12. The medical scan header standardization system of claim 7, wherein the executable instructions, when executed by the at least one processor, further cause the medical scan header standardization system to:
train a second computer vision model via artificial intelligence utilizing a training set of DICOM images; and
automatically identify detected text in image data of the second DICOM image based on performing an inference function on the image data of the DICOM image via artificial intelligence by utilizing the second computer vision model;
wherein determining that the second header of the second DICOM image is incorrect is based on determining the second header of the second DICOM image compares unfavorably to the detected text, and wherein the second header of the second DICOM image is updated further based on the detected text.

13. The medical scan header standardization system of claim 7, wherein determining that a second header of the DICOM image is incorrect includes determining a set of fields of the second header does not match the standard set of fields based on determining at least one of: a number of the set of fields compares unfavorably to a number of the standard set of fields, or an ordering of the set of fields compares unfavorably to a standard ordering of the standard set of fields.

14. The medical scan header standardization system of claim 7, wherein determining that the second header of the second DICOM image is incorrect includes determining that at least one field of the second header is null, and wherein updating the second header includes selecting includes a non-null entry for the at least one field of the second header from the standard set of DICOM headers.

15. The medical scan header standardization system of claim 1, wherein the executable instructions, when executed by the at least one processor, further cause the medical scan header standardization system to:
determine another entry of a header of one of the plurality of DICOM images with a count in the plurality of counts that compares unfavorably to a threshold;
determine one of the standard set of DICOM header entries for a corresponding one of the standard set of fields to replace the other entry;
generate an updated header for the one of the plurality of DICOM images based on the one the standard set of DICOM header entries; and
transmit the updated header to a medical scan database for storage in conjunction with the DICOM image.

16. The medical scan header standardization system of claim 1, wherein at least two of the standard set of fields have dependency requirements, wherein the header includes one of the standard set of DICOM header entries for each one of the standard set of fields, and wherein determining to correct the entry of the header of the DICOM image is based on at least two entries of the header comparing unfavorably to the dependency requirements.

17. The medical scan header standardization system of claim 1, wherein the executable instructions, when executed by the at least one processor, further cause the medical scan header standardization system to:
generate an updated DICOM image by updating the header of the DICOM image to include the one of the standard set of DICOM header entries for the field; and
transmitting the updated DICOM image to a medical scan database to replace the DICOM image.

18. The medical scan header standardization system of claim 1, wherein medical scan database is associated with a Picture Archive and Communication System (PACS) server, and wherein an updated header of the DICOM image that includes the one of the standard set of DICOM header entries for the field is transmitted to the PACS server in accordance with a DICOM communication protocol.

19. A method comprising:
receiving a plurality of DICOM images;
determining a plurality of counts for a plurality of entries of at least one of a standard set of fields for headers of the plurality of DICOM images;
determining a standard set of Digital Imaging and Communications in Medicine (DICOM) header entries for at least one of the standard set of fields by including ones of the entries for the each of the standard set of fields with counts of the plurality of counts that compare favorably to a threshold;
receiving a DICOM image;
determining to correct an entry of a field of the header of the DICOM image;
selecting one of the standard set of DICOM header entries for the field to replace the entry of the field of the header of the DICOM image;
training a computer vision model via artificial intelligence utilizing a training set of DICOM images that includes the DICOM image and the selected one of the standard set of DICOM header entries; and
generating inference data for at least one new medical scan based on performing an inference function on image data of the at least one new medical scan via artificial intelligence by utilizing the computer vision model.

20. A medical scan header standardization system, comprising:
at least one processor; and
a memory that stores executable instructions that, when executed by the at least one processor, cause the medical scan header standardization system to:
receive a plurality of medical images;
determine a plurality of counts for a plurality of entries of at least one of a standard set of fields for headers of the plurality of medical images;
determine a standard set of header entries for at least one of the standard set of fields by including ones of the entries for the each of the standard set of fields with counts of the plurality of counts that compare favorably to a threshold;
receive an image;
determine to correct an entry of a field of the header of the image;
select one of the standard set of header entries for the field to replace the entry of the field of the header of the image;
train a computer vision model via artificial intelligence utilizing a training set of images that includes the image and the selected one of the standard set of header entries; and
generate inference data for at least one new medical image based on performing an inference function the at least one new medical image via artificial intelligence by utilizing the computer vision model.

* * * * *